(12) United States Patent
Guggisberg et al.

(10) Patent No.: US 12,376,589 B2
(45) Date of Patent: Aug. 5, 2025

(54) CHRYSEOBACTERIUM INSECT INHIBITORY MICROBIAL COMPOSITIONS AND METHODS OF MAKING AND USING

(71) Applicant: Pluton Biosciences, Inc., St. Louis, MO (US)

(72) Inventors: Ann M. Guggisberg, St. Louis, MO (US); Diana L. Beckman, St. Louis, MO (US); Boahemaa Adu-Oppong, St. Louis, MO (US); Barry S. Goldman, St. Louis, MO (US); Philip A. Ruzycki, St. Louis, MO (US); Thomas Malvar, North Stonington, CT (US); Kirk D. Narzinski, Columbia, IL (US); Farhan James William, St. Louis, MO (US); Steven C. Slater, Bainbridge Island, WA (US); Ashootosh Tripathi, Ann Arbor, MI (US); Osama Gomaa Mahmoud Mohamed, Ann Arbor, MI (US); Pamela J. Schultz, Ann Arbor, MI (US)

(73) Assignee: Pluton Biosciences, Inc., St. Louis, MO (US)

( * ) Notice: Subject to any disclaimer, the term of this patent is extended or adjusted under 35 U.S.C. 154(b) by 115 days.

(21) Appl. No.: 17/724,078

(22) Filed: Apr. 19, 2022

(65) Prior Publication Data
US 2022/0369635 A1 Nov. 24, 2022

Related U.S. Application Data

(60) Provisional application No. 63/188,961, filed on May 14, 2021.

(51) Int. Cl.
*A01N 43/38* (2006.01)
*C12N 1/20* (2006.01)

(52) U.S. Cl.
CPC .............. *A01N 43/38* (2013.01); *C12N 1/20* (2013.01)

(58) Field of Classification Search
CPC ........ A01N 25/34; A01N 25/10; A01N 43/22; A01P 7/04
See application file for complete search history.

(56) References Cited

U.S. PATENT DOCUMENTS

| | | |
|---|---|---|
| 5,695,934 A | 12/1997 | Brenner |
| 5,714,330 A | 2/1998 | Brenner et al. |
| 5,743,477 A | 4/1998 | Walsh et al. |
| 5,750,341 A | 5/1998 | Macevicz |
| 6,052,943 A * | 4/2000 | Hoffmann .......... A01G 13/0256 47/58.1 R |
| 6,306,597 B1 | 10/2001 | Macevicz |
| 6,432,360 B1 | 8/2002 | Church |
| 6,485,944 B1 | 11/2002 | Church et al. |
| 6,511,803 B1 | 1/2003 | Church et al. |
| 6,787,308 B2 | 9/2004 | Balasubramanian et al. |
| 6,833,246 B2 | 12/2004 | Balasubramanian |
| 2005/0130173 A1 | 6/2005 | Leamon et al. |
| 2006/0073161 A1 | 4/2006 | Breton |
| 2012/0100236 A1* | 4/2012 | Asolkar ............... C07K 5/0205 530/323 |
| 2014/0088167 A1* | 3/2014 | Heil ..................... C07D 209/42 548/492 |
| 2018/0049435 A1 | 2/2018 | Sikuljak et al. |
| 2018/0222861 A1 | 8/2018 | Tang et al. |
| 2019/0223441 A1 | 7/2019 | Hoffman et al. |
| 2019/0382714 A1 | 12/2019 | Wigley et al. |
| 2022/0369635 A1 | 11/2022 | Guggisberg et al. |
| 2023/0220410 A1* | 7/2023 | Chamovitz ............ A01N 37/46 800/279 |

FOREIGN PATENT DOCUMENTS

| | | |
|---|---|---|
| WO | WO 00/018957 | 4/2000 |
| WO | WO 2006/084132 | 8/2006 |
| WO | WO 2019/211850 | 11/2019 |
| WO | WO-2020183022 A1 | 9/2020 |

OTHER PUBLICATIONS

NPIC—National Pesticide Information Center (www.npic.orst.edu/pest/select.html; published Jul. 8, 2021) (Year: 2021).*
International Search Report and Written Opinion for PCT/US2022/025342. Mailed Sep. 21, 2022. 15 pages.
Abbott. A method of computing the effectiveness of an insecticide. 1925. J Am Mosq Control Assoc. Jun. 1987;3(2):302-3.
Adessi et al., Solid phase DNA amplification: characterisation of primer attachment and amplification mechanisms. Nucleic Acids Res. Oct. 15, 2000;28(20):E87. 8 pages.
Altenbuchner. Editing of the Bacillus subtilis Genome by the CRISPR-Cas9 System. Appl Environ Microbiol. Aug. 15, 2016;82(17):5421-7.
Aly et al., Floating bait formulations increase effectiveness of *Bacillus thuringiensis* var. israelensis against Anopheles larvae. J Am Mosq Control Assoc. Dec. 1987;3(4):583-8.
Andrews et al., Characterization of the lipid acyl hydrolase activity of the major potato (*Solanum tuberosum*) tuber protein, patatin, by cloning and abundant expression in a baculovirus vector. Biochem J. May 15, 1988;252(1):199-206.
Bennett et al., Toward the 1,000 dollars human genome. Pharmacogenomics. Jun. 2005;6(4):373-82.
Birren et al., Genome Analysis: Analyzing DNA, 1, Cold Spring Harbor, N.Y. 1997. TOC only. 12 pages.

(Continued)

*Primary Examiner* — Michael B. Pallay
(74) *Attorney, Agent, or Firm* — Casimir Jones, S.C.; Thomas A. Isenbarger

(57) ABSTRACT

Insect inhibitory compositions comprising certain *Chryseobacterium* organisms, compositions and compounds derived from *Chryseobacterium* organisms, methods of using the compositions to inhibit insects that are injurious to humans, animals, and plants, and methods of making the compositions are disclosed.

15 Claims, 33 Drawing Sheets

Specification includes a Sequence Listing.

(56) References Cited

OTHER PUBLICATIONS

Brenner et al., Gene expression analysis by massively parallel signature sequencing (MPSS) on microbead arrays. Nat Biotechnol. Jun. 2000;18(6):630-4.
Chen et al., Catalytic Asymmetric synthesis of 3,3' -Bisindoles Bearing Single Axial Chirality. J. Org. Chem. 2020, 85, 10152-10166.
Cheung et al., Micro-lipid-droplet encapsulation of *Bacillus thuringiensis* subsp. *israelensis* delta-endotoxin for control of mosquito larvae. Appl Environ Microbiol. Oct. 1985;50(4):984-8.
Compendium of Herbicide Adjuvants, 13th Edition, Southern Illinois University, 2016. 76 pages.
Czapla et al., Effect of Plant Lectins on the Larval Development of European Corn Borer (Lepidoptera: Pyralidae) and Southern Corn Rootworm (Coleoptera: Chrysomelidae). Journal of Econocomic Entomology. 1990, 83, 6, 2480-2485.
Desantis et al., High-density universal 16S rRNA microarray analysis reveals broader diversity than typical clone library when sampling the environment. Microb Ecol. Apr. 2007;53(3):371-83.
Finn et al., The Pfam protein families database: towards a more sustainable future. Nucleic Acids Res. Jan. 4, 2016;44(D1):D279-85.
Gao et al., Microarray-based analysis of microbial community RNAs by whole-community RNA amplification. Appl Environ Microbiol. Jan. 2007;73(2):563-71.
Garrity et al., Taxonomic Outline of Bacteria and Archaea. The Taxonomic Outline of Bacteria and Archaea. TOBA Release 7.7, Mar. 2007. 141 pages.
Guo et al., Highly Enantioselective Alkylaiton Reaction of Enamides by Bronsted-Acid Catalysis. Organic Letters 2009, 11, 4620-4623 and associated supporting information. 84 pages.
Hinchee et al., Production of Transgenic Soybean Plants Using Agrobacterium-Mediated DNA Transfer. Bio/Technology. 1988, 6, 915- 922.
Hurt et al., Simultaneous recovery of RNA and DNA from soils and sediments. Appl Environ Microbiol. Oct. 2001;67(10):4495-503.
Ishida et al., High efficiency transformation of maize (*Zea mays* L.) mediated by Agrobacterium tumefaciens. Nat Biotechnol. Jun. 1996;14(6):745-50.
Kang et al., Streptindole and Its Derivatives as Novel Antiviral and Anti-Phytopathogenic Fungus Agents. J. Agric. Food Chem. 2020, 68, 7839-7849.
Kushwah et al., Pyrethroid-resistance and presence of two knockdown resistance (kdr) mutations, F1534C and a novel mutation T15201, in Indian Aedes aegypti. PLoS Negl Trop Dis. Jan. 8, 2015;9(1):e3332. 8 pages.
Kushwah et al., Status of DDT and pyrethroid resistance in Indian Aedes albopictus and absence of knockdown resistance (kdr) mutation. J Vector Borne Dis. Mar. 2015;52(1):95-8.
Lacey et al., Effect of formulation, concentration, and application time on the efficacy of Bacillus thuringiensis (H-14) against black fly (Diptera: Simuliidae) larvae under natural conditions. J Econ Entomol. Apr. 1984;77(2):412-8.
MacLean et al., Application of 'next-generation' sequencing technologies to microbial genetics. Nat Rev Microbiol. Apr. 2009;7(4):287-96.
Manual on Development and Use of FAO and WHO Specifications for Pesticides, United Nations, First Edition, Third Revision. 2016. 306 pages.
Margulies et al., Genome sequencing in microfabricated high-density picolitre reactors. Nature. Sep. 15, 2005;437(7057):376-80.
Marrone et al., Improvements in Laboratory Rearing of the Southern Corn Rootworm, Diabrotica undecimpuncta howardi Barber (Coleoptera: Chrysomelidae), on an Artificial Diet and Corn. Journal of Economic Entomology, vol. 78, Issue 1, Feb. 1, 1985, pp. 290-293.
McCutcheon's Detergents and Emulsifiers Annual, MC Publishing Corp., Ridgewood New Jersey. 1996. TOC only. 2 pages.
McGrath et al., Isolation and analysis of mRNA from environmental microbial communities. J Microbiol Methods. Oct. 2008;75(2):172-6.
Mei et al., Indolylmethanols as Reactants in Catalytic Asymmetric Reactions. J. Org. Chem. 2017, 82, 7695-7707.
Mistry et al., Pfam: The protein families database in 2021. Nucleic Acids Res. Jan. 8, 2021;49(D1):D412-D419.
Mitra et al., Fluorescent in situ sequencing on polymerase colonies. Anal Biochem. Sep. 1, 2003;320(1):55-65.
Morozova et al., Applications of next-generation sequencing technologies in functional genomics. Genomics. Nov. 2008;92(5):255-64.
Porter et al., Mosquitocidal toxins of bacilli and their genetic manipulation for effective biological control of mosquitoes. Microbiol Rev. Dec. 1993;57(4):838-61.
Salter et al., Reagent and laboratory contamination can critically impact sequence-based microbiome analyses. BMC Biol. Nov. 12, 2014;12:87. 12 pages.
Schnepf et al., Bacillus thuringiensis and its pesticidal crystal proteins. Microbiol Mol Biol Rev. Sep. 1998;62(3):775-806.
Shendure et al., Accurate multiplex polony sequencing of an evolved bacterial genome. Science. Sep. 9, 2005;309(5741):1728-32.
Sorrell, Organic Chemistry, 2nd edition, University Science Books, Sausalito, 2006, TOC only. 8 pages.
Sparks et al., IRAC: Mode of action classification and insecticide resistance management. Pestic Biochem Physiol. Jun. 2015;121:122-8.
Voelkerding et al., Next-generation sequencing: from basic research to diagnostics. Clin Chem. Apr. 2009;55(4):641-58.
Woese et al., Towards a natural system of organisms: proposal for the domains Archaea, Bacteria, and Eucarya. Proc Natl Acad Sci U S A. Jun. 1990;87(12):4576-9.
Wu et al., Microarray-based analysis of subnanogram quantities of microbial community DNAs by using whole-community genome amplification. Appl Environ Microbiol. Jul. 2006;72(7):4931-41.
Zhou et al., DNA recovery from soils of diverse composition. Appl Environ Microbiol. Feb. 1996;62(2):316-22.
Database Embl [Online]., "Chryseobacterium Gleum ATCC 35910 DNA-Directed RNA Polymerase, Alpha Subunit", Jul. 15, 2010 (Jul. 15, 2010), ID—EFK37989, SV 1, linear, genomic DNA, WGS, PRO, 996 BP, XP002813034, retrieved from EBI accession No. EMBL: EFK37989, sequence, 3 Pages.
Database Embl [Online]., "Chryseobacterium Gleum DNA Gyrase Subunit A", Dec. 19, 2018 (Dec. 19, 2018), ID—VEE05492, SV 1, linear, genomic DNA, STD, PRO, 2592 BP, XP002813028, retrieved from EBI accession No. EMBL: VEE05492, sequence, 3 Pages.
Eski A., et al., "Identification and Pathogenicity of Bacteria in the Mediterranean Corn Borer Sesamia Nonagrioides Lefebvre (Lepidoptera: Noctuidae)", Turkish Journal of Biology, vol. 39, No. 1, Jan. 1, 2015 (Jan. 1, 2015), pp. 31-48, XP055611950, TR ISSN: 1300-0152, DOI: 10.3906/biy-1402-69, the whole document, SN6, figure 5.
Supplementary European Search Report for European Patent Application No. 22808018.0, dated Mar. 10, 2025, 8 Pages.

* cited by examiner

| Description | Scientific Name |
|---|---|
| Chryseobacterium gleum strain NCTC11432 genome assembly, chromosome: 1 | Chryseobacterium gleum |
| Chryseobacterium gleum strain FDAARGOS_1103 chromosome | Chryseobacterium gleum |
| Chryseobacterium arthrosphaerae strain FDAARGOS_519 chromosome, complete genome | Chryseobacterium arthrosphaerae |
| Chryseobacterium flavum strain KCTC 12877 16S ribosomal RNA gene, partial sequence | Chryseobacterium flavum |
| Chryseobacterium indologenes strain FDAARGOS_648 chromosome | Chryseobacterium indologenes |
| Chryseobacterium cucumeris strain MW-6 16S ribosomal RNA gene, partial sequence | Chryseobacterium cucumeris |
| Chryseobacterium lactis strain KC_1864 chromosome, complete genome | Chryseobacterium lactis |
| Chryseobacterium bernardetii strain G0229 chromosome, complete genome | Chryseobacterium bernardetii |
| Chryseobacterium timonianum strain G972 16S ribosomal RNA, partial sequence | Chryseobacterium timonianum |
| Chryseobacterium aureum strain 17S1E7 chromosome | Chryseobacterium aureum aureum |
| Chryseobacterium jejuense strain JDG189 16S ribosomal RNA gene, partial sequence | Chryseobacterium jejuense |
| Chryseobacterium nakagawai strain G0041 chromosome, complete genome | Chryseobacterium nakagawai |
| Endosymbiont of Nilaparvata lugens clone M293 16S ribosomal RNA gene, partial sequence | endosymbiont of Nilaparvata lugens |
| Chryseobacterium joostei strain DSM 16927 chromosome, complete genome | Chryseobacterium joostei |
| Chryseobacterium jlt 16S ribosomal RNA gene, partial sequence | Chryseobacterium sp. jlt |
| Chryseobacterium gallinarum strain FDAARGOS_636 chromosome, complete genome | Chryseobacterium gallinarum |
| Chryseobacterium rhizoplanae partial 16S rRNA gene, strain R-54350 | Chryseobacterium rhizoplanae |

FIG. 6A

| Description | Max Score | Total Score | Query Cover | E value | Per. ident | Acc. Len | Accession |
|---|---|---|---|---|---|---|---|
| Chryseobacterium gleum strain NCTC11432 genome assembly, chromosome: 1 | 2795 | 16678 | 100% | 0 | 100 | 5608922 | LR134289.1 |
| Chryseobacterium gleum strain FDAARGOS_1103 chromosome | 2795 | 16678 | 100% | 0 | 100 | 5643321 | CP068486.1 |
| Chryseobacterium arthrosphaerae strain FDAARGOS_519 chromosome, complete genome | 2734 | 16375 | 100% | 0 | 99.27 | 5361872 | CP033811.1 |
| Chryseobacterium flavum strain KCTC 12877 16S ribosomal RNA gene, partial sequence | 2728 | 2728 | 100% | 0 | 99.21 | 1523 | MK116543.1 |
| Chryseobacterium indologenes strain FDAARGOS_648 chromosome | 2723 | 16332 | 100% | 0 | 99.14 | 4799263 | CP050961.1 |
| Chryseobacterium cucumeris strain MW-6 16S ribosomal RNA gene, partial sequence | 2689 | 2689 | 100% | 0 | 98.74 | 1517 | MW630117.1 |
| Chryseobacterium lactis strain KC_1864 chromosome, complete genome | 2684 | 16100 | 100% | 0 | 98.68 | 5618212 | CP033924.1 |
| Chryseobacterium bernardetii strain G0229 chromosome, complete genome | 2651 | 18374 | 100% | 0 | 98.28 | 5318634 | CP033932.1 |
| Chryseobacterium timonianum strain G972 16S ribosomal RNA, partial sequence | 2647 | 2647 | 99% | 0 | 98.41 | 1505 | NR_164811.1 |
| Chryseobacterium aureum strain 17S1E7 chromosome | 2639 | 15812 | 100% | 0 | 98.15 | 5069854 | CP034661.1 |
| Chryseobacterium jejuense strain JDG189 16S ribosomal RNA gene, partial sequence | 2636 | 2636 | 99% | 0 | 98.4 | 1512 | JX035956.1 |
| Chryseobacterium nakagawai strain G0041 chromosome, complete genome | 2634 | 18430 | 100% | 0 | 98.08 | 5595345 | CP033923.1 |
| Endosymbiont of Nilaparvata lugens clone M293 16S ribosomal RNA gene, partial sequence | 2608 | 2608 | 97% | 0 | 98.58 | 1478 | JQ975885.1 |
| Chryseobacterium jootsei strain DSM 16927 chromosome, complete genome | 2606 | 18247 | 100% | 0 | 97.75 | 4860412 | CP033926.1 |
| Chryseobacterium jil 16S ribosomal RNA gene, partial sequence | 2599 | 2599 | 99% | 0 | 97.81 | 1509 | AY278484.2 |
| Chryseobacterium gallinarum strain FDAARGOS_636 chromosome, complete genome | 2584 | 15457 | 100% | 0 | 97.49 | 4337626 | CP050995.1 |
| Chryseobacterium rhizoplanae partial 16S rRNA gene, strain R-54350 | 2577 | 2577 | 97% | 0 | 98.3 | 1469 | LN995706.1 |

FIG. 6B

CHRYSEOBACTERIUM INSECT INHIBITORY MICROBIAL COMPOSITIONS AND METHODS OF MAKING AND USING

STATEMENT OF RELATED APPLICATIONS

This application claims priority to U.S. Provisional Patent Application No. 63/188,961, filed May 14, 2021, the entire contents of which are incorporated herein by reference for all purposes.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Apr. 19, 2022, is named "40129-202_SEQUENCE_LISTING_ST25.txt" and is 14,009,737 bytes in size.

INCORPORATION OF TABLES

The tables filed herewith in the files:
"PLU6_Table1.txt";
"PLU6_Table2.txt";
are part of the disclosure of this application and are incorporated herein in their entireties.

LENGTHY TABLES

The patent contains a lengthy table section. A copy of the table is available in electronic form from the USPTO web site (https://seqdata.uspto.gov/?pageRequest=docDetail&DocID=US12376589B2). An electronic copy of the table will also be available from the USPTO upon request and payment of the fee set forth in 37 CFR 1.19(b)(3).

FIELD

This disclosure is drawn to certain insect inhibitory compositions comprising *Chryseobacterium* strains, insect inhibitory compositions and compounds derived from *Chryseobacterium* organisms, plant parts treated with the insect inhibitory compositions, methods of using the insect inhibitory compositions to control insects, and methods of making the insect inhibitory compositions.

BACKGROUND

Insect pests can afflict humans, livestock, companion animals, and plants either directly or indirectly by serving as vectors for a variety of pathogens and parasites. As insect resistance to insecticides is an ongoing problem, there is an ongoing need for new insect control agents to both inhibit insecticide resistant insects and stall development of such resistance.

Agents that can inhibit Dipteran insects including mosquitos such as *Aedes* species are of particular value. *Aedes aegypti* mosquitoes are known carriers of human diseases, including Zika virus, Chikungunya, Dengue, and Yellow Fever that are particularly problematic. Reports of resistance to DDT and pyrethroid insecticides in certain *Aedes* populations (Kushwah et al. PLoS Negl Trop Dis. 2015 Jan. 8; 9(1):e3332; Kushwah et al. J Vector Borne Dis. 2015 March; 52(1):95-8) underscore the importance of identifying other insect inhibitory agents with distinct modes of action.

SUMMARY

Provided for herein are compositions comprising: (i) a *Chryseobacterium* monoculture or a product thereof wherein the *Chryseobacterium* comprises: (a) at least one coding region encoding a protein with at least 95%, 96%, 97%, 98%, 99%, 99.5%, 99.8%, 99.9%, or 100% sequence identity across the entire length of SEQ ID NO: 1 (MKCIGJBJ_03627 DNA gyrase subunit A), at least 95%, 96%, 97%, 98%, 99%, 99.5%, 99.8%, 99.9%, or 100% sequence identity across the entire length of SEQ ID NO: 2 (MKCIGJBJ_03079 DNA topoisomerase 1), at least 95%, 96%, 97%, 98%, 99%, 99.5%, 99.8%, 99.9%, or 100% sequence identity across the entire length of SEQ ID NO: 3 (MKCIGJBJ_00500 DNA-directed RNA polymerase subunit beta), at least 95%, 96%, 97%, 98%, 99%, 99.5%, 99.8%, 99.9%, or 100% sequence identity across the entire length of SEQ ID NO: 4 (MKCIGJBJ_00499 DNA-directed RNA polymerase subunit beta'), and/or at least 95%, 96%, 97%, 98%, 99%, 99.5%, 99.8%, 99.9%, or 100% sequence identity across the entire length of SEQ ID NO: 5 (MKCIGJBJ_02095 DNA-directed RNA polymerase subunit alpha); (b) at least one gene encoding a protein with at least 95%, 96%, 97%, 98%, 99%, 99.5%, 99.8%, 99.9%, or 100% sequence identity across the entire length of a sequence contained in Appendix A (PLU6_1-PLU6_352; SEQ ID NO: 851-1202); (c) any combination of any coding region of (a) or any gene of (b); (d) *Chryseobacterium* strain PLU6 deposited as ATCC Patent Deposit Number PTA-127072, a variant thereof, or progeny thereof; or (e) *Chryseobacterium* strain PLU6 deposited as ATCC Patent Deposit Number PTA-127072, a variant thereof, or progeny thereof, wherein the variant or progeny comprise any coding region of (a), any gene of (b), or any combination of coding regions of (a) and/or genes of (b). In certain embodiments, the composition comprises (ii) an adjuvant and/or excipient.

Certain embodiments provide for a kit comprising a *Chryseobacterium* composition of this disclosure, and at least one of an application device, diluent, and/or vessel.

Certain embodiments provide for a plant part that is at least partially coated with a *Chryseobacterium* composition of this disclosure.

Provided for herein is a method for inhibiting growth, reproduction, egg laying, development, and/or feeding of an insect (e.g., a dipteran, a lepidopteran) comprising exposing the insect to an insect inhibitory amount of a *Chryseobacterium* composition of this disclosure.

Certain embodiments provide for a method of reducing insect damage to a plant comprising the step of applying an insect inhibitory amount of a *Chryseobacterium* composition of this disclosure to one or more parts of the plant, to soil that is adjacent to the plant, and/or to soil in which the plant is grown.

Certain embodiments provide for a method of making an insect inhibitory composition comprising the step of combining: (i) a monoculture of a *Chryseobacterium* organism that comprises: (a) at least one coding region encoding a protein with at least 95%, 96%, 97%, 98%, 99%, 99.5%, 99.8%, 99.9%, or 100% sequence identity across the entire length of SEQ ID NO: 1 (MKCIGJBJ_03627 DNA gyrase subunit A), at least 95%, 96%, 97%, 98%, 99%, 99.5%, 99.8%, 99.9%, or 100% sequence identity across the entire length of SEQ ID NO: 2 (MKCIGJBJ_03079 DNA topoisomerase 1), at least 95%, 96%, 97%, 98%, 99%, 99.5%, 99.8%, 99.9%, or 100% sequence identity across the entire length of SEQ ID NO: 3 (MKCIGJBJ_00500 DNA-directed RNA polymerase subunit beta), at least 95%, 96%, 97%, 98%, 99%, 99.5%, 99.8%, 99.9%, or 100% sequence identity across the entire length of SEQ ID NO: 4 (MKCIGJBJ_00499 DNA-directed RNA polymerase subunit beta'), and/or at least 95%, 96%, 97%, 98%, 99%, 99.5%, 99.8%, 99.9%, or 100% sequence identity across the entire length of SEQ ID NO: 5 (MKCIGJBJ_02095 DNA-directed RNA polymerase subunit alpha); (b) at least one gene encoding a protein with at least 95%, 96%, 97%, 98%, 99%, 99.5%, 99.8%, 99.9%, or 100% sequence identity across the entire length of a sequence contained in Appendix A (PLU6_1-PLU6_352; SEQ ID NO: 851-1202); (c) any combination of any coding region of (a) or any gene of (b); (d) *Chryseobacterium* strain PLU6 deposited as ATCC Patent Deposit Number PTA-127072, a variant thereof, or progeny thereof; or (e) *Chryseobacterium* strain PLU6 deposited as ATCC Patent Deposit Number PTA-127072, a variant thereof, or progeny thereof, wherein the variant or progeny comprise any coding region of (a), any gene of (b), or any combination of coding regions of (a) and/or genes of (b); and (ii) at least one adjuvant and/or excipient, thereby making an insect inhibitory composition.

In some embodiments, the PLU6 organism or PLU6-type organism is a *Chryseobacterium* species, e.g., *C. timonianum, C. indologenes, C. gleum*, or *C. rhizosphaerae*, having insecticidal activity, e.g., having killing activity against dipterans and/or lepidopterans (e.g., an insect from a genus *Aedes, Anticarsia, Culex, Anopheles, Heliothis, Trichoplusia, Spodoptera, Chrysodeixis, Diatraea, Helicoverpa*, or *Chloridea*).

Accordingly, in some embodiments, the technology provides a method of killing an insect. For example, embodiments of methods comprise contacting an insect with a microbial organism that is PLU6, a PLU6-type organism, or an organism having an insecticidal activity similar to PLU6 or a PLU6-type organism. In some embodiments, the microbial organism produces a diindolylalkane compound. In some embodiments, the diindolylalkane compound is 3,3-diindolylmethane or 3-((1H-indol-2-yl)methyl)-1H-indole. In some embodiments, the insect is a lepidopteran or dipteran. In some embodiments, the insect is from the family Culicidae, Noctuidae, Tortricidae, Crambidae, or Erebidae. In some embodiments, the insect is from the genus *Aedes, Anticarsia, Culex, Anopheles, Heliothis, Trichoplusia, Spodoptera, Chrysodeixis, Diatraea, Helicoverpa*, or *Chloridea*. In some embodiments, the insect is *Aedes aegpyti, Culex quinquefasciatus, Heliothis viriscens, Trichoplusia ni, Spodoptera exigua, Chrysodeixis includens, Helicoverpa zea, Spodoptera eridania, Spodoptera frugiperda, Diatraea saccharalis, Diatraea grandiosella, Anopheles quadrimaculatus*, or *Anticarsia gemmetalis.*

In some embodiments, the microbial organism (e.g., PLU6-type organism) comprises a nucleotide sequence having at least 95% sequence identity to one or more sequences provided by one or more of SEQ ID NO: 78-82 (16S rRNA gene, 23S rRNA gene, and three different 5S rRNA genes).

In some embodiments, the microbial organism (e.g., PLU6-type organism) comprises a nucleotide sequence having at least 95% sequence identity to one or more sequences provided by a sequence of SEQ ID NO: 83; SEQ ID NO: 84-157; SEQ ID NO: 158-234; SEQ ID NO: 235-464; SEQ ID NO: 465-723; or SEQ ID NO: 724-850, corresponding to sequences associated with the phylogenetic clades 1-6, respectively, as shown in FIG. 10.

In some embodiments, the microbial organism (e.g., PLU6-type organism) comprises a nucleotide sequence encoding a polypeptide having at least 95% sequence identity to one or more amino acid sequences provided by SEQ ID NO: 1-5 (DNA gyrase subunit A, DNA topoisomerase 1, DNA-directed RNA polymerase subunit beta, DNA-directed RNA polymerase subunit beta', DNA-directed RNA polymerase subunit alpha); or comprises a nucleotide sequence encoding a polypeptide having at least 95% sequence identity to one or more amino acid sequences provided by a sequence SEQ ID NO: 851-1202 (Appendix A).

In some embodiments, the technology provides a method of producing an insecticide. For instance, in some embodiments, methods comprise growing a liquid culture comprising a microbial organism that is PLU6, a PLU6-type organism, or an organism having an insecticidal activity similar to PLU6 or a PLU6-type organism. In some embodiments, the microbial organism (e.g., PLU6-type organism) comprises a nucleotide sequence having at least 95% sequence identity to one or more sequences provided by one or more of SEQ ID NO: 78-82 (16S rRNA gene, 23S rRNA gene, and three different 5S rRNA genes). In some embodiments, the microbial organism (e.g., PLU6-type organism) comprises a nucleotide sequence having at least 95% sequence identity to one or more sequences provided by a sequence of SEQ ID NO: 83; SEQ ID NO: 84-157; SEQ ID NO: 158-234; SEQ ID NO: 235-464; SEQ ID NO: 465-723; or SEQ ID NO: 724-850 corresponding to sequences associated with the phylogenetic clades 1-6, respectively, as shown in FIG. 10. In some embodiments, the microbial organism (e.g., PLU6-type organism) comprises a nucleotide sequence encoding a polypeptide having at least 95% sequence identity to one or more amino acid sequences provided by SEQ ID NO: 1-5 (DNA gyrase subunit A, DNA topoisomerase 1, DNA-directed RNA polymerase subunit beta, DNA-directed RNA polymerase subunit beta', DNA-directed RNA polymerase subunit alpha); or comprises a nucleotide sequence encoding a polypeptide having at least 95% sequence identity to one or more amino acid sequences provided by a sequence SEQ ID NO: 851-1202 (Appendix A).

In some embodiments, methods further comprise isolating an insecticidal compound from said liquid culture. In some embodiments, methods further comprise isolating the microbial organism that is PLU6, a PLU6-type organism, or an organism having an insecticidal activity similar to PLU6 or a PLU6-type organism. In some embodiments, the insecticidal compound is a diindolylalkane compound. In some embodiments, the diindolylalkane compound is 3,3-diindolylmethane or 3-((1H-indol-2-yl)methyl)-1H-indole.

In some embodiments, the technology relates to heterologous expression of an insecticidal compound. In some embodiments, the technology relates to heterologous expression of one or more polypeptides from PLU6, a PLU6-type organism, or an organism having an insecticidal activity similar to PLU6 or a PLU6-type organism functioning to produce an insecticidal compound. In some embodiments, the technology relates to heterologous expression of one or more polypeptides of a biosynthetic pathway, biological system, metabolic pathway, metabolic network, gene cluster, operon, or other group of genes, proteins, and/or enzymes from PLU6, a PLU6-type organism, or an organism having an insecticidal activity similar to PLU6 or a PLU6-type organism that function to produce an insecticidal compound (e.g., an indolylalkane). In some embodiments, methods comprise expressing an insecticide from a nucleotide sequence obtained from PLU6, a PLU6-type organism, or an organism having an insecticidal activity similar to PLU6 or a PLU6-type organism. In some embodiments, methods comprise expressing a protein from a nucleotide sequence obtained from PLU6, a PLU6-type organism, or an organism having an insecticidal activity similar to PLU6 or a PLU6-type organism, wherein the protein functions alone or with other proteins to produce an insecticidal compound. In some embodiments, methods comprise expressing a product (e.g., an insecticide or a protein functioning to produce an insecticide) in a heterologous host that comprises one or more nucleotide sequences obtained from PLU6, a PLU6-type organism, or an organism having an insecticidal activity similar to PLU6 or a PLU6-type organism. In some embodiments, the one or more nucleotide sequences comprise a sequence provided by SEQ ID NO: 83, 84-157, 158-234, 235-464, 465-723, or 724-850. In some embodiments, the nucleotide sequence encodes a polypeptide having an amino acid sequence provided by one or more sequences provided by SEQ ID NO: 851-1202 (Appendix A).

In some embodiments, the technology provides a heterologous organism (e.g., a microbe or a plant) comprising a nucleic acid from PLU6, a PLU6-type organism, or an organism having an insecticidal activity similar to PLU6 or a PLU6-type organism. In some embodiments, the nucleotide sequence is a sequence provided by SEQ ID NO: 83, 84-157, 158-234, 235-464, 465-723, or 724-850. In some embodiments, the nucleotide sequence encodes a polypeptide having an amino acid sequence provided by one or more sequences provided by SEQ ID NO: 851-1202 (Appendix A). In some embodiments, the technology provides a heterologous organism expressing one or more polypeptides from PLU6, a PLU6-type organism, or an organism having an insecticidal activity similar to PLU6 or a PLU6-type organism functioning to produce an insecticidal compound. In some embodiments, the technology relates to a heterologous organism expressing one or more polypeptides of a biosynthetic pathway, biological system, metabolic pathway, metabolic network, gene cluster, operon, or other group of genes, proteins, and/or enzymes from PLU6, a PLU6-type organism, or an organism having an insecticidal activity similar to PLU6 or a PLU6-type organism that function to produce an insecticidal compound.

In some embodiments, the technology provides a method of producing an insect-resistant plant, said method comprising expressing in the plant a product encoded by a nucleotide sequence of PLU6, a PLU6-type organism, or an organism having an insecticidal activity similar to PLU6 or a PLU6-type organism. In some embodiments, the product encoded by a nucleotide sequence of PLU6, a PLU6-type organism, or an organism having an insecticidal activity similar to PLU6 or a PLU6-type organism is a polypeptide that functions alone or with other proteins to produce a diindolylalkane compound (e.g., a diindolylalkane as described herein). In some embodiments, the plant comprises a nucleotide sequence provided by SEQ ID NO: 83, 84-157, 158-234, 235-464, 465-723, or 724-850. In some embodiments, the plant comprises a nucleotide sequence that encodes a polypeptide having an amino acid sequence provided by one or more sequences provided by SEQ ID NO: 851-1202 (Appendix A). In some embodiments, the technology provides a method of producing a plant expressing one or more polypeptides from PLU6, a PLU6-type organism, or an organism having an insecticidal activity similar to PLU6 or a PLU6-type organism. In some embodiments, the technology relates to a method of producing a plant expressing one or more polypeptides of a biosynthetic pathway, biological system, metabolic pathway, metabolic network, gene cluster, operon, or other group of genes, proteins, and/or enzymes from PLU6, a PLU6-type organism, or an organism having an insecticidal activity similar to PLU6 or a PLU6-type organism.

In some embodiments, the technology provides a plant expressing a product encoded by a nucleotide sequence of PLU6, a PLU6-type organism, or an organism having an insecticidal activity similar to PLU6 or a PLU6-type organism. In some embodiments, the product encoded by a nucleotide sequence of PLU6, a PLU6-type organism, or an organism having an insecticidal activity similar to PLU6 or a PLU6-type organism is a protein that functions alone or with other proteins to produce a diindolylalkane compound (e.g., a diindolylalkane as described herein). In some embodiments, the plant comprises a nucleotide sequence of PLU6, a PLU6-type organism, or an organism having an insecticidal activity similar to PLU6 or a PLU6-type organism is provided by SEQ ID NO: 83, 84-157, 158-234, 235-464, 465-723, or 724-850. In some embodiments, the plant comprises a nucleotide sequence that encodes a polypeptide having an amino acid sequence provided by one or more sequences provided by SEQ ID NO: 851-1202 (Appendix A). In some embodiments, the technology provides a plant expressing one or more polypeptides from PLU6, a PLU6-type organism, or an organism having an insecticidal activity similar to PLU6 or a PLU6-type organism. In some embodiments, the technology relates to a plant expressing one or more polypeptides of a biosynthetic pathway, biological system, metabolic pathway, metabolic network, gene cluster, operon, or other group of genes, proteins, and/or enzymes from PLU6, a PLU6-type organism, or an organism having an insecticidal activity similar to PLU6 or a PLU6-type organism.

In some embodiments, the technology provides a method of killing an insect by contacting an insect with a dindolylalkyl compound. In some embodiments, the dindolylalkyl compound is 3,3-diindolylmethane. In some embodiments, the diindolylalkane compound is 3-((1H-indol-2-yl)methyl)-1H-indole. In some embodiments, the insect is a lepidopteran or dipteran. In some embodiments, the insect is from the family Culicidae, Noctuidae, Tortricidae, Crambidae, or Erebidae. In some embodiments, the insect is from the genus *Aedes, Anticarsia, Culex, Anopheles, Heliothis, Trichoplusia, Spodoptera, Chrysodeixis, Diatraea, Helicoverpa,* or *Chloridea*. In some embodiments, the insect is *Aedes aegpyti, Anopheles quadrimaculatus, Culex quinquefasciatus, Heliothis viriscens, Trichoplusia ni, Spodoptera exigua, Chrysodeixis includens, Helicoverpa zea, Spodoptera eridania, Spodoptera frugiperda, Diatraea saccharalis, Diatraea grandiosella,* or *Anticarsia gemmetalis*. In some embodiments, the dindolylalkyl compound (e.g., 3,3-diindolylmethane or 3-((1H-indol-2-yl)methyl)-1H-indole) is produced by a PLU6 organism, a PLU6-type organism, or an organism having an insecticidal activity similar to PLU6 or a PLU6-type organism.

In some embodiments, methods of killing an insect comprise producing a dindolylalkyl compound (e.g., 3,3-diindolylmethane or 3-((1H-indol-2-yl)methyl)-1H-indole)

using a PLU6 organism, a PLU6-type organism, or an organism having an insecticidal activity similar to PLU6 or a PLU6-type organism (e.g., by culturing the PLU6 organism, a PLU6-type organism, or an organism having an insecticidal activity similar to PLU6 or a PLU6-type organism) and contacting the insect with the diindolylalkyl compound or with a composition comprising the diindolylalkyl compound (e.g., a culture comprising the PLU6 organism, a PLU6-type organism, or an organism having an insecticidal activity similar to PLU6 or a PLU6-type organism and the diindolylalkane compound; or a composition comprising an isolated diindolylalkyl compound).

In some embodiments, the technology provides a method of producing an indole compound. For example, in some embodiments, methods comprise growing a liquid culture comprising a microbial organism that is PLU6 or a PLU6-type organism. In some embodiments, the microbial organism comprises a nucleotide sequence provided by SEQ ID NO: 78-82; 83, 84-157, 158-234, 235-464, 465-723, or 724-850; or the microbial organism comprises a nucleotide sequence encoding a polypeptide comprising an amino acid sequence provided by SEQ ID NO: 1-5; or 851-1202. In some embodiments, methods further comprise isolating an indole compound from said liquid culture. In some embodiments, the indole compound is a tri-indole compound or a tetra-indole compound. In some embodiments, the indole compound has a structure according to

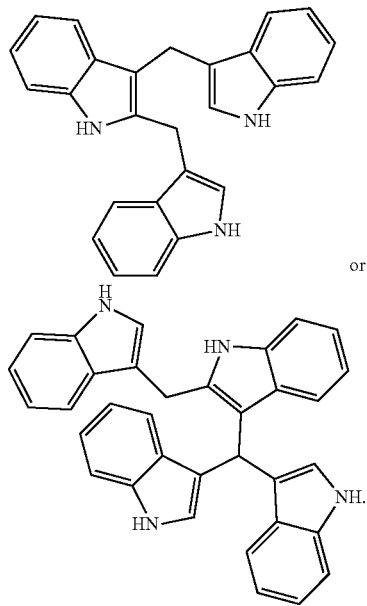

In some embodiments, the microbial organism is a heterologous organism comprising a nucleotide sequence obtained from PLU6 or a PLU6-type organism. In some embodiments, the heterologous organism comprises a nucleotide sequence that is a nucleotide sequence provided by SEQ ID NO: 78-82; 83, 84-157, 158-234, 235-464, 465-723, or 724-850; or is a nucleotide sequence encoding a polypeptide comprising an amino acid sequence provided by SEQ ID NO: 1-5; or 851-1202.

Additional embodiments will be apparent to persons skilled in the relevant art based on the teachings contained herein.

BRIEF DESCRIPTION OF THE DRAWINGS/FIGURES

These and other features, aspects, and advantages of the present technology will become better understood with regard to the following drawings.

FIG. 1 is a bar plot of data showing the larvicidal activity of PLU6 against various species of mosquito larvae (*Aedes aegypti, Culex quinquefasciatus*, and *Anopheles quadrimaculatus*). The bioactive culture of PLU6 was grown for 2 days. Mortality was assessed 72 hours after application to third-instar larvae. Error bars represent standard deviations from at least three independent biological replicates. "Neg. control" represents data obtained using *Bacillus thuringiensis* subspecies *israelensis* strain 4Q7 from the Bacillus Genetic Stock Center (Ohio State University, Columbus, OH), from which the plasmid encoding the larvicidal toxin has been removed. The positive control was sourced from a commercially available larvicide product comprising *Bacillus thuringiensis* subspecies *israelensis*. "Media only" samples were treated with sterile NYSM media.

FIG. 2 is a bar plot of data showing the larvicidal activity of PLU6 culture against *Ae. aegypti* larvae following various treatments to the culture. The bioactive culture of PLU6 was grown for 2 days. Cell pellets and supernatants were obtained by centrifuging the whole culture for 10 minutes at 4000 rpm. Supernatants were filtered through a 0.22 μm sterile filter to obtain cell-free supernatants. Cell pellets were resuspended in fresh NYSM and applied to larvae. For heat treatments, whole cultures were heated in a heat block for the indicated time and temperature before application to larvae. Mortality was assessed 72 hours after application to larvae. Error bars represent standard deviations from at least three independent biological replicates. The positive control was sourced from a commercially available larvicide product comprising *Bacillus thuringiensis* subspecies *israelensis*. "Media only" samples were treated with sterile NYSM media.

FIG. 3 is a bar plot of data showing larvicidal activity of PLU6 culture and ATCC 29898 culture against *Ae. aegypti*. The bioactive cultures of PLU6 and ATCC 29898 were grown for 2 days. Mortality was assessed 72 hours after application to larvae. Error bars represent standard deviations from at least three independent biological replicates. "Media only" samples were treated with sterile NYSM media.

FIG. 4 shows a phylogenetic tree of 16S rRNA genes (1513 bp) from reference whole genome sequences deposited in NCBI compared to whole genome sequence of PLU6 and negative control ATCC 29898. The 16S rRNA genes were extracted post-assembly of reads using a Hidden Markov Model and aligned using MUSCLE. The phylogenetic tree was constructed using FastTree, which infers maximum-likelihood phylogenetic trees from nucleotide alignments, with a Gamma20-based likelihood under the generalized time-reversible model.

FIG. 5 shows the relationships between all sequencing runs of PLU6 and other closely related strains using a core set of proteins that are concatenated and aligned. Appendix A (SEQ ID NO: 851-1202) provides the amino acid sequences of predicted proteins present in the PLU6 strains shown in FIG. 5 (L0947, L0948, L0949, L0950, L0951, L0952, L0953, L0954, L78 and L88). The functions of the encoded proteins were predicted using Hidden Markov Modeling and the Pfam database of protein families (see, e.g., Mistry (2021) "Pfam: The protein families database in 2021", Nucleic Acids Research 49: D412-D419, incorporated herein by reference).

FIG. 6A and FIG. 6B represent a parsed output of the PLU6 16S rDNA to the same region of organisms found at NCBI and describes the most closely related organisms using a classic methodology for comparing organisms.

FIG. 7 is a bar plot of data showing the larvicidal activity of *Chryseobacterium* strains related to PLU6 ("biosimilars") isolated from environmental sources. Cultures were applied at 10% v/v. Strains M289, M290, M291, and M48 are control strains sourced from the American Type Culture Collection. M289, M290, and M291 are clones of ATCC29897 (*C. indologenes*). Strain M48 is a clone of ATCC29898 (*C. taihuense*). NYSM represents the negative control (media, no bacterial cells). Isolated Flavobacterium strains are also shown. Error bars represent standard deviations calculated from at least three independent replicates.

FIG. 8 is a bar plot of data showing the larvicidal activity of cell-free supernatants derived from *Chryseobacterium* strains biosimilar to PLU6. Cell-free culture supernatants were applied at 10% v/v. Strains M289, M290, M291, and M48 are control strains sourced from the American Type Culture Collection. M289, M290, and M291 are clones of ATCC29897 (*C. indologenes*). Strain M48 is a clone of ATCC29898 (*C. taihuense*). NYSM represents the negative control (media, no bacterial cells). Error bars represent standard deviations calculated from at least three independent biological replicates.

FIG. 9A to 9C is a whole genome phylogeny based on gene presence/absence created using PEPPAN v1.0.5. Bars represent average 72 hour mortality against *Aedes aegypti* following application with microbial cultures. Black bars represent mortality rates above 15%, and grey bars represent mortality rates below 15%.

FIG. 10A to 10D is a whole genome phylogeny based on core genes present in over 60% of strains in the analysis created using PEPPAN v1.0.5. Bars represent average 72 hour mortality against *Aedes aegypti* following application with microbial cultures. Black bars represent mortality rates above 15%, and grey bars represent mortality rates below 15%. After extracting the common ancestors for the clades in which the activity was greater than 15%, all biosimilar organisms comprised nucleotide sequences having at least 95% identity to the nucleotide sequences of PLU6 DNA gyrase subunit A, DNA topoisomerase I, DNA-directed RNA polymerase subunit beta, DNA-directed RNA polymerase subunit beta prime, DNA-directed RNA polymerase subunit alpha. Boxes numbered 1 to 6 indicate six clades of organisms (clades 1-6) having significant insecticidal killing activity against *Aedes aegypti*. A nucleotide sequence common to all members of Clade 1 is provided by SEQ ID NO: 83. Nucleotide sequences common to all members of Clade 2 are provided by SEQ ID NO: 84-157. Nucleotide sequences common to all members of Clade 3 are provided by SEQ ID NO: 158-234. Nucleotide sequences common to all members of Clade 4 are provided by SEQ ID NO: 235-464. Nucleotide sequences common to all members of Clade 5 are provided by SEQ ID NO: 465-723. Nucleotide sequences common to all members of Clade 6 are provided by SEQ ID NO: 724-850.

FIG. 11A and FIG. 11B are plots of data showing that organic extracts from supernatants of PLU6 and M82 cultures are active against *Ae. aegypti* larvae. Activity is dose-dependent and is not sensitive to heat treatment. Shown are representative dose curves for PLU6 (FIG. 11A) and M82 (FIG. 11B) extracts applied to *Ae. aegypti* larvae. Mortality data were plotted against $log_{10}$-transformed compound concentrations. Inhibitory dose-response curves were fitted using GraphPad Prism software. Error bars represent standard deviations calculated from two technical replicates (assay wells). The mean $LC_{50}$s calculated for PLU6 extract and PLU6 extract treated at 60° C. for 10 minutes were 253±11 µg/mL and 249±17 µg/mL, respectively. The mean $LC_{50}$s calculated for M82 extract and M82 extract treated at 95° C. for 10 minutes were 340±113 µg/mL and 271±227 µg/mL, respectively. Standard deviations were calculated from two independent replicate dose curves for which the curve fit R2 values were ≥0.75.

Figure 12:
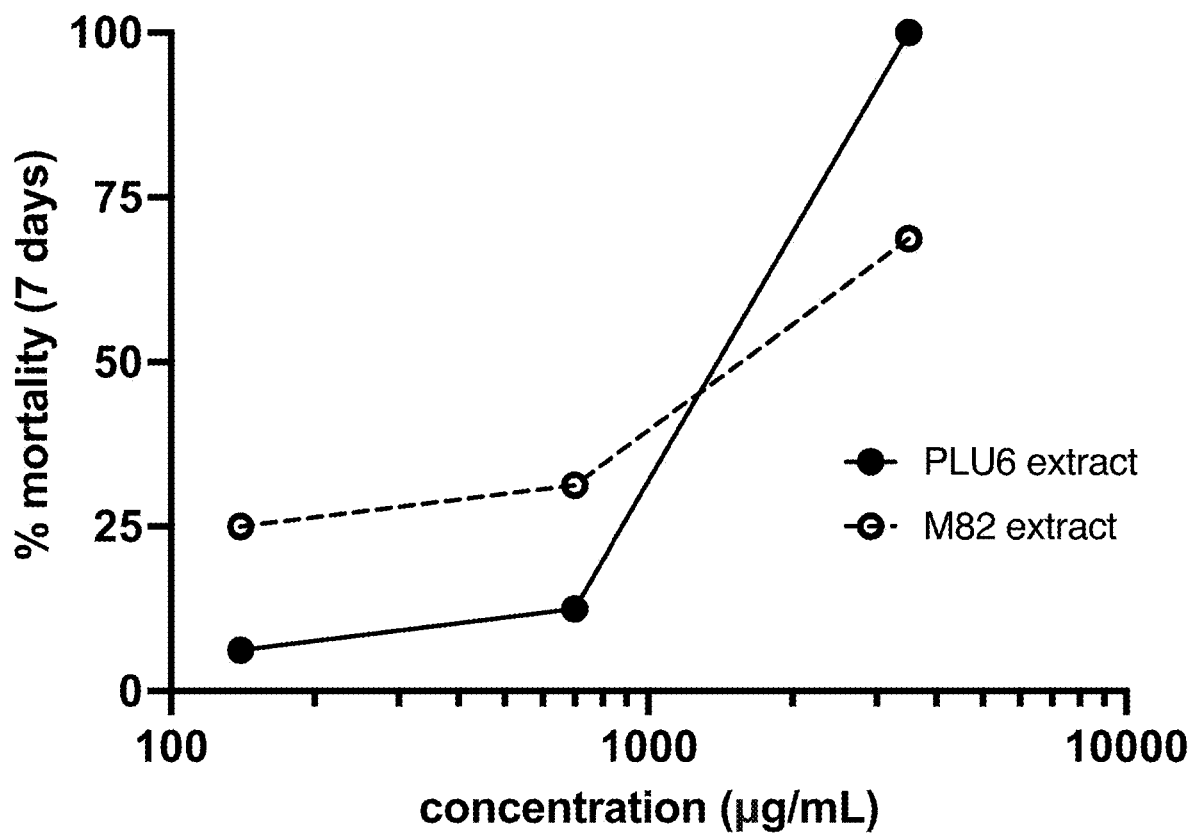

FIG. 12 is a plot of data showing that treatment with extracts prepared from *Chryseobacterium* strains causes mortality in cabbage looper (*Trichoplusia ni*) neonates. Assay used N=16 larvae per concentration. The negative controls (no extract) displayed 0% mortality.

Figure 13:
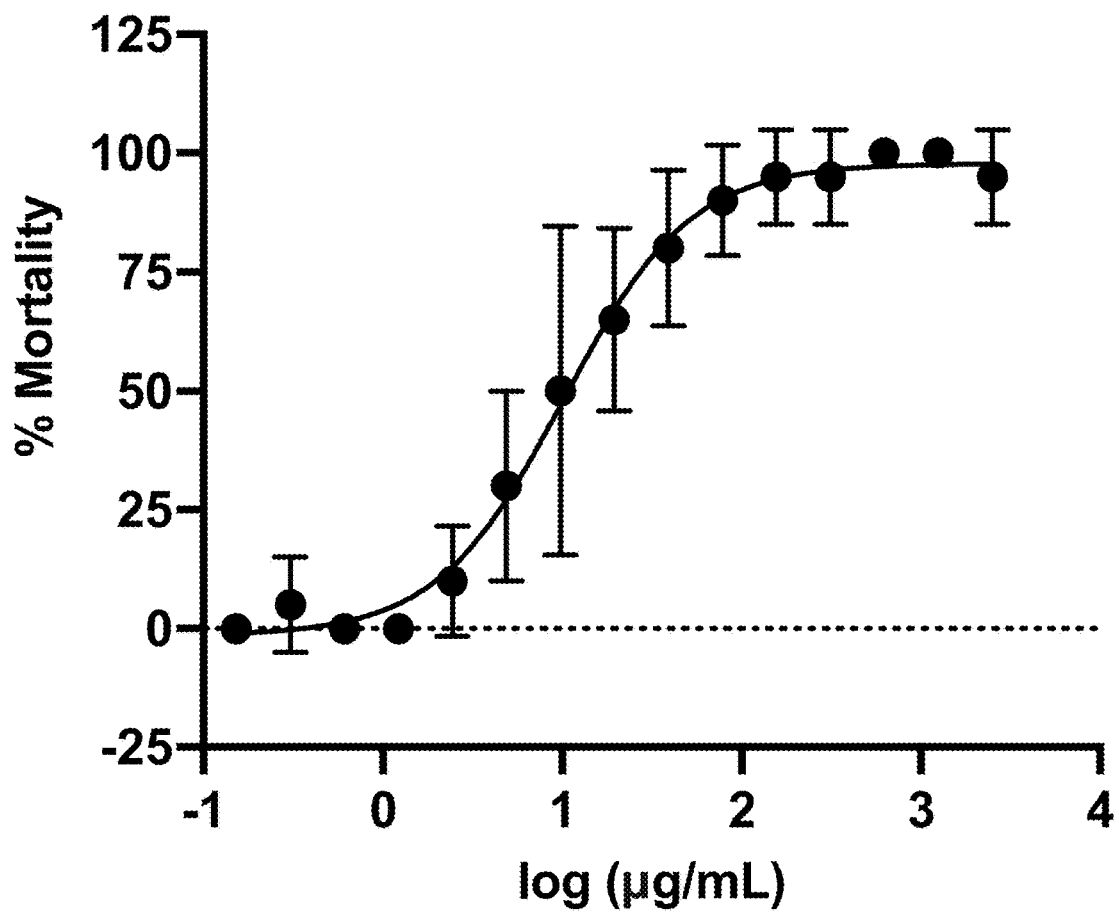

FIG. 13 is a plot of data showing that the diindole compound 3,3'-diindolylmethane produced by strain PLU6 is active against *Aedes aegypti* larvae in a dose-dependent manner. Shown is a representative dose curve for 3,3'-diindolylmethane applied to *Ae. aegypti* larvae. Mortality data were plotted against $log_{10}$-transformed compound concentrations. An inhibitory dose-response curve was fitted using GraphPad Prism software. The representative curve fit shown corresponds to a 3,3'-diindolylmethane $LC_{50}$ of 10.2 µg/mL (95% CI [7.3, 14.2]). Error bars represent standard deviations calculated from four technical replicates (assay wells). The mean $LC_{50}$ calculated for 3,3'-diindolylmethane was 7.5±3.0 µg/mL (standard deviation calculated from five independent replicate dose curves for which the curve fit $R^2$ values were ≥0.75. Significant outlier $LC_{50}$ values were identified using Grubb's test with P<0.01 and were not included in calculating the mean $LC_{50}$). Mortality in the negative control was not subtracted but was <10% for all assays.

Figure 14:
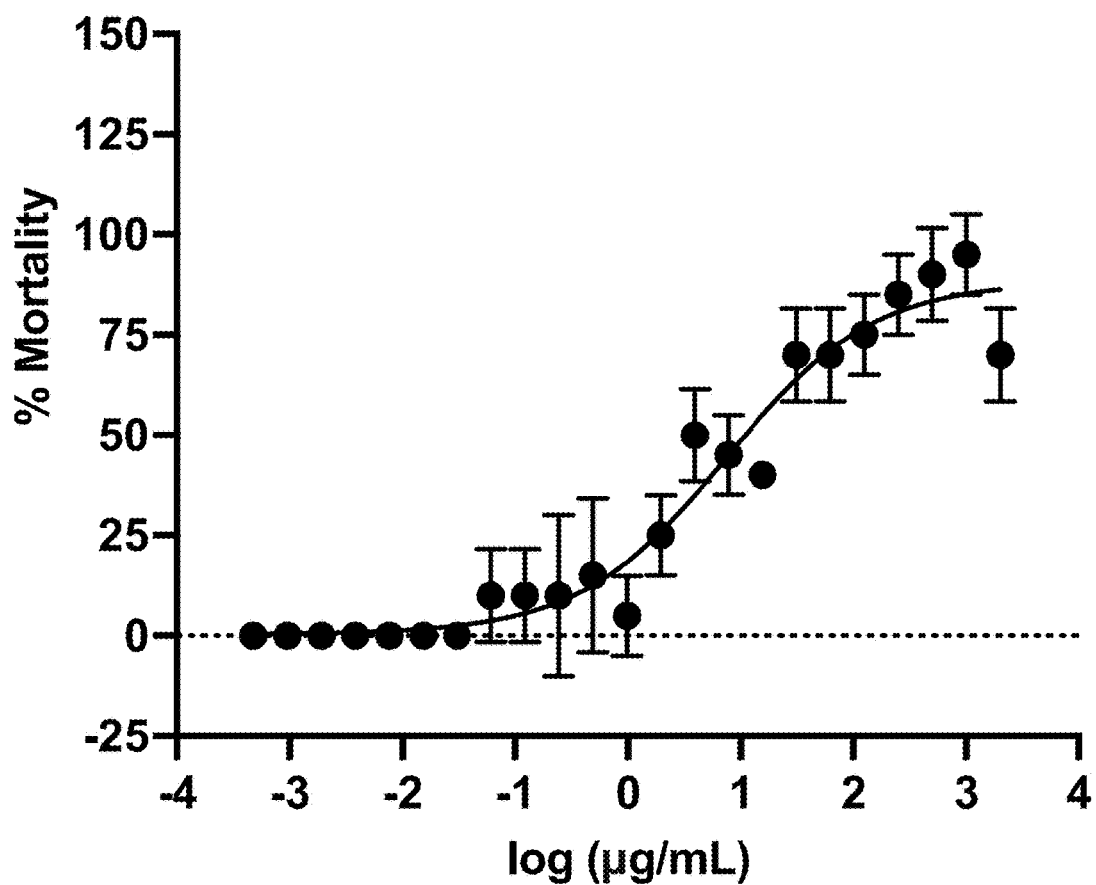

FIG. 14 is a plot showing that the diindole compound 3,3'-diindolylmethane produced by strain PLU6 is active against *Culex quinquefasciatus* larvae in a dose-dependent manner. Mortality data were plotted against $log_{10}$-transformed compound concentrations. An inhibitory dose-response curve was fitted using GraphPad Prism software. The representative curve fit shown corresponds to a 3,3'-diindolylmethane $LC_{50}$ of 7.5 µg/mL (95% CI [4.5, 13.3]). Error bars represent standard deviations calculated from four technical replicates (assay wells). Mortality in the negative control was 0%.

Figure 15:
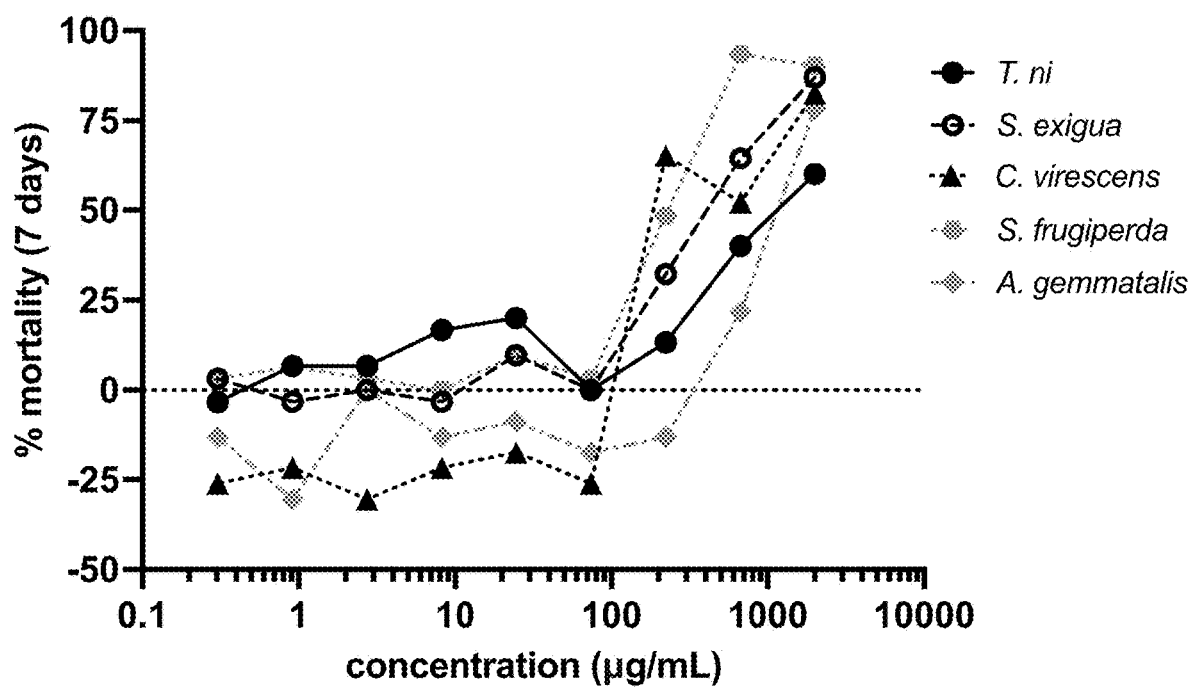

FIG. 15 is a series of plots showing that 3,3'-diindolylmethane has dose-dependent activity against five Lepidopteran species. Data presented are derived from a bioassay performed with N=32 neonates in a diet overlay format. Full species names are as follows: *Trichoplusia ni* (cabbage looper), *Spodoptera exigua* (beet armyworm), *Chloridia virescens* (tobacco budworm), *Spodoptera frugiperda* (fall armyworm), and *Anticarsia gemmatalis* (velvetbean caterpillar). Data are corrected using Abbott's Correction. Positive control samples (1000 ppm *Bacillus thuringiensis kurstaki*) produced 100% mortality for all five species.

Figure 16:
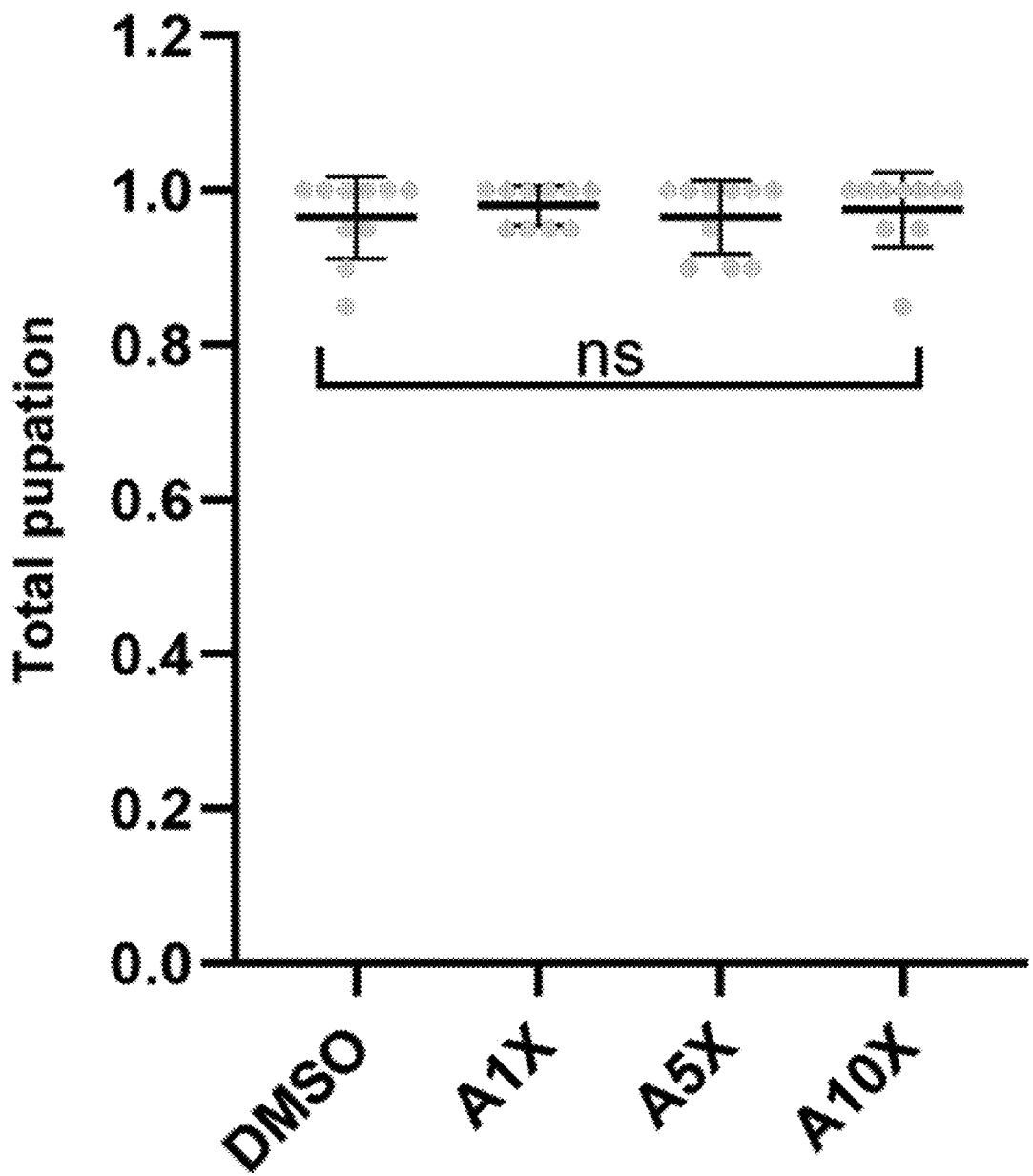

FIG. 16 is a plot of data showing that the pupation rate of *Drosophila suzukii* (spotted wing *Drosophila*) is not affected by 3,3'-diindolylmethane treatment (diet incorporation). A1X=100 μg/mL; A5X=500 μg/mL; A10X=1000 μg/mL. Each concentration was tested with 10 vials containing 20 *D. suzukii* L2 larvae. Pupation rates were not significantly different, as measured by a one-way ANOVA (alpha=0.05).

FIG. 17 is a plot of data showing that the eclosion rate of *Drosophila suzukii* (spotted wing *Drosophila*) is not affected by 3,3'-diindolylmethane treatment (diet incorporation). A1X=100 μg/mL; A5X=500 μg/mL; A10X=1000 μg/mL. Each concentration was tested with 10 vials containing 20 *D. suzukii* L2 larvae. Treatments labeled with the same letter are not significantly different, as measured by a one-way ANOVA (alpha=0.05).

FIG. 18 is a series of plots showing that the egg-to-adult survival of *Drosophila suzukii* (spotted wing *Drosophila*) is not affected by 3,3'-diindolylmethane treatment (diet incorporation). A1X=100 μg/mL; A5X=500 μg/mL; A10X=1000 μg/mL. Each concentration was tested with 10 vials containing 20 *D. suzukii* L2 larvae. "Dpi" indicates days post infestation (0 dpi is the day of egg-laying).

FIG. 19 is a plot of data showing that the synthetic diindole compound 3-((1H-indol-2-yl)methyl)-1H-indole is active against *Aedes aegypti* larvae. Shown is a representative dose curve for 3-((1H-indol-2-yl)methyl)-1H-indole applied to *Ae. aegypti* larvae. Mortality data were plotted against $\log_{10}$-transformed compound concentrations. An inhibitory dose-response curve was fitted using GraphPad Prism software. The representative curve fit shown corresponds to a 3-((1H-indol-2-yl)methyl)-1H-indole $LC_{50}$ of 5.8 μg/mL (95% CI [5.1, 6.8]). Error bars represent standard deviations calculated from four technical replicates (assay wells). The mean $LC_{50}$ calculated for 3-((1H-indol-2-yl)methyl)-1H-indole was 6.3±2.1 μg/mL (standard deviation calculated from four independent replicate dose curves for which the curve fit $R^2$ values were ≥0.75. Significant outlier $LC_{50}$ values were identified using Grubb's test with P<0.01 and were not included in calculating the mean $LC_{50}$). Mortality in the negative control was not subtracted but was <10% for all assays.

FIG. 20 is a plot of data showing that the synthetic diindole compound 3-((1H-indol-2-yl)methyl)-1H-indole is active against *Culex quinquefasciatus* larvae. Shown is a representative dose curve for 3-((1H-indol-2-yl)methyl)-1H-indole applied to *C. quinquefasciatus* larvae. Mortality data were plotted against $\log_{10}$-transformed compound concentrations. An inhibitory dose-response curve was fitted using GraphPad Prism software. The representative curve fit shown corresponds to a 3-((1H-indol-2-yl)methyl)-1H-indole $LC_{50}$ of 1.5 μg/mL (95% CI [1.3, 1.7]). Error bars represent standard deviations calculated from four technical replicates (assay wells). The mean $LC_{50}$ calculated for 3-((1H-indol-2-yl)methyl)-1H-indole was 0.95±0.75 μg/mL (standard deviation calculated from two independent replicate dose curves for which the curve fit $R^2$ values were ≥0.75. Mortality in the negative control was not subtracted but was <10% for all assays.

FIG. 21 is a plot of data showing that indole trimer (e.g., metabolite 2 or tri-indole) and tetramer (e.g., metabolite 3 or tetra-indole) compounds display no activity against *Aedes aegypti* larvae compared to diindole compounds. Error bars represent standard deviations calculated from two technical replicates (assay wells).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the terms "about", "approximately", "substantially", and "significantly" are understood by persons of ordinary skill in the art and will vary to some extent on the context in which they are used. If there are uses of these terms that are not clear to persons of ordinary skill in the art given the context in which they are used, "about" and "approximately" mean plus or minus less than or equal to 10% of the particular term and "substantially" and "significantly" mean plus or minus greater than 10% of the particular term.

As used herein, disclosure of ranges includes disclosure of all values and further divided ranges within the entire range, including endpoints and sub-ranges given for the ranges. As used herein, the disclosure of numeric ranges includes the endpoints and each intervening number therebetween with the same degree of precision. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

As used herein, the suffix "-free" refers to an embodiment of the technology that omits the feature of the base root of the word to which "-free" is appended. That is, the term "X-free" as used herein means "without X", where X is a feature of the technology omitted in the "X-free" technology. For example, a "calcium-free" composition does not comprise calcium, a "mixing-free" method does not comprise a mixing step, etc.

Although the terms "first", "second", "third", etc. may be used herein to describe various steps, elements, compositions, components, regions, layers, and/or sections, these steps, elements, compositions, components, regions, layers, and/or sections should not be limited by these terms, unless otherwise indicated. These terms are used to distinguish one step, element, composition, component, region, layer, and/or section from another step, element, composition, component, region, layer, and/or section. Terms such as "first", "second", and other numerical terms when used herein do not imply a sequence or order unless clearly indicated by the context. Thus, a first step, element, composition, component, region, layer, or section discussed herein could be termed a second step, element, composition, component, region, layer, or section without departing from technology.

As used herein, the word "presence" or "absence" (or, alternatively, "present" or "absent") is used in a relative sense to describe the amount or level of a particular entity (e.g., component, action, element). For example, when an entity is said to be "present", it means the level or amount of this entity is above a pre-determined threshold; conversely, when an entity is said to be "absent", it means the level or amount of this entity is below a pre-determined threshold. The pre-determined threshold may be the threshold for detectability associated with the particular test used to detect the entity or any other threshold. When an entity is "detected" it is "present"; when an entity is "not detected" it is "absent".

As used herein, an "increase" or a "decrease" refers to a detectable (e.g., measured) positive or negative change, respectively, in the value of a variable relative to a previously measured value of the variable, relative to a pre-established value, and/or relative to a value of a standard control. An increase is a positive change preferably at least 10%, more preferably 50%, still more preferably 2-fold, even more preferably at least 5-fold, and most preferably at least 10-fold relative to the previously measured value of the variable, the pre-established value, and/or the value of a standard control. Similarly, a decrease is a negative change preferably at least 10%, more preferably 50%, still more preferably at least 80%, and most preferably at least 90% of the previously measured value of the variable, the pre-established value, and/or the value of a standard control. Other terms indicating quantitative changes or differences, such as "more" or "less," are used herein in the same fashion as described above.

Where a term is provided in the singular, embodiments comprising the plural of that term are also provided.

As used herein, the terms "include," "includes," and "including" are to be construed as at least having the features to which they refer while not excluding any additional unspecified features.

As used herein, the term "insect" refers to any stage of an insect's life cycle (egg, larva, pupa, or adult).

As used herein, the term "egg" refers to both fertilized and unfertilized eggs.

As used herein, the phrase "an insect inhibitory amount", refers to an amount of a composition that results in any measurable inhibition of insect motility, viability, growth, insect development, insect reproduction, insect egg laying, insect feeding behavior, insect mating behavior, and/or any measurable decrease in the adverse effects caused by insect feeding, egg laying or other interaction with a plant.

As used herein, the term "heterologous" refers to any element (e.g., a microorganism or any component thereof) that is in a context other than that which it occurs in nature.

As used herein, the term "heterologous" when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with endogenous gene sequences in the chromosome, or are associated with portions of the chromosome not found in nature (e.g., genes expressed in loci where the gene is not normally expressed).

As used herein, the term "host cell" refers to any cell capable of replicating and/or transcribing and/or translating a heterologous gene. Thus, a "host cell" refers to any eukaryotic or prokaryotic cell (e.g., plant cells, algal cells such as C. reinhardtii, bacterial cells such as yeast cells, E. coli, insect cells, etc.), whether located in vitro or in vivo. For example, a host cell may be located in a transgenic plant or located in a plant part or part of a plant tissue or in cell culture. In some embodiments, a host cell is a "heterologous host cell". As used herein, a "heterologous host cell" is a cell comprising a heterologous gene, e.g., a gene from an organism that is different than the heterologous host cell.

As used herein, the term "transgenic" when used in reference to a plant or leaf or fruit or seed, e.g., a "transgenic plant," transgenic leaf," "transgenic fruit," "transgenic seed," or a "transgenic host cell", refers to a plant or leaf or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

As used herein, the term "plant" is used in its broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera. Transgenic plants may be produced using techniques known in the art.

The terms "protein," "polypeptide," "peptide," "encoded product," "amino acid sequence," are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. The term "X" may represent any amino acid.

The term "sequence identity" means that two polynucleotide or two polypeptide sequences are identical (i.e., on a nucleotide-by-nucleotide basis or amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) or amino acid, in which often conserved amino acids are taken into account, occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA.

As used herein, a "system" refers to a plurality of real and/or abstract components operating together for a common purpose. In some embodiments, a "system" is an integrated assemblage of hardware and/or software components. In some embodiments, each component of the system interacts with one or more other components and/or is related to one or more other components. In some embodiments, a system refers to a combination of components and software for controlling and directing methods. For example, a "system" or "subsystem" may comprise one or more of, or any combination of, the following: mechanical devices, hardware, components of hardware, circuits, circuitry, logic design, logical components, software, software modules, components of software or software modules, software procedures, software instructions, software routines, software objects, software functions, software classes, software programs, files containing software, etc., to perform a function of the system or subsystem. Thus, the methods and apparatus of the embodiments, or certain aspects or portions thereof, may take the form of program code (e.g., instructions) embodied in tangible media, such as floppy diskettes, CD-ROMs, hard drives, flash memory, or any other machine-readable storage medium wherein, when the program code is loaded into and executed by a machine, such as a computer, the machine becomes an apparatus for practicing the embodiments. In the case of program code execution on programmable computers, the computing device generally includes a processor, a storage medium readable by the processor (e.g., volatile and non-volatile memory and/or storage elements), at least one input device, and at least one output device. One or more programs may implement or utilize the processes described in connection with the embodiments, e.g., through the use of an application programming interface (API), reusable controls, or the like. Such programs are preferably implemented in a high-level procedural or object-oriented programming language to communicate with a computer system. However, the program(s) can be implemented in assembly or machine language, if desired. In any case, the language may be a compiled or interpreted language, and combined with hardware implementations.

As used herein, the term "biological system" refers to a collection of genes, enzymes, activities, or functions that operate together to provide a metabolic pathway or metabolic network. A biological system may also be described in terms of nutrient flux, energy flux, electrochemical gradients, metabolic inputs (biological reactants), and metabolic outputs (biological products), e.g., that provide for conversion of energy inputs into energy for biological processes, anabolic synthesis of biomolecules, and elimination of wastes.

As used herein, the term "metabolic pathway" refers to a set of connected metabolic, biochemical, and physical processes that transform a metabolic input to a metabolic output in a series of steps and intermediates.

As used herein, the term "metabolic network" refers to a set of connected metabolic pathways. A metabolic network may transform a metabolic input to a metabolic output in a series of steps and intermediates.

As used herein, the terms "microbial", "microbial organism", and "microorganism" refer to an organism that exists as a microscopic cell that is included within the domains of Archaea, Bacteria, or Eukarya in the three-domain system (see Woese (1990) Proc Natl Acad Sci USA 87: 4576-79, incorporated herein by reference), the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical. The terms "microbial cells" and "microbes" are used interchangeably with the term "microorganism". The terms "bacteria" and "bacterium" and "archaea" and "archaeon" refer to prokaryotic organisms of the domain Bacteria and Archaea in the three-domain system.

The term "Archaea" refers to a taxonomic domain of organisms typically found in unusual environments and distinguished from the rest of the prokaryotes by several criteria, including the number of ribosomal proteins and the lack of muramic acid in cell walls. On the basis of small subunit rRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophiles (prokaryotes that live at very high temperatures). Besides the unifying archaeal features that distinguish them from Bacteria (e.g., no murein in cell wall, ester-linked membrane lipids, etc.), these prokaryotes exhibit unique structural or biochemical attributes which adapt them to their particular habitats. The Crenarchaeota consist mainly of hyperthermophilic sulfur-dependent prokaryotes and the Euryarchaeota contain the methanogens and extreme halophiles.

The term "Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus*, Clostridia, *Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) Thermotoga and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

As used herein, the term "genus" is defined as a taxonomic group of related species according to the Taxonomic Outline of Bacteria and Archaea (Garrity et al. (2007) The Taxonomic Outline of Bacteria and Archaea. TOBA Release 7.7, March 2007. Michigan State University Board of Trustees).

As used herein, the term "species" is defined as a collection of closely related organisms with greater than 97% 16S ribosomal RNA sequence homology and greater than 70% genomic hybridization and sufficiently different from all other organisms so as to be recognized as a distinct unit.

As used herein, the term "strain" as used herein in reference to a microorganism describes an isolate of a microorganism considered to be of the same species but with a unique genome and, if nucleotide changes are non-synonymous, a unique proteome differing from other strains of the same organism. Strains may differ in their non-chromosomal genetic complement. Typically, strains are the result of isolation from a different host or at a different location and time, but multiple strains of the same organism may be isolated from the same host.

As used herein, the term "naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

As used herein, the term "non-naturally occurring" as applied to a nucleic acid, an enzyme, a cell, or an organism refers to a nucleic acid, an enzyme, a cell, or an organism that has at least one genetic alteration not normally found in the naturally occurring nucleic acid, enzyme, cell, or organism. Genetic alterations include, for example, modifications introducing expressible nucleic acids encoding metabolic polypeptides, other nucleic acid additions, nucleic acid deletions, and/or other functional disruption of the microbial genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon.

As used herein, the term "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reactions that occur within a natural environment.

As used herein, the term "cell culture" refers to any in vitro culture of cells, including, e.g., prokaryotic cells and eukaryotic cells. Included within this term are continuous cell lines, primary cell cultures, transformed cell lines, finite cell lines (e.g., non-transformed cells), bacterial or archaeal cultures in or on solid or liquid media, and any other cell population maintained in vitro.

As used herein, the term "culturable organism" refers to a living organism that can be maintained and grown in a laboratory. In some embodiments, a culturable organism may not be maintained and grown in a laboratory in a pure culture free of other organisms and so may be referred to as an "unculturable organism" with respect to growing as a pure culture. However, in some embodiments, such an organism may be grown in a laboratory in a microbial consortium comprising at least one other organism and so may be a "culturable organism" with respect to the consortium and be also an "unculturable organism" with respect to being grown in a pure culture without the other member(s) of the consortium.

As used herein, "isolate", "isolated", "isolated microbe", and like terms are intended to mean that the one or more microorganisms has been separated from at least one of the materials with which it is associated in a particular environment (for example, soil, water, or a higher multicellular organism). Thus, an "isolated microbe" does not exist in its naturally occurring environment; rather, through the various techniques described herein, the microbe has been removed from its natural setting and placed into a non-naturally occurring state of existence. Thus, the isolated strain may exist as, for example, a biologically pure culture, or as spores (or other forms of the strain) in association with a carrier composition. In certain aspects of the disclosure, the isolated microbes exist as isolated and biologically pure cultures. It will be appreciated by one of skill in the art that an isolated and biologically pure culture of a particular microbe denotes that said culture is substantially free (within scientific reason) of other living organisms and contains only the individual microbe in question. The culture can contain varying concentrations of said microbe, and isolated and biologically pure microbes often necessarily differ from less pure or impure materials. Furthermore, in some aspects, the disclosure provides for certain quantitative measures of the concentration, or purity limitations, that are found within an isolated and biologically pure microbial culture. The presence of these purity values, in certain embodiments, is a further attribute that distinguishes the presently disclosed microbes from those microbes existing in a natural state.

As used herein, "genome" refers to the genetic material (e.g., chromosome) of an organism.

As used herein, the term "gene" refers to a nucleic acid molecule that comprises a nucleic acid sequence that encodes a polypeptide or non-coding RNA and the expression control sequences that are operably linked to the nucleic acid sequence that encodes the polypeptide or non-coding RNA. For instance, a gene may comprise a promoter, one or more enhancers, a nucleic acid sequence that encodes a polypeptide or a non-coding RNA, downstream regulatory sequences and, possibly, other nucleic acid sequences involved in regulating the transcription of an RNA from the gene.

As used herein, the term "genetic basis" refers to the underlying genetic or genomic cause of a particular observation.

As used herein, the term "genetic" refers to the heritable information encoded in the sequence of DNA nucleotides. As such, the term "genetic characterization" is intended to mean the sequencing, genotyping, comparison, mapping, or other assay of information encoded in DNA.

As used herein, the term "genetic material" refers to the DNA within an organism that is passed along from one generation to the next. Normally, genetic material refers to the genome of an organism. Extra-chromosomal elements, such as organelle or plasmid DNA, can also be a part of the genetic material that determines organism properties.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

The term "homolog" as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

As used herein, the term "taxonomic unit" is a group of organisms that are considered similar enough to be treated as a separate unit. A taxonomic unit may comprise a family, genus, species, or population within a species (e.g., strain), but is not limited as such.

As used herein, the term "operational taxonomic unit" (OTU) refers to a group of microorganisms considered similar enough to be treated as a separate unit. An OTU may comprise a taxonomic family, genus, or species but is not limited as such. OTUs are frequently defined by comparing nucleotide sequences between organisms. In certain cases, the OTU may include a group of microorganisms treated as a unit based on, e.g., a sequence identity of ≥97%, ≥95%, ≥90%, ≥80%, or ≥70% among at least a portion of a differentiating biomarker, such as the 16S rRNA gene.

As used herein, "environmental sample" means a sample taken or acquired from any part of the environment (e.g., ecosystem, ecological niche, habitat, etc.) An environmental sample may include liquid samples from a river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Provided herein are insect inhibitory compositions comprising certain *Chryseobacterium* strains, plant parts treated with the compositions, methods of using the compositions to control insects, and methods of making the compositions. Insect inhibitory compositions provided herein provide for inhibition of insect viability, insect growth, insect development, insect reproduction, insect egg laying, insect feeding behavior, insect mating behavior and/or any measurable decrease in the adverse effects caused by insect (e.g., damage to a plant including reductions in yield, fruit quality, and the like; numbers of insects present in a sample, numbers of insects carrying viruses and/or parasites). In certain embodiments, such insect inhibitory activity of the compositions is increased in comparison to untreated controls and/or controls comprising a mock composition lacking insect inhibitory microorganisms and/or compounds. In certain embodiments, such insect inhibitory activity of the compositions is increased against insects that have acquired resistance to other insect inhibitory microorganisms and/or compounds with distinct modes-of-action in comparison to untreated control compositions, controls treated with a mock composition lacking insect inhibitory microorganisms and/or compounds, and/or control compositions comprising other insect inhibitory microorganisms and/or compounds with distinct modes-of-action.

*Chryseobacterium* strains that can be used in the compositions, plant parts, and methods provided herein include strains characterized by the presence of particular genes. In certain embodiments, the *Chryseobacterium* strain can comprise: (a) at least one gene and/or coding region encoding a protein with at least 95%, 96%, 97%, 98%, 99%, 99.5%, 99.8%, 99.9%, or 100% sequence identity across the entire length of SEQ ID NO: 1 (MKCIGJBJ_03627 DNA gyrase subunit A), at least 95%, 96%, 97%, 98%, 99%, 99.5%, 99.8%, 99.9%, or 100% sequence identity across the entire length of SEQ ID NO: 2 (MKCIGJBJ_03079 DNA topoisomerase 1), at least 95%, 96%, 97%, 98%, 99%, 99.5%, 99.8%, 99.9%, or 100% sequence identity across the entire length of SEQ ID NO: 3 (MKCIGJBJ_00500 DNA-directed RNA polymerase subunit beta), at least 95%, 96%, 97%, 98%, 99%, 99.5%, 99.8%, 99.9%, or 100% sequence identity across the entire length of SEQ ID NO: 4 (MKCIGJBJ_00499 DNA-directed RNA polymerase subunit beta'), and/or at least 95%, 96%, 97%, 98%, 99%, 99.5%, 99.8%, 99.9%, or 100% sequence identity across the entire length of SEQ ID NO: 5 (MKCIGJBJ_02095 DNA-directed RNA polymerase subunit alpha; (b) at least one gene and/or coding region encoding a protein with at least 95%, 96%, 97%, 98%, 99%, 99.5%, 99.8%, 99.9%, or 100% sequence identity across the entire length of a sequence contained in Appendix A (PLU6_1-PLU6_352; SEQ ID NO: 851-1202); or (c) any combination of gene and/or coding regions of (a) and/or genes and/or coding regions of (b).

In certain embodiments, the *Chryseobacterium* strain can comprise: (a) at least one gene comprising a sequence with at least 80%, 90%, 95%, 98%, 99%, 99.5%, 99.8%, 99.9%, or 100% sequence identity across the entire length of a gene described above wherein the gene sequence can be found within SEQ ID NO: 77, or found within or comprises or consists of SEQ ID NOs: 6-76.

Any of the aforementioned *Chryseobacterium* strains that can be used in the compositions and methods provided herein are hereinafter referred to as "PLU6-type" strains, "PLU6-type" bacteria, "PLU6-type" monocultures, and the like. In certain embodiments, the compositions will comprise PLU6-type bacteria at a concentration of least $1\times10^6$, $2\times10^6$, $5\times10^6$, $1\times10^7$, $2\times10^7$, $5\times10^7$, $1\times10^8$, $2\times10^8$, or $5\times10^8$ colony forming units (CFU) per milliliter of the composition or at a titer of at least $1\times10^6$, $2\times10^6$, $5\times10^6$, $1\times10^7$, $2\times10^7$, $5\times10^7$, $1\times10^8$, $2\times10^8$, or $5\times10^8$ colony forming units (CFU) per gram of the composition. In certain embodiments, the compositions will comprise PLU6-type bacteria at a concentration of $1\times10^6$, $2\times10^6$, $5\times10^6$, $1\times10^7$, or $2\times10^7$ to about $5\times10^7$, $1\times10^8$, $2\times10^8$, or $5\times10^8$ colony forming units (CFU) per milliliter of the composition or at a titer of $1\times10^6$, $2\times10^6$, $5\times10^6$, $1\times10^7$, or $2\times10^7$ to about $5\times10^7$, $1\times10^8$, $2\times10^8$, or $5\times10^8$ colony forming units (CFU) per gram of the composition. A representative PLU6-type strain, PLU6, that can be used in the compositions, plant parts, and methods provided herein was deposited with the AMERICAN TYPE CULTURE COLLECTION (ATCC) under the terms of the Budapest Treaty on the International Recognition of the Deposit of Microorganisms for the Purposes of Patent Procedure. The above deposit was made on May 18, 2021, pursuant to the terms of the Budapest Treaty, and is intended to meet the requirements of 37 CFR § 1.801-1.809. The deposit was made under Patent Deposit Number PTA-127072. Access to the deposits will be available upon request during the pendency of the application to the Commissioner of Patents and Trademarks and persons determined by the Commissioner to be entitled thereto. All restrictions upon availability to the public will be irrevocably removed upon granting of the patent. The deposit will be maintained in the CECT Depository, which is a public depository, for a period of 30 years, or 5 years after the most recent request, or for the enforceable life of the patent, whichever is longer. The viability of the deposit will be tested and will be replaced if it becomes nonviable during that period. Upon allowance of any claims in the application, Applicant will maintain and will make this deposit available to the public, pursuant to the Budapest Treaty.

Variants and/or progeny of the deposited strain PLU6 (ATCC Patent Deposit Number PTA-127072) comprising any of the aforementioned genes and/or provided at any of the aforementioned concentrations can also be used in the compositions, plant parts, and methods provided herein. Such variants can be obtained by genetic transformation or gene-editing (e.g., CRISPR-Cas9 editing) of the deposited strain PLU6 (ATCC Patent Deposit Number PTA-127072). Methods for editing PLU6 can be adapted from methods disclosed for editing bacterial genomes (e.g., Altenbuchner, J., Appl Environ Microbiol. 2016, 82(17):5421-7. doi: 10.1128/AEM.01453-16). Such progeny can be obtained by culturing the deposited strain PLU6 (ATCC Patent Deposit Number PTA-127072) or by isolation of progeny from products containing or treated with the PLU6 strain (e.g., compositions comprising PLU6, plants or plant parts treated with PLU6, environmental samples treated with PLU6 including soil, water, and the like).

Insects inhibited by the aforementioned compositions include Dipteran insects (e.g. *Aedes* sp., *Anopheles* sp., *Culex* sp., *Ceratitis* sp., a *Delia* sp., *Mayetolia* sp., *Rhagoletis* sp., *Anastrepha* sp. a *Glossina* sp., a *Musca* sp., *Cochliomyia* sp., *Chrysops* sp., *Simulium* sp., *Phlebotomus* sp., *Culicoides* sp., or *Dermatobia* sp.).

Methods for identifying PLU6-type bacteria, as well as compositions, environmental samples (e.g., water, soil, and the like), and plant parts comprising and/or treated with such bacteria are also provided herein. In certain embodiments, the PLU6-type bacteria can be detected by detecting a protein or ortholog thereof having at least 95%, 96%, 97%, 98%, 99%, 99.5%, 99.8%, 99.9%, or 100% sequence identity across the entire length of SEQ ID NO: 1-5 and/or a sequence contained in Appendix A (PLU6_1-PLU6_352; SEQ ID NO: 851-1202). Such proteins can be detected by methods including immunological-based detection and/or mass-spectrometry based detection. In certain embodiments, the PLU6-type bacteria can be detected by detecting a gene or ortholog thereof having at least 80%, 90%, 95%, 96%, 97%, 98%, 99%, 99.5%, 99.8%, 99.9%, or 100% sequence identity across the entire length of a PLU6 gene as described herein. Such genes can be detected by methods including hybridization-based, PCR-based, chain elongation-based, nanopore-based, sequencing-based, and/or mass spectrometry-based nucleic acid detection methods.

PLU6-type monocultures used in the compositions, plant parts, and methods as well as cultures or harvested PLU6-type monocultures provided herein include embodiments that are essentially free of contaminating organisms. Such contaminating microorganisms are microorganisms other than the desired PLU6-type strain of the monoculture. In certain embodiments, the contaminating microorganisms are of an indeterminate origin and arise through inadvertent infection of the PLU6-type monocultures. In certain embodiments, the compositions or cultures comprising the harvested PLU6-type monocultures that are essentially free of contaminating microorganisms comprise less than about 5%, 3%, 2%, 1%, 0.5%, 0.2%, or 0.1% by mass, colony forming units, or metagenomic analysis contaminating microorganisms other than the desired PLU6-type strain of the monoculture. In certain embodiments, compositions useful in the practice of the methods of inhibiting insects provided herein do not need to be entirely free of contaminating microorganisms. In certain embodiments where compositions for use as insect inhibitory agents are formulated under non-aseptic conditions, it is anticipated that some levels of contaminating microorganisms (e.g., less than about 5%, 3%, 2%, 1%, 0.5%, 0.2%, or 0.1% by mass, colony forming units, or metagenomic analysis) can be present without reducing the insect inhibitory activity of the composition to unacceptable levels. In certain embodiments, the compositions, cultures, or harvested PLU6-type strains that are free of contaminating microorganisms comprise 0% by mass, colony forming units, or metagenomic analysis contaminating microorganisms other than the desired PLU6-type strains. Methods for assessing contamination by metagenome analysis can be adapted from various disclosed methods for use in assessing contamination of laboratory reagents (e.g., Salter et al., BMC Biology, 2014, 12:87 (doi.org/10.1186/s12915-014-0087-z)).

Monocultures of the desired PLU6-type strains that are essentially free of contaminating organisms can be obtained by culturing an uncontaminated isolate of the strain under axenic conditions. Such axenic conditions can be achieved by sterilizing culture media by methods that include heat and pressure treatment (e.g., in an autoclave), filtration (e.g., in a filter having a pore size of 0.45 micrometers or less), irradiation, plasma treatment, and any combination of such techniques.

In certain embodiments, compositions comprising the PLU6-type strains can further comprise additional desirable microorganisms or viruses. Such desirable microorganisms or viruses include: (a) microorganisms that inhibit the same insect pest or class of insect pests as the PLU6-type strains by a different mode-of-action; (b) microorganisms or viruses that inhibit wholly distinct insect pests or classes of insect pests (e.g., Coleopteran, Lepidopteran, and/or Hymenopteran insect pests) or other plant pathogenic or pathogenic bacteria, fungi, or nematodes; and/or (c) microorganisms that improve plant yield (e.g., nitrogen-fixing bacteria such as *Rhizobium* or *Bradyrhizobium*). Microorganisms or viruses that inhibit the same insect pest or class of insect pests as the PLU6-type strains by a different mode-of-action; (b) microorganisms that inhibit wholly distinct insect pests or classes of insect pests (e.g., Coleopteran, Lepidopteran, and/or Hymenopteran insect pests) or other plant pathogenic or pathogenic bacteria, fungi, or nematodes include various microorganisms disclosed in US Patent Application publication US20180049435, which is incorporated herein by reference in its entirety. Useful microorganisms or viruses with insecticidal, acaricidal, molluscidal and/or nematicidal activity include *Agrobacterium radiobacter*, *Bacillus* sp., (e.g., *B. cereus*, *B. firmus*, *B. thuringiensis*, *B. thuringiensis* ssp. *aizawai*, *B. t.* ssp. *israelensis*, *B. t.* ssp. *galleriae*, *B. t.* ssp. *kurstaki*, *B. t.* ssp. *tenebriones*), *Beauveria bassiana*, *B. brongniartii*, *Burkholderia* sp., *Chromobacterium subtsugae*, *Cydia pomonella granulovirus* (CpGV), *Cryptophlebia leucotreta granulovirus* (CrleGV), *Flavobacterium* sp., *Helicoverpa armigera nucleopolyhedrovirus* (HearNPV), *Helicoverpa zea nucleopolyhedrovirus* (HzNPV), *Helicoverpa zea* single capsid nucleopolyhedrovirus (HzSNPV), *Heterorhabditis bacteriophora*, *Isaria fumosorosea*, *Lecanicillium longisporum*, *L. muscarium*, *Metarhizium anisopliae*, *Metarhizium anisopliae* var. *anisopliae*, *M anisopliae* var. *acridum*, *Nomuraea rileyi*, *Paecilomyces fumosoroseus*, *P. lilacinus*, *Paenibacillus popilliae*, *Pasteuria* sp., *P. nishizawae*, *P. penetrans*, *P. ramosa*, *P. thornea*, *P. usgae*, *Pseudomonas fluorescens*, *Spodoptera littoralis nucleopolyhedrovirus* (SpliNPV), *Steinernema carpocapsae*, *S. feltiae*, *S. kraussei*, *Streptomyces galbus*, and *S. microjlavus*. Useful microorganisms or viruses with fungicidal, bactericidal, viricidal and/or plant defense activator activity that can be combined with the PLU6-type strains include *Ampelomyces quisqualis*, *Aspergillus flavus*, *Aureobasidium pullulans*, *Bacillus* sp. (e.g. *B. altitudinis*, *B. amyloliquefaciens*, *B. megaterium*, *B. mojavensis*, *B. mycoides*, *B. simplex*, *B. solisalsi*, *B. subtilis*, *B. subtilis* var. *amyloliquefaciens*), *Candida oleophiia*, *C. saitoana*, *Clavibacter michiganensis* (bacteriophages), *Coniothyrium minitans*, *Cryphonectria parasitica*, *Cryptococcus albidus*, *Dilophosphora alopecuri*, *Fusarium oxysporum*, *Clonostachys rosea* f. *catenulate* (also named *Gliocladium catenulatum*), *Gliocladium roseum*, *Lysobacter antibioticus*, *L. enzymogenes*, *Metschnikowia fructicola*, *Microdochium dimerum*, *Microsphaeropsis ochracea*, *Muscodor albus*, *Paenibacillus alvei*, *Paenibacillus polymyxa*, *Pantoea vagans*, *Penicillium bilaiae*, *P. steckii*, *Phlebiopsis gigantea*, *Pseudomonas* sp.,

*Pseudomonas chloraphis, Pseudozyma jlocculosa, Pichia anomala, Pythium oligandrum, Sphaerodes mycoparasitica, Streptomyces griseoviridis, S. lydicus, S. violaceusniger, Talaromyces jlavus, Trichoderma asperelloides, T. asperellum, T. atroviride, T. fertile, T. gamsii, T. harmatum, T. harzianum, T. polysporum, T. stromaticum, T. vixens, T. viride, Typhula phacorrhiza, Ulocladium oudemansii*, and *Verticillium dahlia*. In certain embodiments, useful microorganisms or viruses with activity against Dipteran insects (e.g., *Aedes* sp., *Culex* sp., or *Anopheles* sp. *Mosquitos*, a *Ceratitis* sp., *Delia* sp., a *Glossina* sp., a *Musca* sp., *Cochliomyia* sp., *Chrysops* sp., *Simulium* sp., *Phlebotomus* sp., *Culicoides* sp., or *Dermatobia* sp.) are combined with the PLU6-type strains. In certain embodiments, PLU6-type strains are combined with a Dipteran active *Bacillus thuringiensis* (B. t) strain (e.g. B. t. subsp. *israelensis* (Bti) and/or a *Lysinibacillus sphaericus* (Ls) strain. In certain embodiments, PLU6-type strains are combined with a dipteran active *Bacillus thuringiensis* (B.t) strain which expresses a Cry1Ab, Cry1Ca, Cry2Aa, Cry4Aa, Cry4Ba, Cry11 Aa, Cry11B, Cry16A, Cyt1Aa, and/or Cyt2Aa protein. In certain embodiments, PLU6-type strains are combined with a dipteran active *C. bifermentans* subsp. *malaysia* strains expressing a dipteran insect inhibiting Cry 17A, Cry 18A, and/or Cry 19A protein. Microorganisms that express dipteran active toxins are disclosed in Schnepf, et al. Microb. Molec. Biol Rev. 1998; 62(3):775-806, at 791. In certain embodiments, the PLU6-type strains are combined with a Dipteran active *B. sphaericus* strains, including those expressing a binary toxin. Useful Dipteran active *B. sphaericus* strains that can be combined with the PLU6-type strains include the binary toxin expressing strains that have been disclosed, variants thereof, and related *B. sphaericus* strains (Porter et al. Microbiological Reviews, 1993, 57(4): 838-861).

In certain embodiments, compositions comprising the PLU6-type strains can further comprise insect inhibitory compounds. Insect inhibitory compounds that can be combined with the PLU6-type strains include organophosphate, pyrethroid, carbamate, chlorinated hydrocarbon, pyrethroid, spinosyn, spinosoid, nicotinoid, pyrazole, or pyrrole insecticides.

Compositions provided herein can include certain adjuvants and/or excipients. Such adjuvants are components added to the composition that can preserve and/or potentiate the insect inhibitory activity of the PLU6-type strains. Contemplated adjuvants include those that are naturally occurring and those that are non-naturally occurring. Broad categories of adjuvants that can be used include agents that promote distribution or retention of the composition or insect inhibitory activity of the composition onto or within a treatment target (e.g., standing water, soil, and/or a plant part). Surfactants that can be used as adjuvants include anionic, cationic, nonionic and amphoteric surfactants, block polymers, polyelectrolytes, and mixtures thereof. Such surfactants can serve as an emulsifier, dispersant, solubilizer, wetter, penetration enhancer, and/or protective colloid in compositions comprising the PLU6-type bacteria or monocultures provided herein. Anionic surfactants that can be used include alkali, alkaline earth or ammonium salts of sulfonates (e.g., alkylarylsulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates, sulfosuccinamate-sulfates, or combinations thereof), sulfates (e.g., sulfates of fatty acids and oils, of ethoxylated alkylphenols, of alcohols, of ethoxylated alcohols, or of fatty acid esters), phosphates (e.g., phosphate esters), carboxylates (e.g. alkyl carboxylates, carboxylated alcohol ethoxylates, or carboxylated alkylphenol ethoxylates), and mixtures thereof. Other useful adjuvants include sticking agents (e.g., binders or tackifiers) particularly in embodiments where the composition is for application to a plant part (e.g., foliage, seed, roots, and the like) or soil. Sticking agents include polyvinylpyrrolidones, polyvinylacetates, polyvinyl alcohols, polyacrylates, biological or synthetic waxes, and cellulose ethers.

Other categories of adjuvants include components that increase shelf-life of the composition comprising the PLU6-type bacteria and/or whole cultures thereof (e.g., PLU6-type bacteria and fermentation broth). In certain embodiments, the shelf-life is extended by including desiccants and/or other agents that provide for maintaining the composition in a state that is essentially free of water. Such compositions that are essentially free of water include those with a water content of less than about 1%, 0.5%, 0.2%, or 0.1% by weight. In certain embodiments, the water content of a composition that is essentially free of water is about 1%, 0.5%, or 0.2% to about 0.1%, 0.05%, 0.02%, or 0.01% by weight. In certain embodiments, the compositions, including those that are essentially free of water, can include a lyophilized (i.e., freeze-dried) PLU6-type bacteria. Useful adjuvants used in such compositions comprising lyophilized PLU6-type bacterial cultures include various cryoprotectants (e.g., disaccharides such as sucrose, trehalose, proteins such as Bovine Serum Albumin and the like, glycine betaine, and combinations thereof).

Compositions comprising the PLU6-type bacteria provided herein can include certain excipients. In certain embodiments, such excipients are components added to the composition that are essentially inert and serve as bulking agents. In certain embodiments, a component of the composition can serve an excipient and an adjuvant. Examples of excipients used herein include mineral earths (e.g., silicates, silica gels, talc, kaolins, limestone, lime, chalk, clays, dolomite, diatomaceous earth, bentonite, calcium sulfate, magnesium sulfate, magnesium oxide), polysaccharides (e.g., cellulose, starch); and various plant products (e.g., bagasse, wood chips, or any other lignocellulosic biomass) and mixtures of any of the foregoing materials.

In certain embodiments, compositions comprising the PLU6-type bacteria can be an aqueous liquid, a non-aqueous liquid, or an emulsion comprising an aqueous and an immiscible and/or partially miscible non-aqueous liquid. Non-aqueous liquids that are used alone or in emulsions include mineral oils (e.g., kerosene and/or diesel oil); animal oils, plant oils (e.g., corn, soy, castor, rapeseed and/or any other oilseed oil, and the like); aliphatic, cyclic and aromatic hydrocarbons (e.g., toluene, paraffin, tetrahydronaphthalene, and/or alkylated naphthalenes); alcohols (e.g., propanol, butanol, benzylalcohol, and/or cyclo-hexanol); glycols; dimethyl sulfoxide (DMSO); ketones (e.g., cyclohexanone; esters (e.g., lactates, carbonates, fatty acid esters, gamma-butyrolactone); saturated and/or unsaturated fatty acids (e.g., stearic, palmitic, linolenic, linoleic, oleic, and the like); phosphonates; amines; amides (e.g., N-methylpyrrolidone, fatty acid dimethylamides); and mixtures of any of the foregoing materials. In certain embodiments, the emulsion can contain an emulsion stabilizer (e.g., any amphipathic of other agent which promotes dispersal of a non-aqueous liquid in an aqueous liquid to maintain an emulsion).

Various methods for inhibiting insect pests of plants are provided herein. In certain embodiments of such methods, the compositions comprising the PLU6-type bacteria can be applied to plants, plant parts (e.g., seeds, leaves, roots, and/or stems), or soil to which a plant is growing or is to be grown in to inhibit insect pest of the plants. Insect pests of plants that can be controlled by such applications include *Ceratitis* sp., *Delia* sp., *Mayetolia* sp., *Rhagoletis* sp., and/or *Anastrepha* sp. Application to the plant or plant part can be achieved by spraying, soaking, distribution of granulated formulations of the compositions, or otherwise applying the composition. In certain embodiments, applications can be performed serially at suitable intervals (e.g., daily, weekly, bi-weekly, monthly, or bi-monthly). Application to the soil can be achieved by a soil soak or drench, by in furrow applications, and the like. In certain embodiments, any of the aforementioned applications of the composition will provide for ingestion by the insect and/or contacting any surface of the insect with the composition. Turf grasses, crop plants, ornamental plants, vegetables, as well as nut- and fruit-bearing trees and plants can be treated with the aforementioned compositions or by the aforementioned methods. Plants and plant parts treated by the aforementioned compositions include maize, wheat, rye, barley, oats, buckwheat, sorghum, rice, onion, grass, sunflower, canola, peas, beans, soybean, cotton, linseed, cauliflower, asparagus, lettuce, tobacco mustard, sugar beet, potato, sweet potato, carrot, turnip, celery, tomato, eggplant, cucumber, squash, apple, apricot, peach, pear, plum, orange, blackberry, blueberry, strawberry, cranberry and lemon. Also provided herein are plant parts (e.g., seeds, leaves, stems, roots, tubers, and the like) that are coated or partially coated with the compositions comprising the PLU6-type bacteria. In certain embodiments, such aforementioned applications are at a rate of at least $3\times10^4$, $1\times10^5$, $3\times10^5$, $1\times10^6$, or $3\times10^6$ CFU of the PLU6-type bacteria per gram fresh weight plant tissue or soil.

Additional methods for inhibiting insect pests of humans, animals, and/or plants are also provided herein. In certain embodiments of such methods, the compositions comprising the PLU6-type bacteria are applied to soil, standing water, or any materials that will retain water, especially when or before such soil, water, materials contain insects (e.g., eggs, larvae, pupa, and/or adults), and/or to the insects. Insects that can be inhibited by such applications include dipteran insects (e.g., *Aedes* sp., *Anopheles* sp., *Culex* sp., *Ceratitis* sp., *Delia* sp., *Glossina* sp., *Musca* sp. *Mayetolia* sp., *Rhagoletis* sp., *Anastrepha* sp. a *Glossina* sp., a *Musca* sp., *Cochliomyia* sp., *Chrysops* sp., *Simulium* sp., *Phlebotomus* sp., *Culicoides* sp., or *Dermatobia* sp.). In certain embodiments, an *Aedes aegypti, Aedes aboriginis, Aedes albopictus, Aedes atlanticus, Aedes atropalpus, Aedes aurifer, Aedes bicristatus, Aedes bimaculatus, Aedes brelandi, Aedes camptorhynchus, Aedes cantator, Aedes cataphylla, Aedes cinereus, Aedes clivis, Aedes cretinus, Aedes deserticola, Aedes dupreei, Aedes epactius, Aedes fulvus, Aedes grossbecki, Aedes hensilli, Aedes hesperonotius, Aedes infirmatus, Aedes intruders, Aedes melanimon, Aedes mitchellae, Aedes notoscriptus, Aedes polynesiensis, Aedes sollicitans, Aedes squamiger, Aedes taeniorhynchus, Aedes vexans,* or *Aedes vigilax* larva is inhibited by the applications. In certain embodiments, application of the composition will provide for ingestion by the insect and/or contacting any surface of the insect with the composition. Application sites include pools, ditches, irrigation channels, tanks, pits, ponds, blocked or unblocked drains, marshes, fields with standing water, and the like. In certain embodiments, applications can be performed serially at suitable intervals (e.g., daily, weekly, bi-weekly, or monthly). Application of the compositions can be achieved by spraying, soaking, distribution of powdered, granulated, and/or encapsulated formulations of the compositions, or otherwise applying the composition. In certain embodiments, the compositions comprising the PLU6-type bacteria are applied when or before such soil, water, or materials contain mosquitos (e.g, *Aedes* sp., *Anopheles* sp., and/or *Culex* sp.), and especially when or before such soil, water, or materials contain mosquito eggs or larvae. Suitable formulations used to control *Anopheles larvae* in standing water include formulations that promote floating at the surface of the water where such larvae typically feed. Such floating or other useful formulations can be adapted from those disclosed in Aly et al., 1987, J. Am. Mosquito Control Assoc. 3:583-588; Cheung et al., 1985, Appl. Environ. Microbiol. 50:984-988, 1985; Lacey and Undeen, 1984, J. Econ. Entomol. 77:412-418. In certain embodiments, the formulations can comprise a slow-release formulation. In certain embodiments, the formulations can comprise a UV radiation blocking agent. In certain embodiments, such aforementioned applications are at a rate where the insects in a liquid matrix (e.g., water, including any standing or any other aforementioned bodies of water) are exposed to at least $3\times10^4$, $1\times10^5$, $3\times10^5$, $1\times10^6$, or $3\times10^6$ CFU of the PLU6-type bacteria per milliliter of the liquid matrix. In certain embodiments, such aforementioned applications are at a rate where the insects in a solid or semi-solid matrix (e.g., soil) are exposed to at least $3\times10^4$, $1\times10^5$, $3\times10^5$, $1\times10^6$, $3\times10^6$, $1\times10^7$, $3\times10^7$, or $1\times10^8$ CFU of the PLU6-type bacteria per gram of the solid or semi-solid matrix.

Also provided herein are methods of making the compositions comprising PLU6-type bacteria or monocultures thereof. In certain embodiments, such methods can comprise combining any of the aforementioned PLU6-type bacteria or monocultures thereof with at least one adjuvant and/or excipient, including any of the aforementioned adjuvants and/or excipients. In certain embodiments, the monoculture of the PLU6-type bacteria is obtained by steps which comprise inoculating sterile bacterial growth media with the PLU6-type bacteria, growing the *Chryseobacterium* in the growth media in the essential absence of contaminating microorganisms, and harvesting a bacterial monoculture of the PLU6-type bacteria that is essentially free of contaminating microorganisms. Growing can be in bacterial growth media suitable for growth of *Chryseobacterium* strains. Examples of such growth media include rich media such as Nutrient Yeast Salt Medium (NYSM), Nutrient Broth (3 g/L beef extract; 5 g/L peptone OR 8/L nutrient broth powder), MOPS EZ Defined Media, the formulation of which is shown below (e.g., Teknova cat #M2105), and the like.

MOPS EZ Rich Defined Media Kit (part # M2105)

| Component | 1× Concentration |
|---|---|
| MOPS | 40 mM |
| Tricine | 4 mM |
| Iron Sulfate | 0.01 mM |
| Ammonium Chloride | 9.5 mM |
| Potassium Sulfate | 0.276 mM |
| Calcium Chloride | 0.5 μM |
| Magnesium Chloride | 0.525 mM |
| Sodium Chloride | 50 mM |
| Ammonium Molybdate | $2.92\times10^{-7}$ mM |
| Boric Acid | $4.00\times10^{-5}$ mM |
| Cobalt Chloride | $3.02\times10^{-6}$ mM |

-continued

| MOPS EZ Rich Defined Media Kit (part # M2105) | |
|---|---|
| Component | 1× Concentration |
| Cupric Sulfate | $9.62 \times 10^{-7}$ mM |
| Manganese Chloride | $8.08 \times 10^{-6}$ mM |
| Zinc Sulfate | $9.74 \times 10^{-7}$ mM |
| Potassium Phosphate Dibasic Anhydrous | 1.32 mM |
| Glucose | 0.20% |
| Potassium Hydroxide | 1.5 mM |
| Adenine | 0.199 mM |
| Cytosine | 0.199 mM |
| Uracil | 0.199 mM |
| Guanine | 0.199 mM |
| L-Alanine | 0.8 mM |
| L-Arginine HCl | 5.2 mM |
| L-Asparagine | 0.4 mM |
| L-Aspartic Acid, Potassium Salt | 0.4 mM |
| L-Glutamic Acid, Potassium Salt | 0.6 mM |
| L-Glutamine | 0.6 mM |
| L-Glycine | 0.8 mM |
| L-Histidine HCl $H_2O$ | 0.2 mM |
| L-Isoleucine | 0.4 mM |
| L-Proline | 0.4 mM |
| L-Serine | 10 mM |
| L-Threonine | 0.4 mM |
| L-Tryptophan | 0.1 mM |
| L-Valine | 0.6 mM |
| L-Leucine | 0.8 mM |
| L-Lysine HCl | 0.4 mM |
| L-Methionine | 0.2 mM |
| L-Phenylalanine | 0.4 mM |
| L-Cysteine HCl | 0.1 mM |
| L-Tyrosine | 0.2 mM |
| Thiamine HCl | 0.01 mM |
| Calcium Pantothenate | 0.01 mM |
| para-Amino Benzoic Acid | 0.01 mM |
| para-Hydroxy Benzoic Acid | 0.01 mM |
| 2,3-diHydroxy Benzoic Acid | 0.01 mM |

Suitable growth conditions include both fed-batch and continuous fermentation processes. Cultures are typically subjected to aeration in the media at a temperature of about 30° C. (e.g., about 26° C. or 28° C. to about 32° C. or 34° C.). In certain embodiments, PLU6-type bacteria can be harvested by separation from the fermentation broth by centrifugation and/or filtration. In certain embodiments, harvested PLU6-type bacteria are harvested with the fermentation broth (e.g., as a whole culture comprising both bacteria and the fermentation broth) or components of the fermentation broth for use in the composition. In certain embodiments, the whole broth is concentrated by partial or complete removal of water. In certain embodiments, the whole broth or a concentrate thereof is lyophilized to obtain a dried monoculture that is essentially free of water for use in preparing the composition. In certain embodiments, the compositions made by the aforementioned methods comprise PLU6-type bacteria at a concentration of least $1 \times 10^6$, $2 \times 10^6$, $5 \times 10^6$, $1 \times 10^7$, $2 \times 10^7$, $5 \times 10^7$, $1 \times 10^8$, $2 \times 10^8$, or $5 \times 10^8$ colony forming units (CFU) per milliliter of the composition or at a titer of at least $1 \times 10^6$, $2 \times 10^6$, $5 \times 10^6$, $1 \times 10^7$, $2 \times 10^7$, $5 \times 10^7$, $1 \times 10^8$, $2 \times 10^8$, or $5 \times 10^8$ colony forming units (CFU) per gram of the composition. In certain embodiments, the compositions made by the aforementioned methods comprise PLU6-type bacteria at a concentration of $1 \times 10^6$, $2 \times 10^6$, $5 \times 10^6$, $1 \times 10^7$, or $2 \times 10^7$ to about $5 \times 10^7$, $1 \times 10^8$, $2 \times 10^8$, or $5 \times 10^8$ colony forming units (CFU) per milliliter of the composition or at a titer of $1 \times 10^6$, $2 \times 10^6$, $5 \times 10^6$, $1 \times 10^7$, or $2 \times 10^7$, to about $5 \times 10^7$, $1 \times 10^8$, or $5 \times 10^8$ colony forming units (CFU) per gram of the composition.

In some embodiments, organisms (e.g., PLU6, a PLU6-type organism, biosimilar organisms, etc.) are characterized by shotgun metagenomic sequencing. Techniques and systems to obtain genetic sequences from multiple organisms in a sample, such as an environmental or clinical sample, are well known by persons skilled in the art. For example, Zhou et al. (Appl. Environ. Microbiol. (1996) 62:316-322) provides a robust nucleic acid extraction and purification. This protocol may also be modified depending on the experimental goals and environmental sample type, such as soils, sediments, and groundwater. Many commercially available DNA extraction and purification kits can also be used. Samples with lower than 2 pg purified DNA may require amplification, which can be performed using conventional techniques known in the art, such as a whole community genome amplification (WCGA) method (Wu et al., Appl. Environ. Microbiol. (2006) 72, 4931-4941). Techniques and systems for obtaining purified RNA from environmental samples are also well known by persons skilled in the art. For example, the approach described by Hurt et al. (Appl. Environ. Microbiol. (2001) 67:4495-4503) can be used. This method can isolate DNA and RNA simultaneously within the same sample. A gel electrophoresis method can also be used to isolate community RNA (McGrath et al., J. Microbiol. Methods (2008) 75:172-176). Samples with lower than 5 pg purified RNA may require amplification, which can be performed using conventional techniques known in the art, such as a whole community RNA amplification approach (WCRA) (Gao et al., Appl. Environ. Microbiol. (2007) 73:563-571) to obtain cDNA. In some embodiments, environmental sampling and DNA extraction are conducted as previously described (DeSantis et al., Microbial Ecology, 53(3):371-383, 2007).

Isolated nucleic acids can be subject to a sequencing method to obtain sequencing data. Sequencing methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively. Accordingly, metagenomic shotgun sequencing comprises, in some embodiments, pyrosequencing, sequencing-by-ligation, single molecule sequencing, sequence-by-synthesis (SBS), semiconductor sequencing, nanopore sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

Specific descriptions of some DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety); automated sequencing techniques; parallel sequencing of partitioned amplicons (PCT Publication No: WO2006084132 to Kevin McKernan et al., herein incorporated by reference in its entirety); and sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional descriptions of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695, 934; 5,714,330; herein incorporated by reference in their entireties), and the Adessi PCR colony technology (Adessi et al. (2000). Nucleic Acid Res. 28, E87; WO 00018957; herein incorporated by reference in its entirety). See also, e.g., Voelkerding et al., Clinical Chem., 55: 641-658, 2009; MacLean et al., Nature Rev. Microbiol., 7: 287-296; each herein incorporated by reference in its entirety).

Data collected during the experiments described herein indicated that PLU6, PLU6-type organisms, and organisms having insecticidal activity similar to PLU6 and PLU6-type organisms had insecticidal activity. In some embodiments, the insecticidal organism is a member of the genus *Chryseobacterium*, e.g., a *Chryseobacterium* species such as, e.g., *Chryseobacterium gleum*. See also FIGS. 9 and 10.

Data collected during the experiments described herein indicated that diindolylalkane compounds had insecticidal activity. Accordingly, the technology described herein provides an insecticidal compound having the structure as follows:

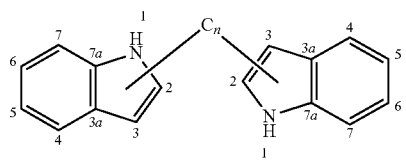

In this structure, $C_n$ is a linker that comprises an alkylene group or equivalent (e.g., an alkyl chain having 1 to 12 carbon atoms). Exemplary, non-limiting insecticidal compounds are 3,3-diindolylmethane and 3-((1H-indol-2-yl) methyl)-1H-indole. As indicated by these exemplary compounds, the insecticidal compounds provided herein comprise two indole moieties linked by a linker comprising an alkylene chain (e.g., methylene (—$CH_2$—)) attached at the position 2 or 3 carbon of each indole group. The linker between the two indole groups may be any chemical linker provided that it does not substantially inhibit the killing activity of the insecticidal compound.

Furthermore, data collected during the experiments described herein indicated that PLU6, PLU6-type organisms, organisms having insecticidal activity similar to PLU6 and PLU6-type organisms, and/or diindolylalkane compounds were insecticidal against insects in the taxonomic orders Diptera and Lepidoptera. Further, data collected during the experiments described herein indicated that PLU6, PLU6-type organisms, organisms having insecticidal activity similar to PLU6 and PLU6-type organisms, and/or diindolylalkane compounds were insecticidal against insects in the taxonomic families Culicidae, Noctuidae, Tortricidae, Crambidae, and Erebidae. Data collected during the experiments described herein indicated that PLU6, PLU6-type organisms, organisms having insecticidal activity similar to PLU6 and PLU6-type organisms, and/or diindolylalkane compounds were insecticidal against *Ae. aegpyti, C. quinquefasciatus, H viriscens, T ni, S. exigua, C. includens, H zea, S. eridania, S. frugiperda, D. saccharalis, D. grandiosella*, and *A. gemmetalis*. These species represent a broad variety of insects including moths and other caterpillars, borers, armyworms, and mosquitos.

In some embodiments, the technology relates to a transgenic plant comprising a heterologous nucleic acid, which can be introduced into a plant cell in a number of art-recognized ways. Those skilled in the art will appreciate that the choice of method might depend on the type of plant targeted for transformation. In some embodiments, the vector is maintained episomally. In other embodiments, the vector is integrated into the genome. A polynucleotide can be introduced into a cell by a variety of methods well known to those of ordinary skill in the art. For example, the polynucleotide can be introduced into a plant cell using a direct gene transfer method such as electroporation or microprojectile mediated transformation, or using *Agrobacterium* mediated transformation. See, e.g., Hinchee et al. (1988) Biotechnology, 6:915; Ishida et al. (1996) Nature Biotechnology 14:745, all of which are herein incorporated by reference).

Although the disclosure herein refers to certain illustrated embodiments, it is to be understood that these embodiments are presented by way of example and not by way of limitation.

EXAMPLES

Example 1

*Chryseobacterium* PLU6 cultures were grown aerobically in sterile Nutrient Yeast Salt Medium (NYSM). The NYSM contained 8 g/L nutrient broth powder, 0.5 g/L yeast extract, 1 mM $MgCl_2$, 700 μM $CaCl_2$, 50 μM $MnCl_2$. Growth was at 30° C. and 200-250 rpm on a rotary shaker. PLU6 was sampled after 2 days of growth for application to multiple species of mosquito larvae.

*Ae. aegypti* eggs were purchased from Benzon Research (Carlisle, PA). Eggs were hatched under vacuum into sterile water. *Culex quinquefasciatus* and *Anopheles quadrimaculatus* larvae (first or second instar) were also purchased from Benzon Research (Carlisle, PA). Larvae were reared at approximately 22° C. in trays containing water at an approximate larval density of 2 larvae/mL and fed crushed TETRAMIN fish food tablets, powdered Enterra Protein (Enterra, Langley, BC, Canada), or powdered cricket protein (Bud's Cricket Protein Powder, Harrison Food Group).

*Culex quinquefasciatus* and *Anopheles quadrimaculatus* larvae (first or second instar) were also purchased from Benzon Research (Carlisle, PA). Larvae were reared to third instar at approximately 22° C. in trays containing water at an approximate larval density of 2 larvae/mL and fed crushed TETRAMIN fish food tablets or powdered Enterra Protein (Enterra, Langley, BC, Canada).

Third instar larvae were used for all assays. Larvae were washed once in sterile water before transfer to assay plates. Assays were performed in 12-well assay plates, with wells containing 2 mL sterile water and five (5) larvae per well. Bacterial culture was applied to each assay well. Larval mortality was scored at indicated timepoints after application.

To test whether the larvicidal activity of whole culture of PLU6 was associated with the cell pellet or supernatant fractions, we fractionated whole culture via centrifugation. PLU6 cultures were grown aerobically in sterile Nutrient Yeast Salt Medium (NYSM) [8 g/L nutrient broth powder, 0.5 g/L yeast extract, 1 mM $MgCl_2$, 700 µM $CaCl_2$, 50 µM $MnCl_{2]}$ at 30° C. and 250 rpm. Cultures were sampled at indicated timepoints for application to Ae. aegypti larvae. To separate cell pellet and supernatant fractions of PLU6, 200 microliters of whole culture was centrifuged at 4000 rpm for 10 minutes. Supernatants were filtered through a 0.22 µm sterile centrifugal filter to eliminate any remaining bacterial cells and applied to larvae. Cell pellets were resuspended in 200 microliters fresh NYSM media and applied to third instar Ae. aegypti larvae. Larval mortality was assessed at 72 hours.

Bacillus thuringiensis subspecies israelensis strains were used as positive and negative controls. Larvicidal positive control Bacillus thuringiensis subspecies israelensis was sourced from a commercially available product comprising Bacillus thuringiensis subspecies israelensis (SUMMIT MOSQUITO DUNKS/BTI Briquets, Summit Chemical Company, Baltimore, Maryland). Bacillus thuringiensis subspecies israelensis strain 4Q7 from the Bacillus Genetic Stock Center (Ohio State University, Columbus, OH) is a strain of Bacillus thuringiensis subspecies israelensis from which the plasmid encoding the larvicidal toxin has been removed and was used as a negative control for larvicidal activity. NYSM media was also used as a negative control in the larvicide activity assays.

Chryseobacterium strain ATCC29898 [Chryseobacterium sp. (ATCC29898)] was used as a negative control for larvicidal activity. ATCC29898 was reclassified as Chryseobacterium taihuense. The taxonomic classification of the negative control as Chryseobacterium taihuense was confirmed by recovering the 16S sequence after whole genome sequencing and aligning it with known 16S sequences. Chryseobacterium strain ATCC29898 was purchased from the American Type Culture Collection (ATCC, Manassas, VA).

Results

Figure 1:
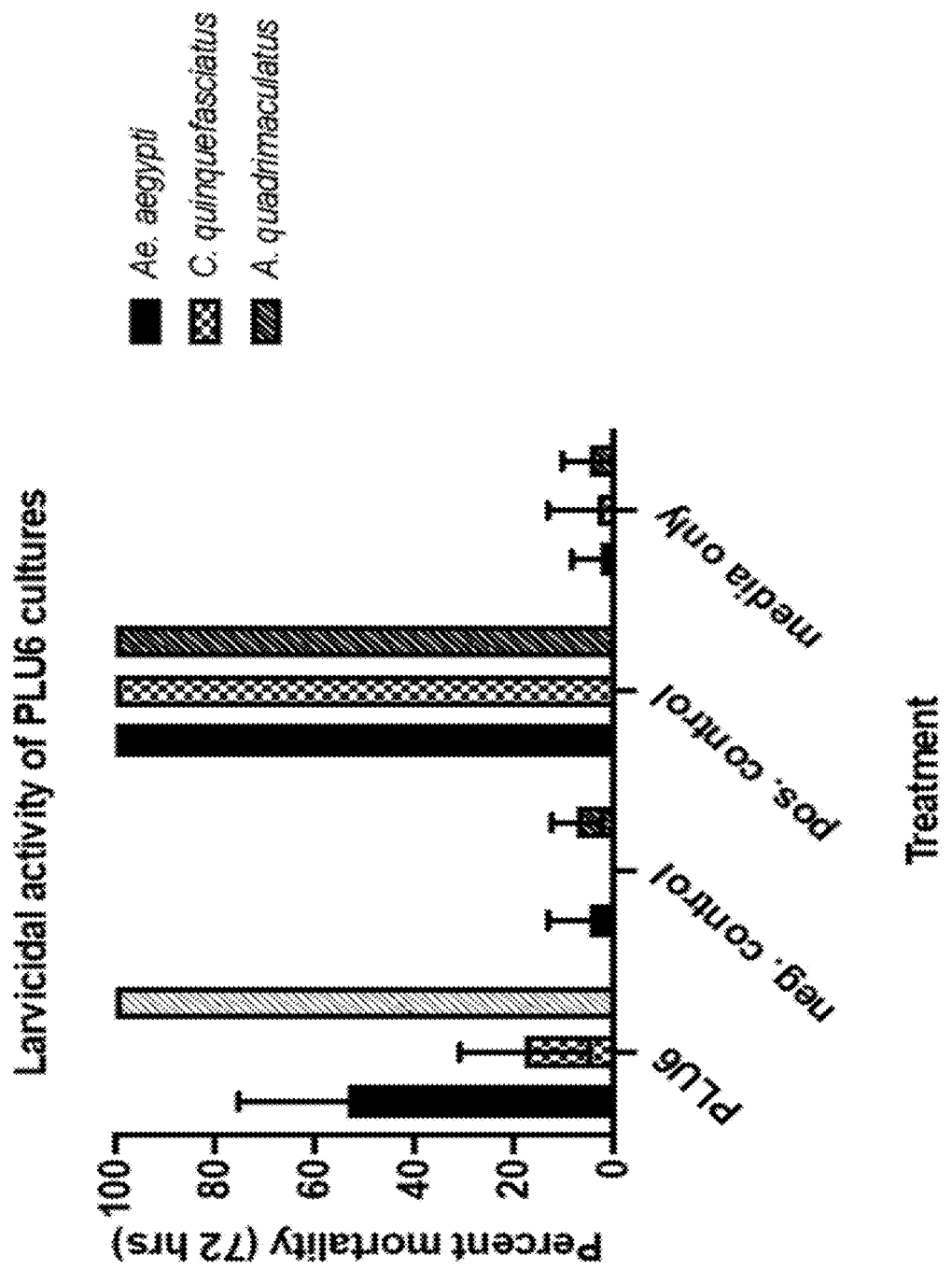

As shown in FIG. 1, Chryseobacterium strain PLU6 isolated from soil has larvicidal activity against various species of mosquito larvae (Aedes aegypti, Culex quinquefasciatus, and Anopheles quadrimaculatus). PLU6 was most active against Anopheles quadrimaculatus and had minimal activity against Culex quinquefasciatus. These results suggest that the mechanism of action of PLU6 is not specific to a genus or species of mosquito.

Figure 2:
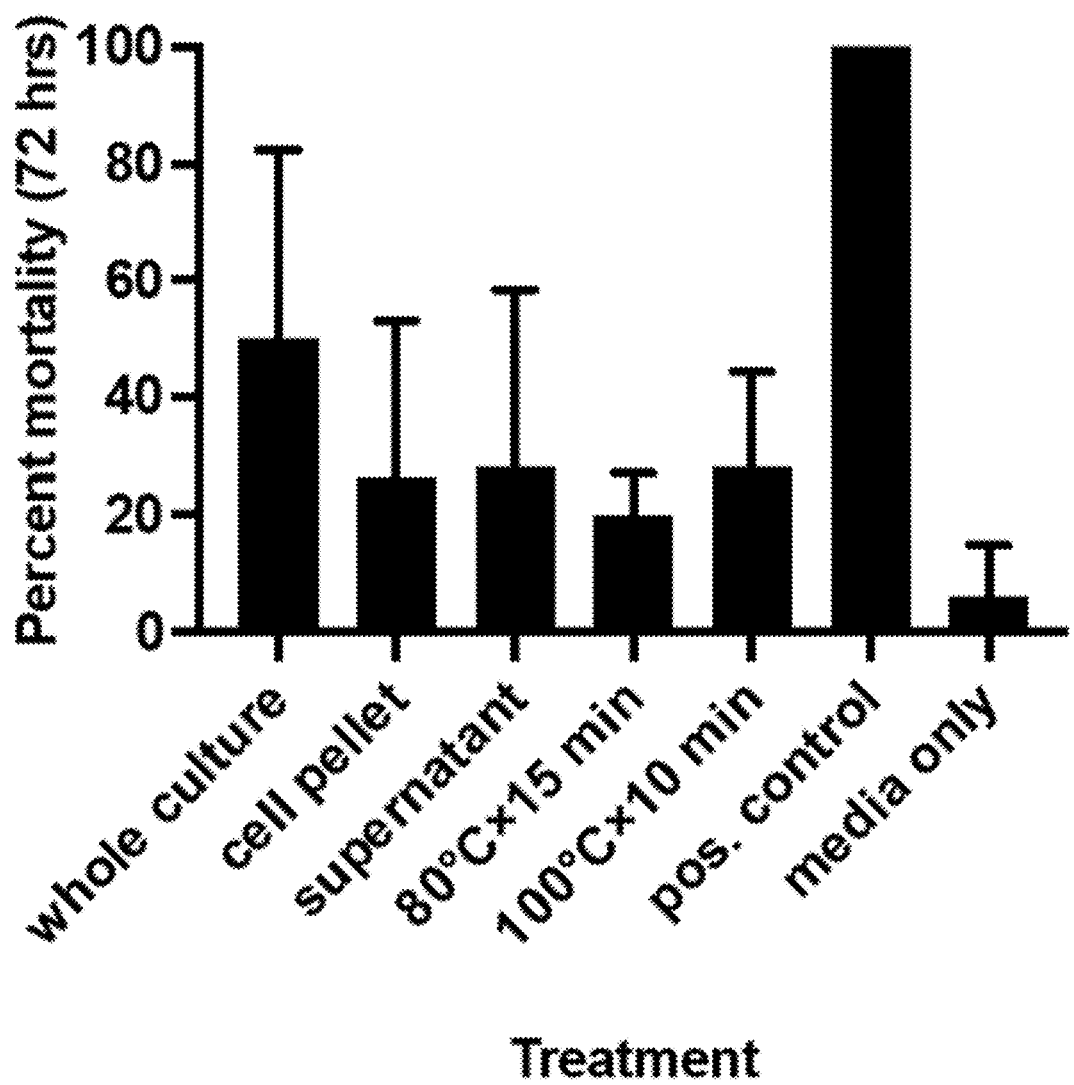

As shown in FIG. 2, larvicidal activity for PLU6 is greatest when applied as a whole culture. Activity is associated with both the cell pellet and supernatant fractions but may be reduced upon fractionation or may be due to the presence of multiple active components. PLU6 activity displays intermediate heat sensitivity as whole culture.

Figure 3:
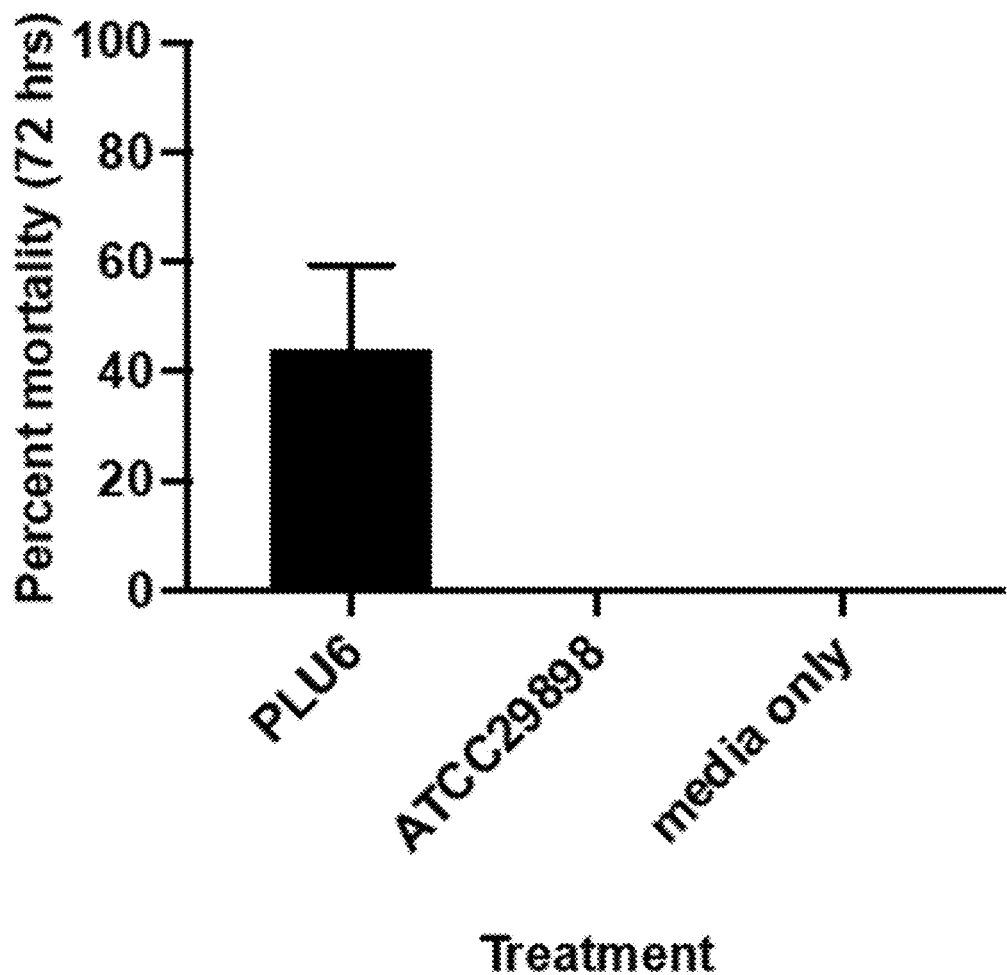

As shown in FIG. 3, larvicidal activity observed in PLU6 is not conserved amongst all Chryseobacterium and may be specific to PLU6 or C. gleum. Genes unique to PLU6 when compared to ATCC29898 may contribute to or be responsible for larvicidal activity.

Figure 4:
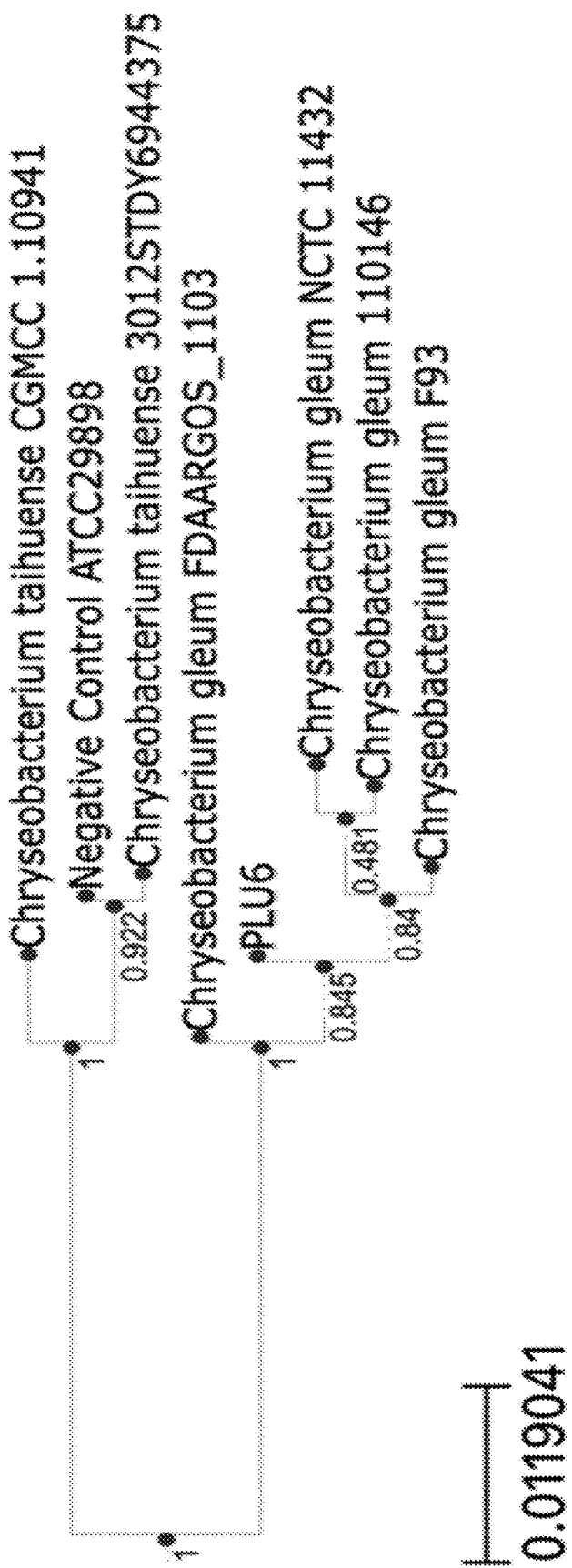
Figure 5:
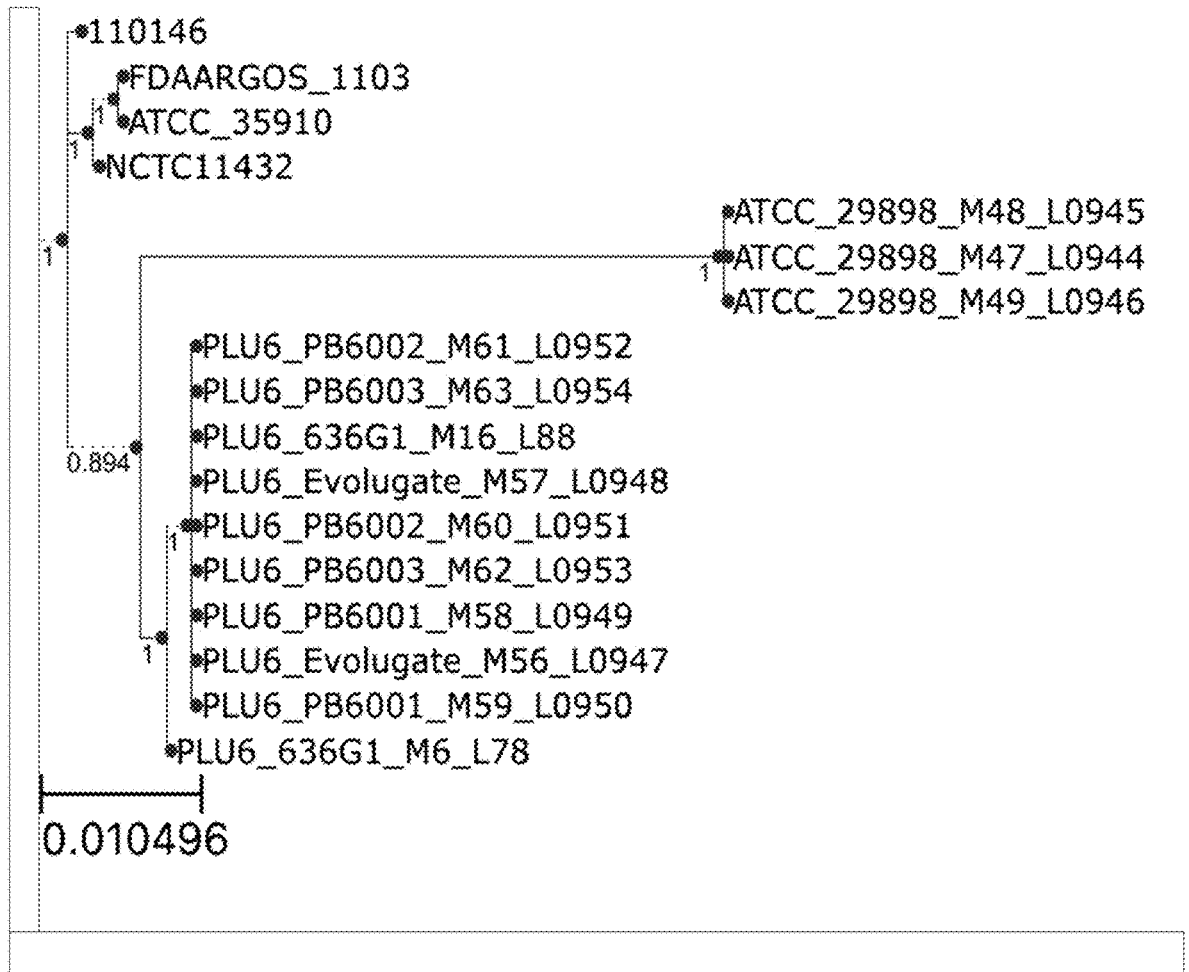

FIG. 4 shows that PLU6 is characterized as Chryseobacterium gleum and the negative control is characterized as Chyseobacterium taihuense. Alignment of 16S genes is a golden standard within the field used primarily to classify taxonomy of bacterial strains.

Table 1 provided herewith and which is incorporated by reference in its entirety herein, provides a summary of the sequences provided in the accompanying sequence listing (SEQ ID NOs: 851-1202) as well as the accession number and name of a related sequence found in the Pfam protein families database (Finn et al. Nucleic Acids Research (2016) Database Issue 44:D279-D285; https internet site "pfam.xfam.org").

One way to identify the genes critical for a given activity is to use comparative genomics. Table 2 provided herewith and which is incorporated by reference in its entirety herein, identifies genes that were only in strains that had insecticidal activity, representing 402 coding regions. Without being bound by theory, it is contemplated that at least some of these genes are involved in insecticidal activity.

Example 2

During the development of embodiments of the technology described herein, experiments were conducted to test the insecticidal activity of cultures comprising PLU6 and PLU6-type organisms, compositions prepared from cultures comprising PLU6 and PLU6-type organisms, small molecules produced by PLU6 and PLU6-type organisms, and/or small molecules related to small molecules produced by PLU6 and PLU6-type organisms.

Production of cell-free supernatants from bacterial cultures. Cells from a cryostock were streaked on an NYSM agar plate and incubated at 30° C. overnight. A single colony was used to inoculate 5 milliliters of NYSM broth in a 50 mL conical tube, which was incubated at 30° C. and 200 rpm overnight. A new 5-mL culture was then inoculated with 10 microliters of the "starter culture" and was incubated at the same temperature and shaking frequency as above. After 24 hours of incubation, the overnight culture was centrifuged at 5100 rcf for 15 minutes. The supernatant was then pipetted into a new 50 mL conical tube and filter sterilized using a Steri-flip 0.2-µm vacuum filter (MILLIPORESIGMA catalog #SCGP00525).

Measuring potency of 3,3-diindolylmethane and 3-((1H-indol-2-yl)methyl)-1H-indole. 3,3'-Diindolylmethane (also called arundine, CAS number: 1968-05-4) was purchased from MILLIPORESIGMA (cat #74601) and Cayman Chemical (catalog #15927). 3-((1H-indol-2-yl)methyl)-1H-indole (CAS number: 114648-66-7) was purchased from Ambeed (catalog #A735658). Compounds were resuspended in dimethyl sulfoxide (DMSO). For collecting data to construct dose curves for 3,3-diindolylmethane and 3-((1H-indol-2-yl)methyl)-1H-indole, a series of twenty 1:2 dilutions was made to test in bioassays, establish a dose curve, and determine the $LC_{50}$ value.

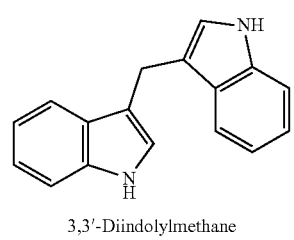

3,3'-Diindolylmethane

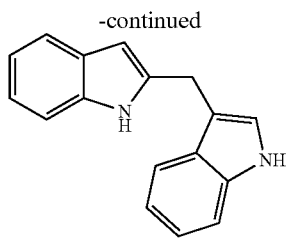

3-((1H-indol-2-yl)methyl)-1H-indole

*Aedes aegypti* bioassays with compounds. Assays were performed using second or third instar larvae, with biological replication. Larvae were washed with sterile water before transfer to 24-well assay plates containing 1 mL of sterile water in each well. Each well contained 5 larvae. Compound dilutions were made in DMSO, topped with sterile NYSM broth and applied to each assay well. The final DMSO concentration was 1% in each assay well. Larval mortality was scored for each well at 24-hour timepoints after application.

*Culex quinquefasciatus* bioassays with compounds. First or second instar *Culex quinquefasciatus* larvae were purchased from Benzon Research, Inc. (Carlisle, PA). Assays were performed with third instar larvae. Larvae were washed with sterile water before transfer to 24-well assay plates containing 1 mL of sterile water in each well. Each well contained 5 larvae. Compound dilutions were made in DMSO, topped with sterile NYSM broth and applied to each assay well. The final DMSO concentration was 1% in each assay well. Larvae mortality was scored for each well at 24-hour timepoints after application.

Lepidopteran bioassays. Lepidopteran bioassays were performed at Benzon Research, Inc. (Carlisle, PA). 3,3'-Diindolylmethane samples were solubilized in dimethyl sulfoxide (DMSO). Samples were then frozen and shipped to Benzon. Samples were resuspended with 9× volumes of water before application to the assay well. The final DMSO concentration in the assay well was 2%. PLU6 extract samples were prepared as a series of three 1:5 dilutions in dimethyl sulfoxide. Samples were then further diluted with fresh NYSM broth, then shipped to Benzon Research for use in a diet overlay assay. Assays were performed using neonate larvae of 14 different Lepidopteran species (*Anticarsia gemmatalis* (velvetbean caterpillar), *Diatraea grandiosella* (southwestern corn borer), *Diatraea saccharalis* (sugarcane borer), *Ostrinia nubilalis* (European corn borer), *Trichoplusia ni* (cabbage looper), *Chrysodeixis includens* (soybean looper), *Spodoptera exigua* (beet armyworm), *Spodoptera frugiperda* (fall armyworm), *Spodoptera eridania* (southern armyworm), *Chloridia virescens* (tobacco budworm), *Helicoverpa zea* (corn earworm), *Agrotis ipsilon* (black cutworm), *Cydia pomonella* (codling moth), *Plutella xylostella* (diamondback moth) with an N=16 or N=32, apart from *P. xylostella*, for which third instar larvae were used. A diet-surface overlay format was used, in which 500 microliters of diet was placed in each well. One hundred microliters of sample was then pipetted into each well and allowed to dry. A DMSO control was included with each set of samples. An internal Btk (*Bacillus thurengiensis kurstaki*) standard at a concentration of 1000 ppm was used as a positive control, and water was used as a negative control.

Heat treatments. Samples were heated in 1.5-mL microfuge tubes in a standard laboratory heat block at the indicated temperature and time.

Preparation and characterization of larvicidal metabolites. Chemicals were purchased from Sigma-Aldrich or Merck unless otherwise specified. Analytical-grade solvents were used for solvent extractions. Solvents used for HPLC, UPLC, and HPLC-MS purposes were of HPLC grade supplied by Labscan or Sigma-Aldrich and filtered/degassed through 0.45 μm polytetrafluoroethylene (PTFE) membrane prior to use. Deuterated solvents were purchased from Cambridge Isotopes (Tewksbury, MA, USA). Nutrient broth culture medium was obtained from EM science chemicals. Preparative and semi-preparative HPLCs were performed using Shimadzu LC-20AT HPLC instruments with corresponding detectors, fraction collectors, and software, inclusively. Electrospray ionization mass spectra (ESIMS) were acquired using a Schimadzu LC-20AD separations module equipped with a Schimadzu LCMS-2020 Series mass detector in both positive and negative ion modes under the following conditions: Phenomenex kinetex Phenylhexyl 5 μm column, 100×4.6 mm, eluting with 1.0 mL/min of isocratic 90% $H_2O$/MeCN for 1 min followed by gradient elution to 100% MeCN (with isocratic 0.1% HCOOH modifier) over 15 min, at 210 and 254 nm. UHPLC-QTOF analysis was performed on an UHPLC-QTOF instrument comprising an Agilent 1290 Infinity II UHPLC (Phenomenex Kinetex 1.7 μm phenylhexyl column, 50×2.1 mm, eluting with 0.4 mL/min of isocratic 90% $H_2O$/MeCN for 1 min followed by gradient elution to 100% MeCN over 6 min (with isocratic 0.1% formic acid modifier) coupled to an Agilent 6545 LC/Q-TOF-MS system operating in positive mode, monitoring a mass range of 100 to 2000 amu. NMR spectra were obtained on an Agilent 600 NMR spectrometer ($^1$H: 600 MHz, 13C: 150 MHz) equipped with a 5 mm DB AUTOX PFG broadband probe and a Varian NMR System console, with automatic tuning and matching in the solvents indicated and referenced to residual signals ($\delta_H$ 3.31 and $\delta_C$ 49.0 ppm for MeOH) in deuterated solvents. All data analysis was performed using MestReNova NMR software.

Biosimilar *Chryseobacterium* and *Flavobacterium* strains were isolated from soil samples, streaked for isolation on solid media, and their genera verified using their 16S rRNA gene sequences and bioinformatic tools known in the art.

Figure 7:
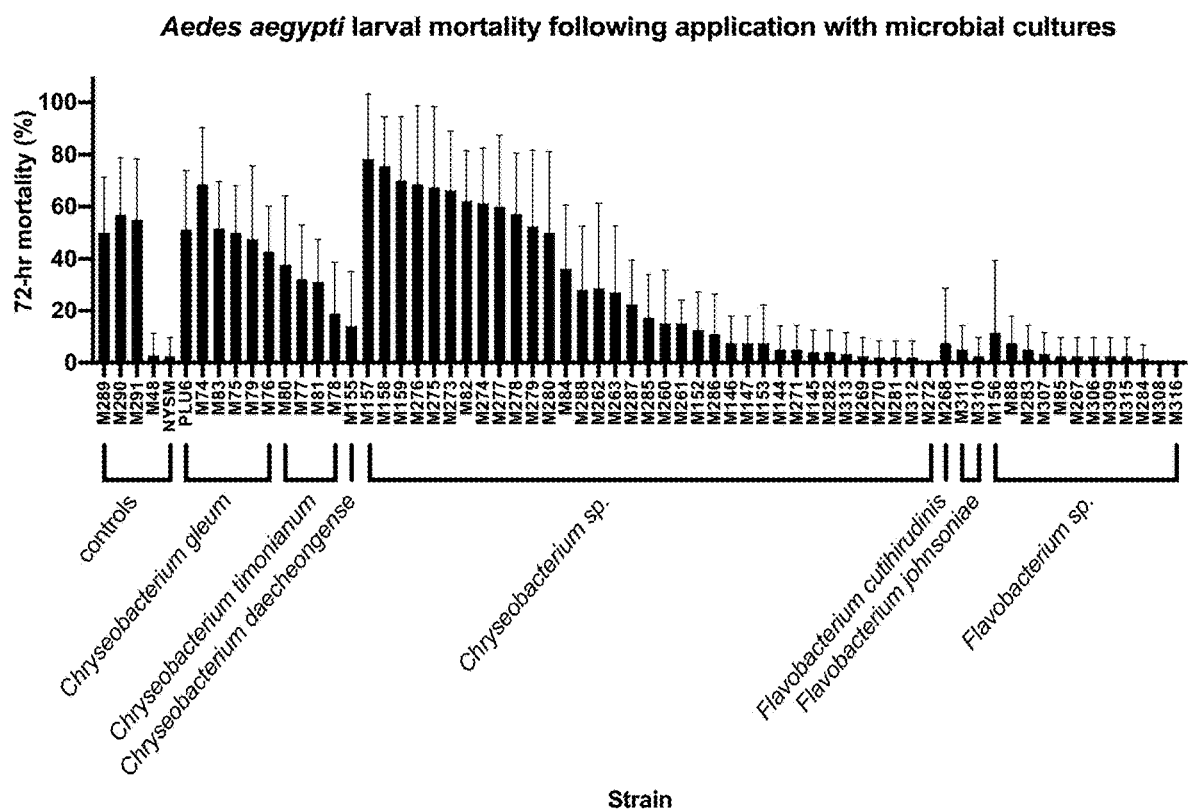

During the development of embodiments of the technology described herein, experiments were conducted to test the larvicidal activity of *Chryseobacterium* strains related to PLU6 ("biosimilars") isolated from environmental sources. During these experiments, data were collected indicating that *Chryseobacterium* species exhibit larvicidal activity against *Ae. aegypti* larvae (FIG. 7). Cultures were applied at 10% v/v. Strains M289, M290, M291, and M48 are control strains sourced from the American Type Culture Collection. M289, M290, and M291 are clones of ATCC29897 (*C. indologenes*). Strain M48 is a clone of ATCC29898 (*C. taihuense*). NYSM represents the negative control (media, no bacterial cells). Isolated *Flavobacterium* strains are also shown. Error bars represent standard deviations calculated from at least three independent replicates. As shown by FIG. 7, distinct *Chryseobacterium* species have larvicidal activity against *Ae. aegypti* larvae.

Figure 8:
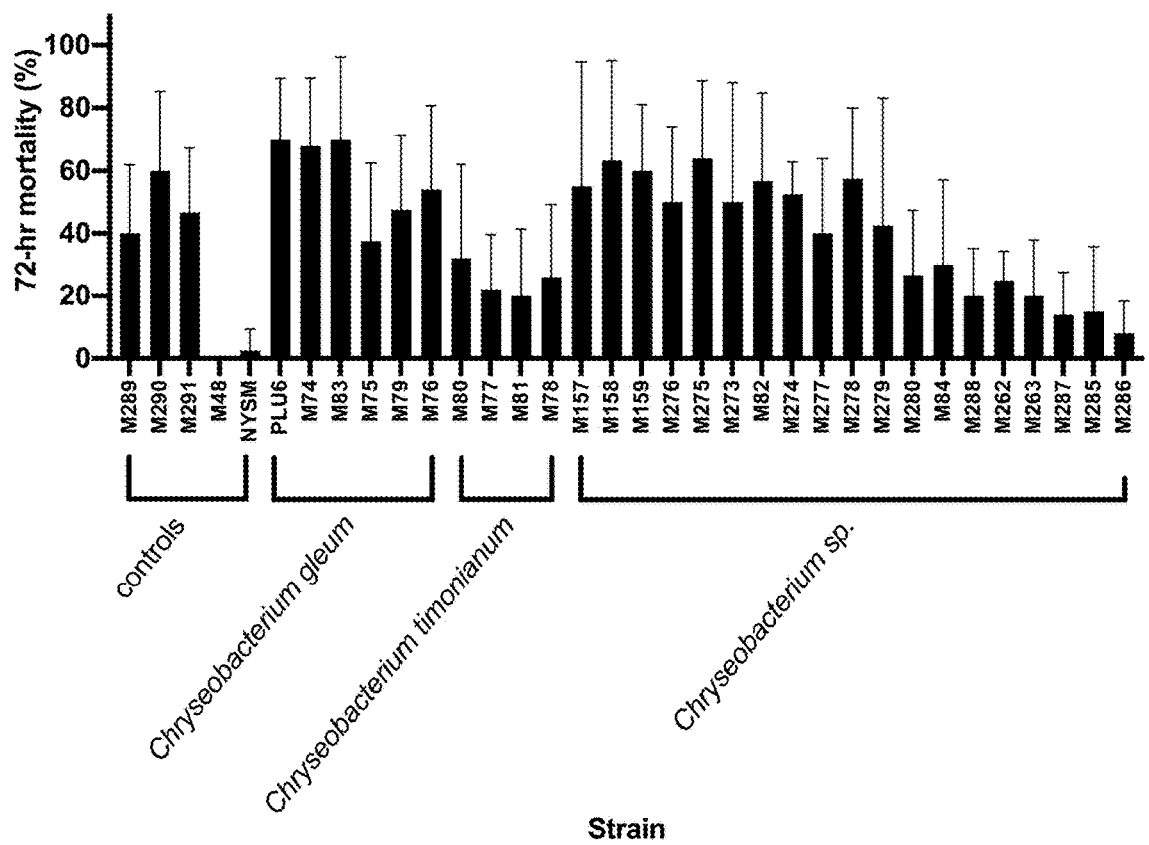

During the development of embodiments of the technology described herein, experiments were conducted to test the larvicidal activity of cell-free supernatants derived from *Chryseobacterium* strains biosimilar to PLU6. During these experiments, data were collected indicating that a component (e.g., a compound or compound(s)) excreted into culture media by PLU6 and related biosimilar strains have larvicidal activity (FIG. 8). Cell-free culture supernatants were applied at 10% v/v. Strains M289, M290, M291, and M48 are control strains sourced from the American Type Culture Collection. M289, M290, and M291 are clones of ATCC29897 (*C. indologenes*). Strain M48 is a clone of ATCC29898 (*C. taihuense*). NYSM represents the negative control (media, no bacterial cells). Error bars represent standard deviations calculated from at least three independent biological replicates.

Figure 9A:
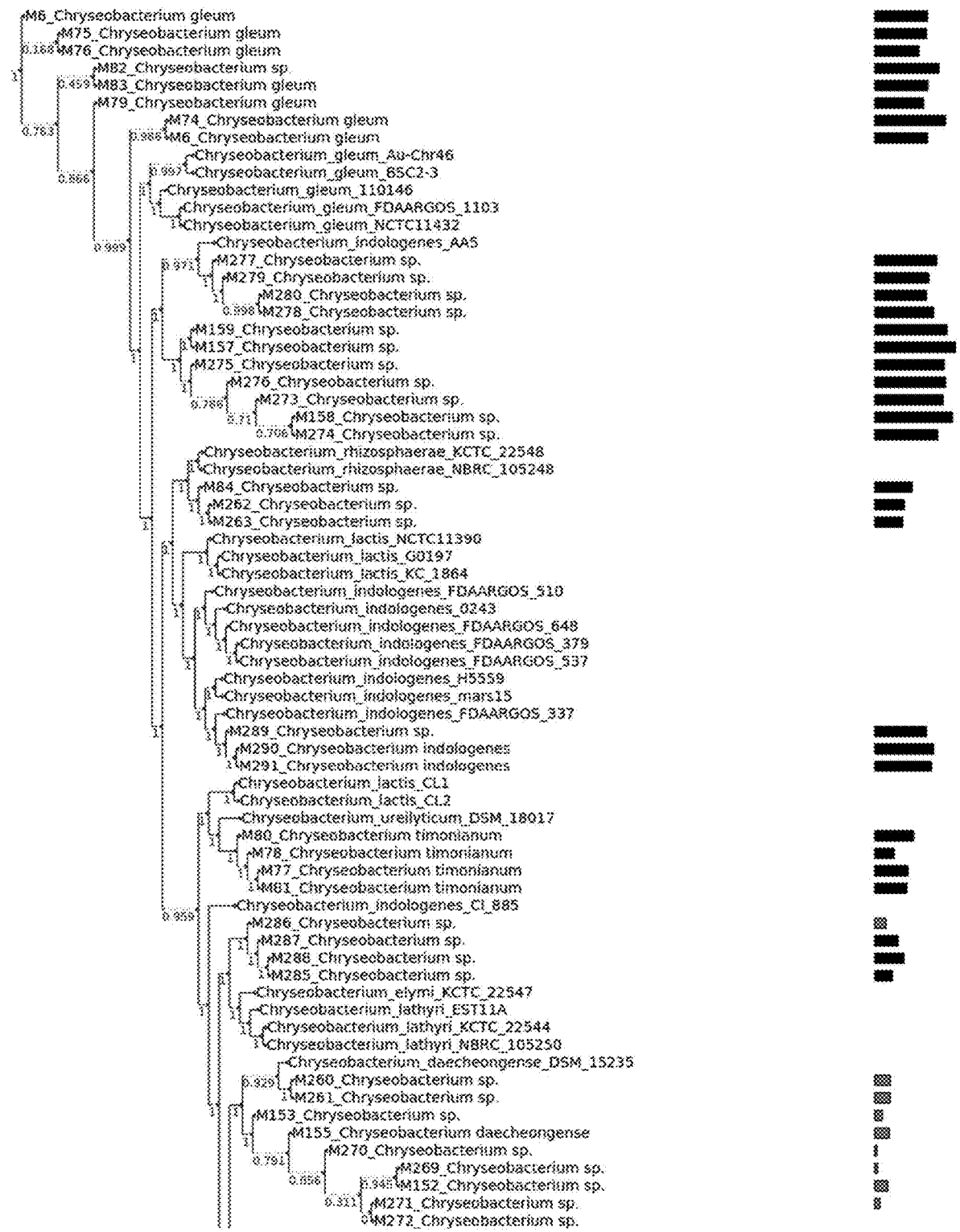
Figure 9B:
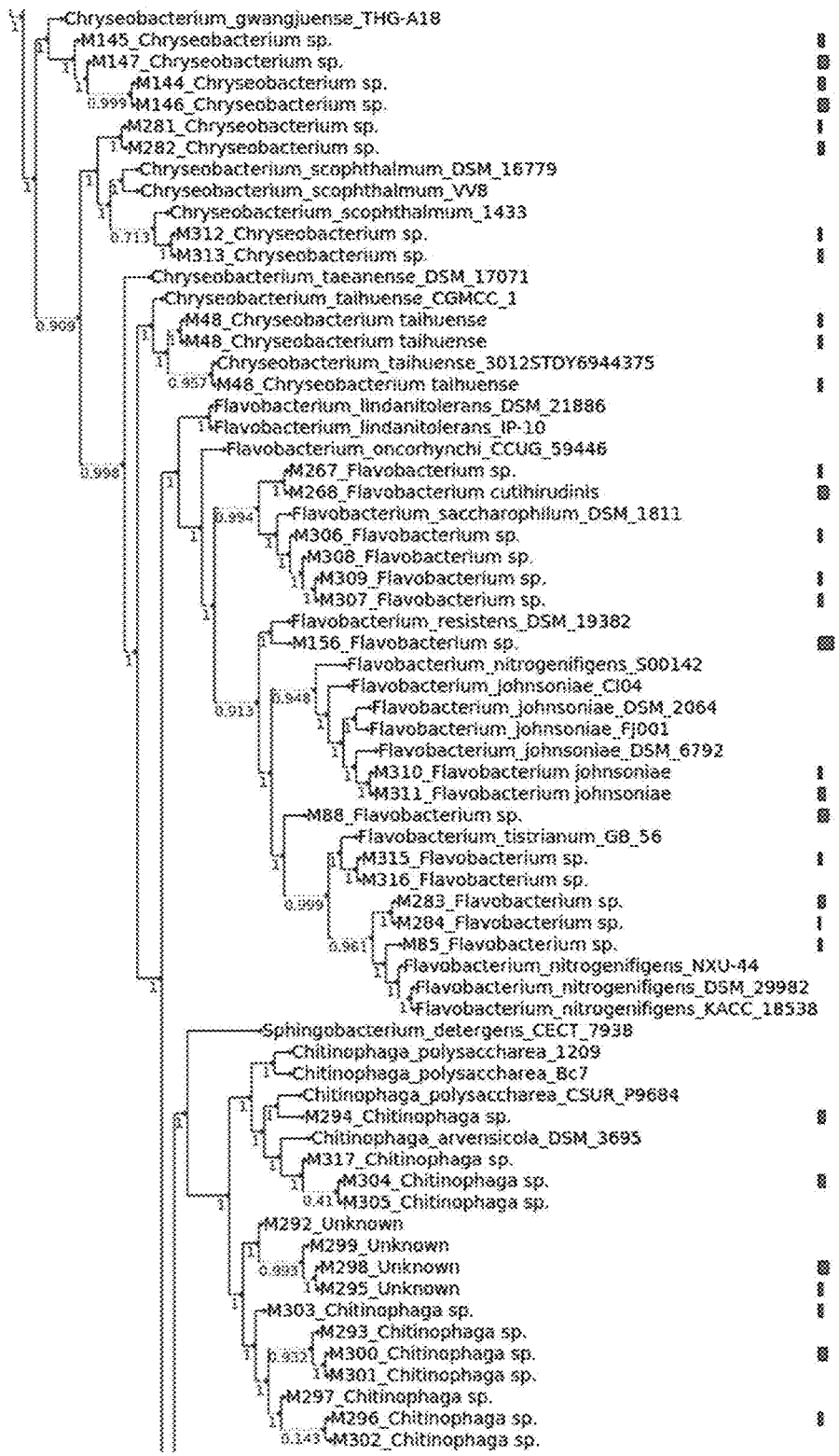
Figure 9C:
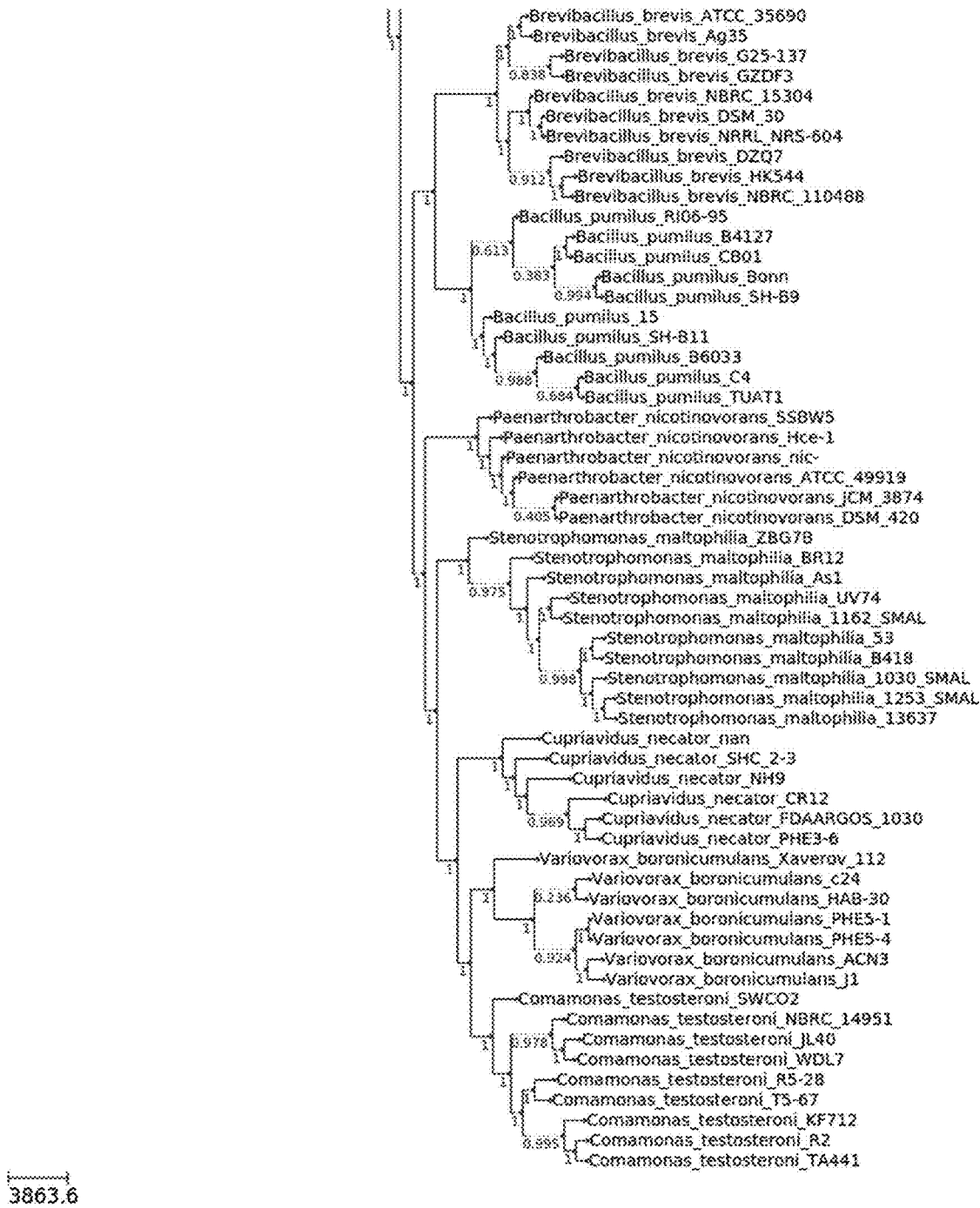
Figure 10A:
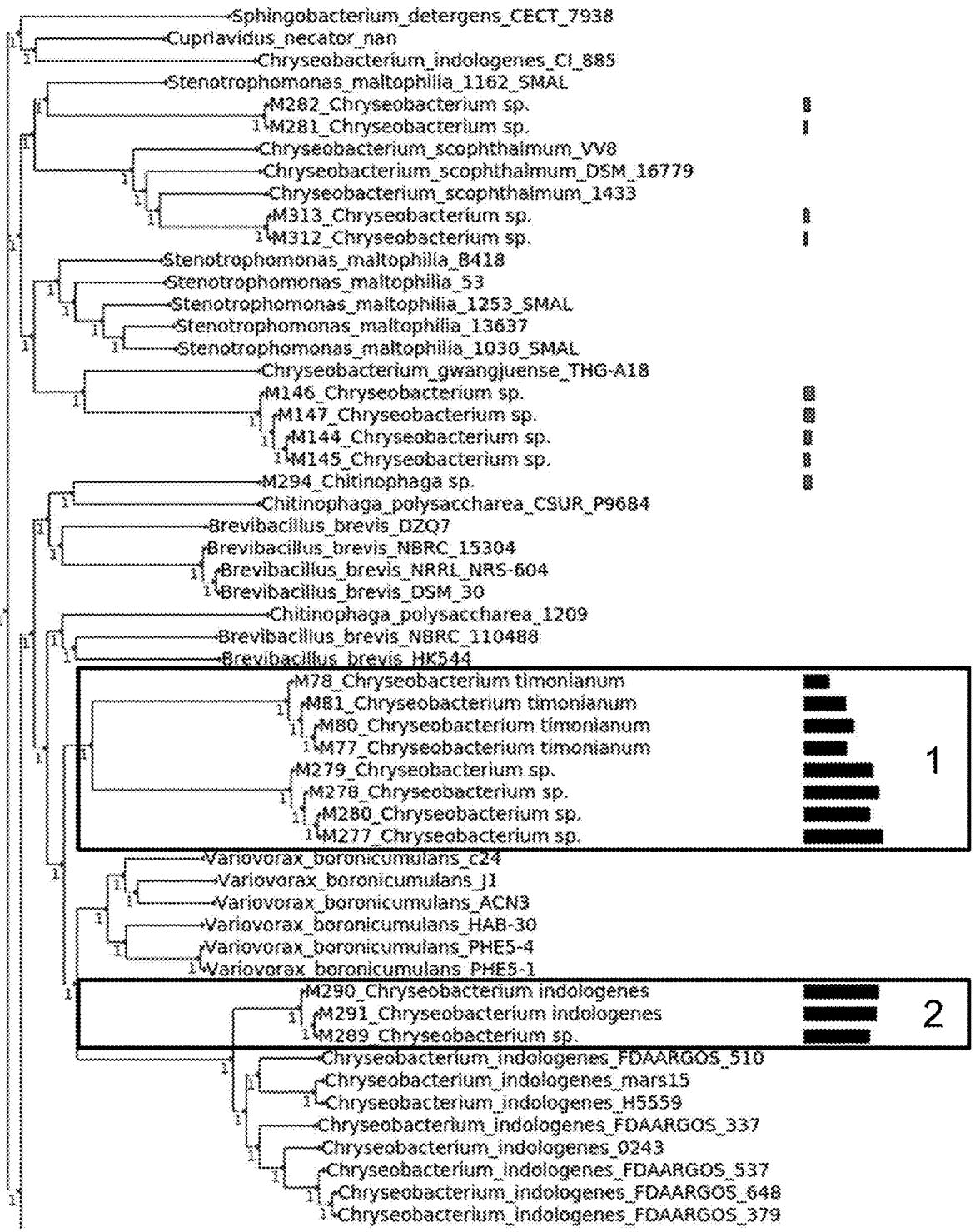
Figure 10B:
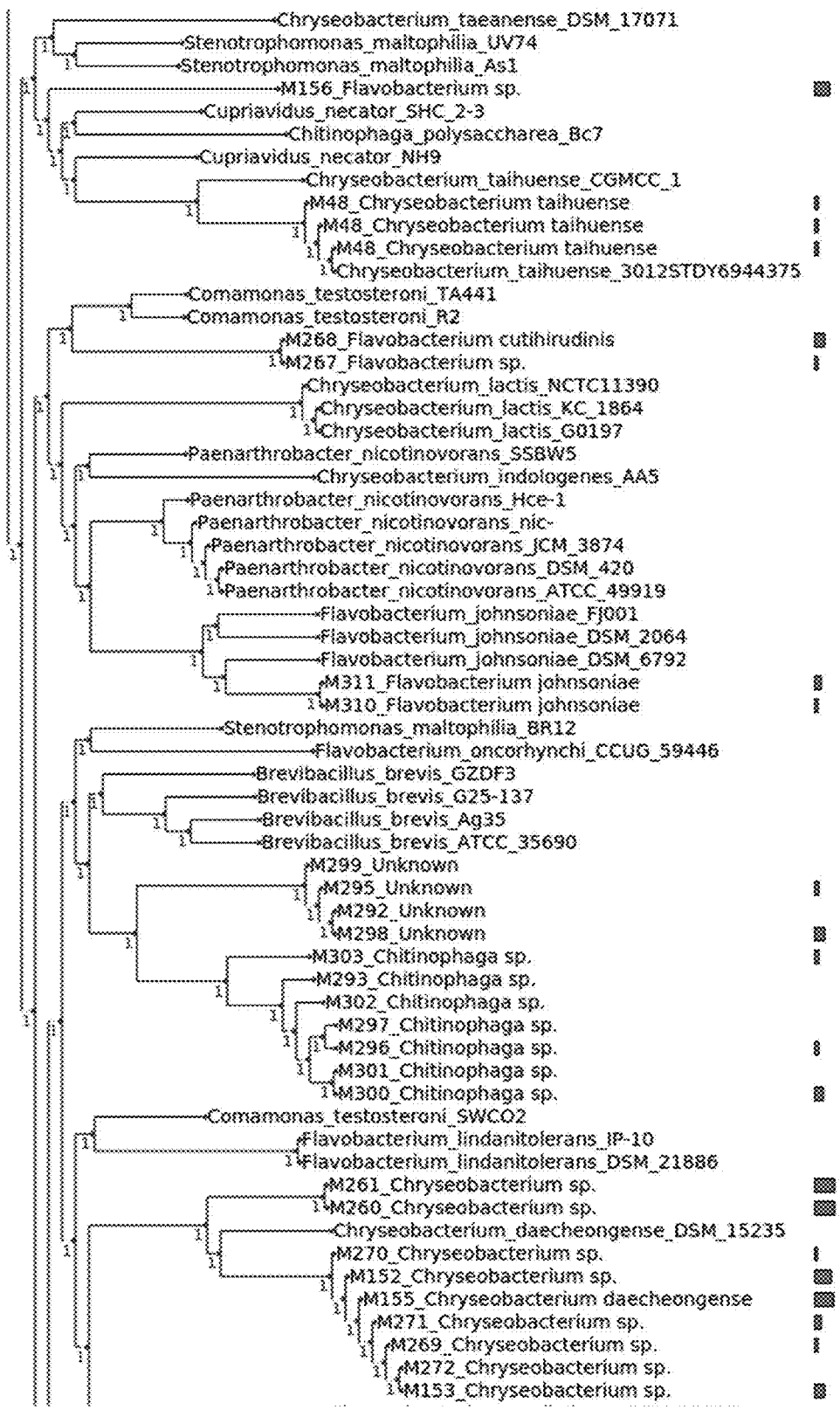
Figure 10C:
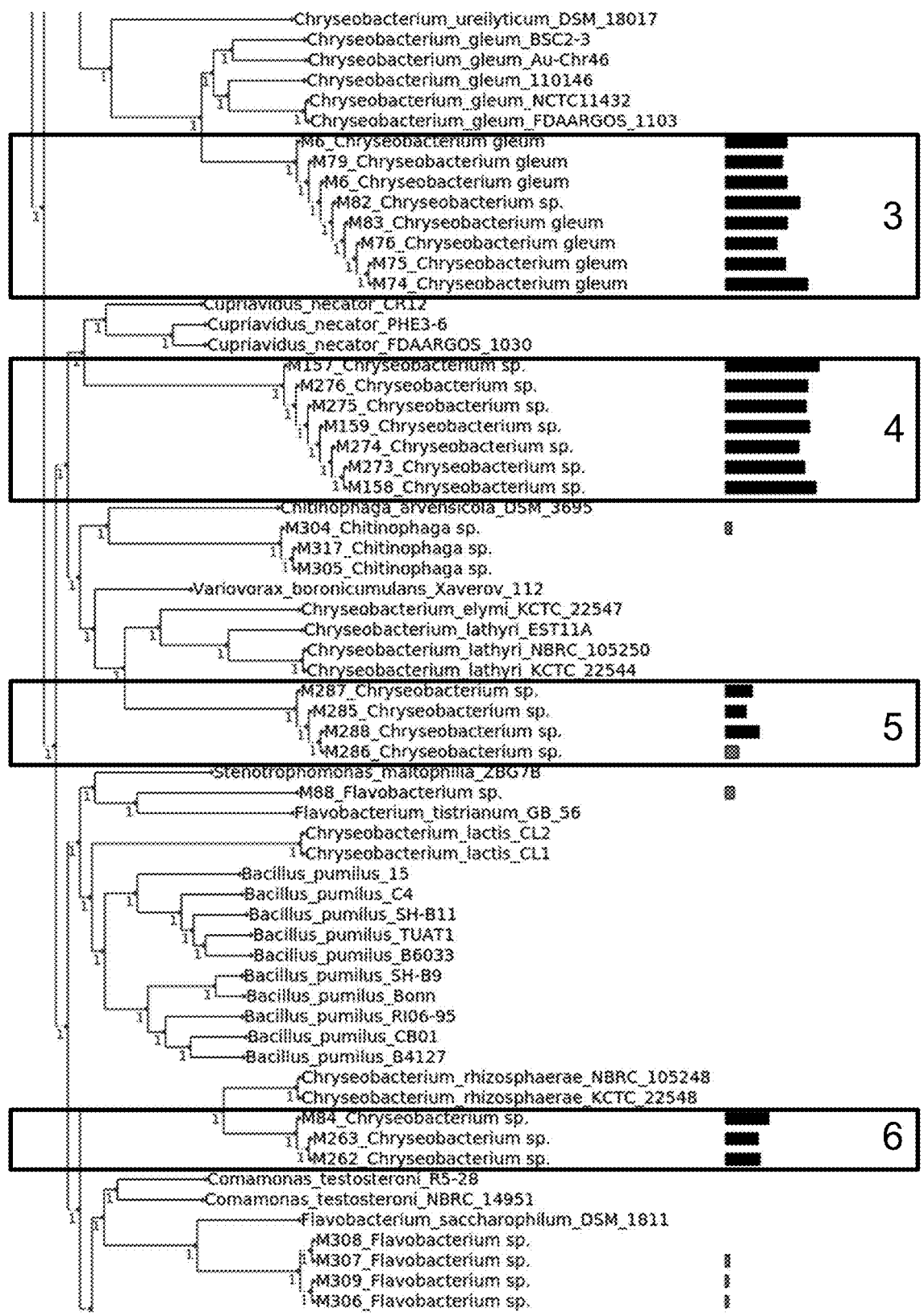
Figure 10D:
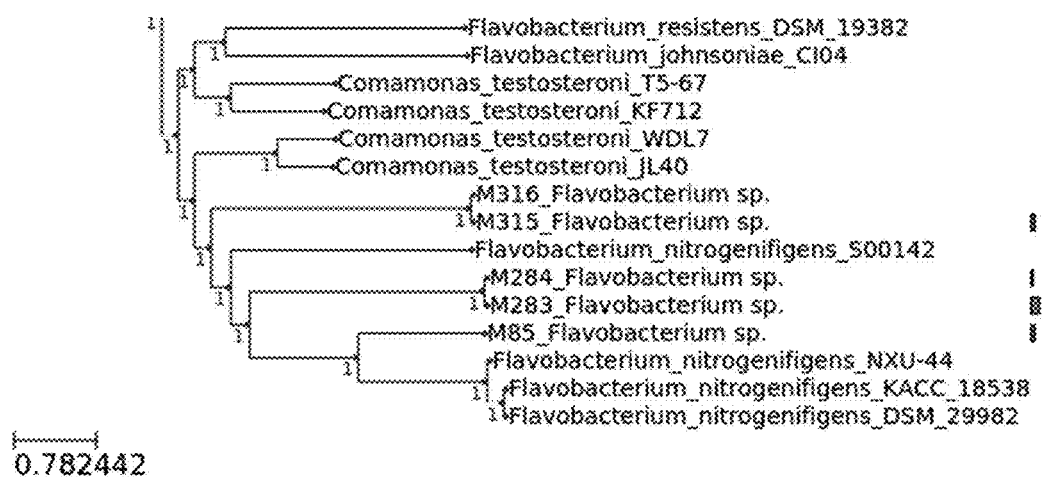

During the development of embodiments of the technology described herein, whole-genome phylogenetic trees were constructed using the whole genomes of the organisms tested for insecticidal activity and the whole genomes of related organisms. Related organisms were identified using complete genomes or chromosome assemblies available in the NCBI database and were chosen using 16S ribosomal RNA gene sequence or whole genome average nucleotide identity. FIG. 9 shows a phylogeny of organisms based on the presence and absence of genes. FIG. 10 is a phylogeny based on SNP variation in genes that were represented in at least 60% of the organisms. Both trees (FIG. 9 and FIG. 10) were built using PEPPAN v 1.0.5, which draws trees using a RapidNJ algorithm. The trees were visualized and annotated using the Environment for Tree Exploration (ETE) python package. In FIG. 9, the bars represent the average 72 hour mortality of *Aedes aegypti* following application of microbial cultures. Black bars represent *Aedes aegypti* mortality rates above 15%, and grey bars represent *Aedes aegypti* mortality rates below 15%. In FIG. 10, bars represent the average 72 hour mortality of *Aedes aegypti* following application of microbial cultures. Black bars represent *Aedes aegypti* mortality rates above 15%, and grey bars represent *Aedes aegypti* mortality rates below 15%.

Figure 11A:
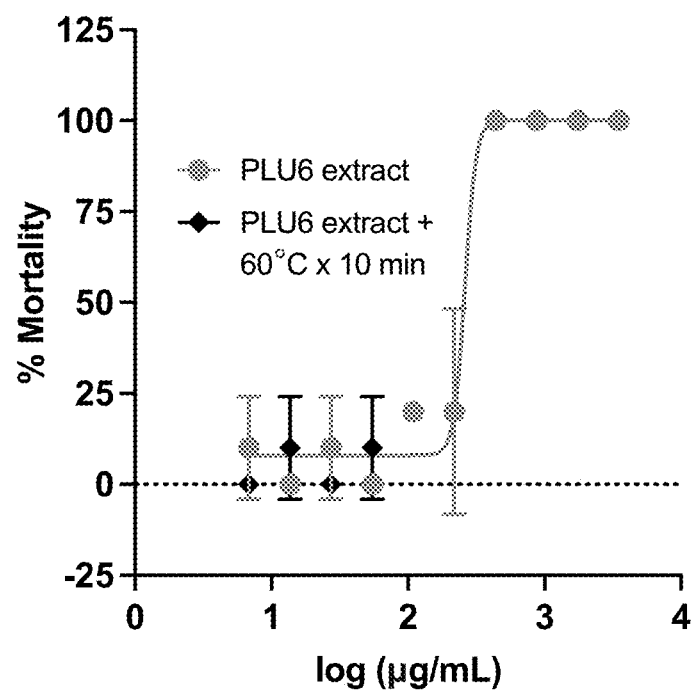
FIG. 11C shows preparative HPLC (210 nm and 254 nm) chromatograms of PLU6 ethyl acetate extract. Numbers on the chromatogram indicate fractions collected.
FIG. 11D shows a semipreparative HPLC (220 nm) chromatogram of fraction 19 indicated in FIG. 11C.
FIG. 11E is a comparison of the HPLC (210 nm) chromatograms of fractions 17-19 indicated in FIG. 11C of the PLU6 ethyl acetate extract (bottom trace) and an arundine (3,3'-diindolylmethane) standard (top trace).
FIG. 11F is a comparison of the $^1$H NMR (600 MHz, MeOD-$d_4$) spectra of fractions 17-19 indicated in FIG. 11C of the PLU6 ethyl acetate extract (bottom trace) and an arundine (3,3'-diindolylmethane) standard (top trace).
FIG. 11G is a mass spectrum of metabolite 2 described herein.
FIG. 11H is a tri-indole chemical structure of the metabolite 2 compound.
FIG. 11I is a mass spectrum of metabolite 3 described herein.
FIG. 11J is a tetra-indole chemical structure of the metabolite 3 compound.
Figure 11B:
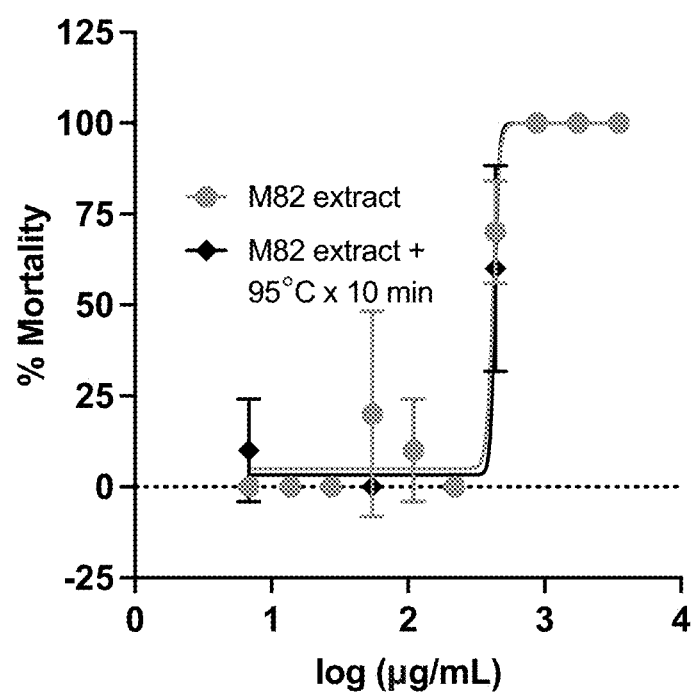
Figure 11C:
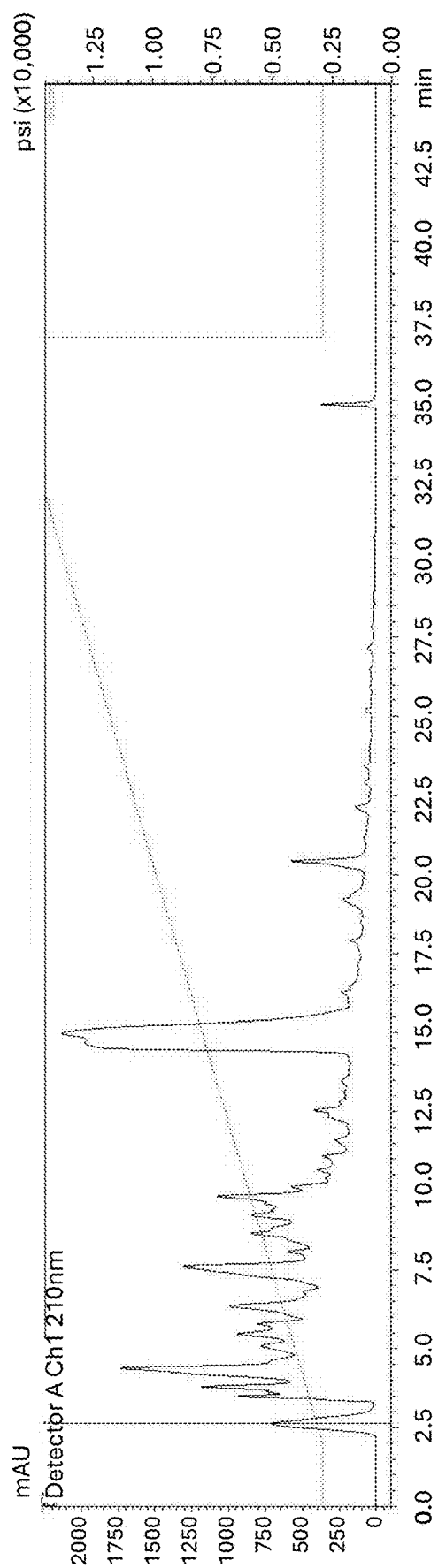
Figure 11D:
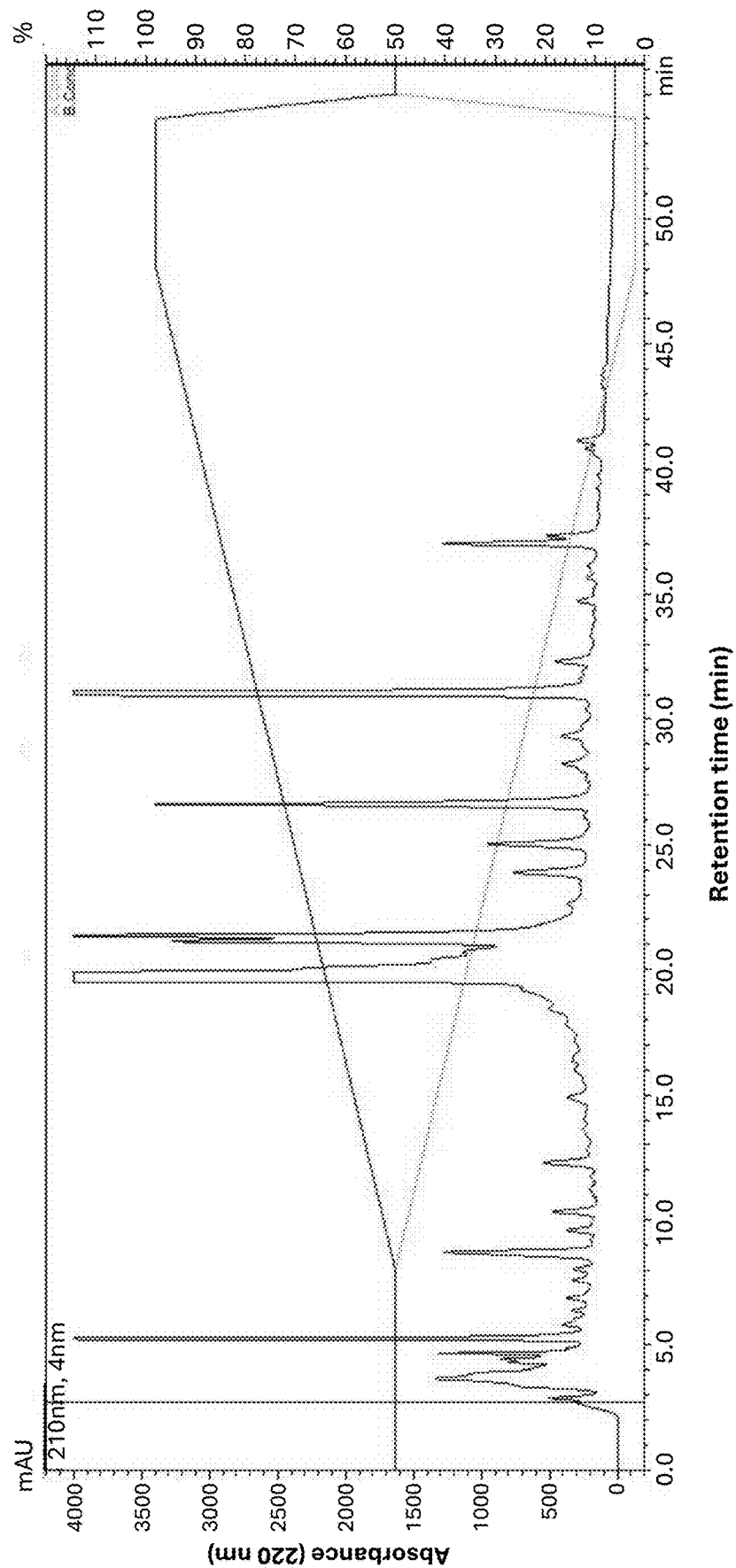
Figure 11E:
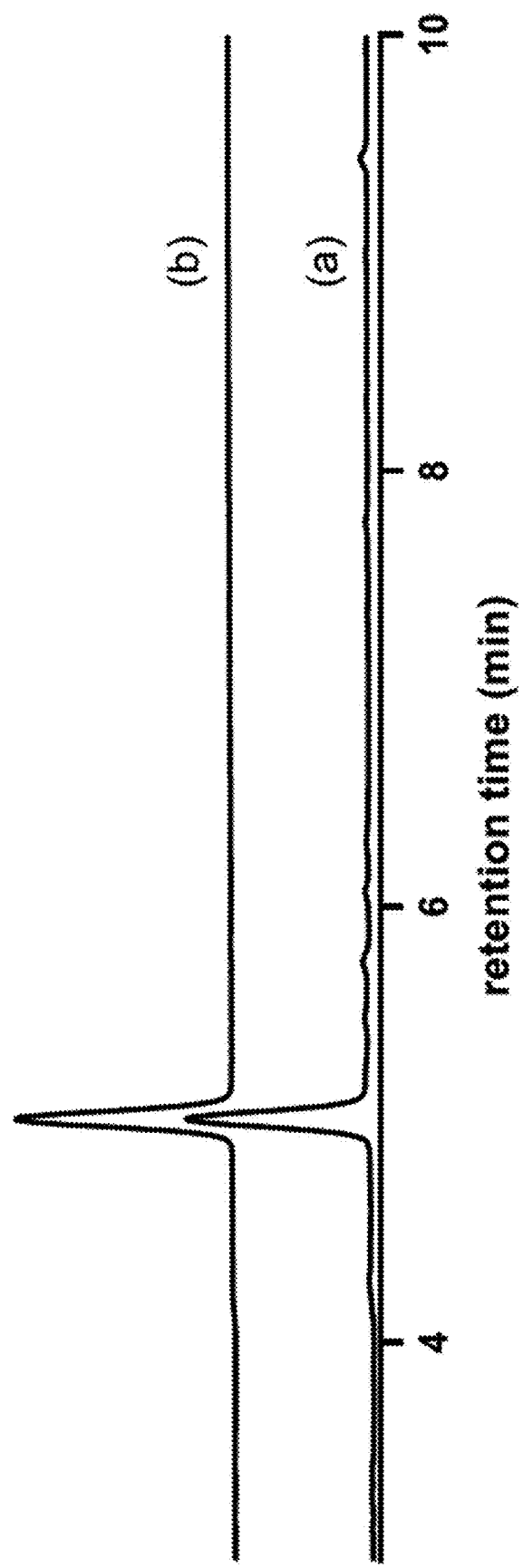
Figure 11F:
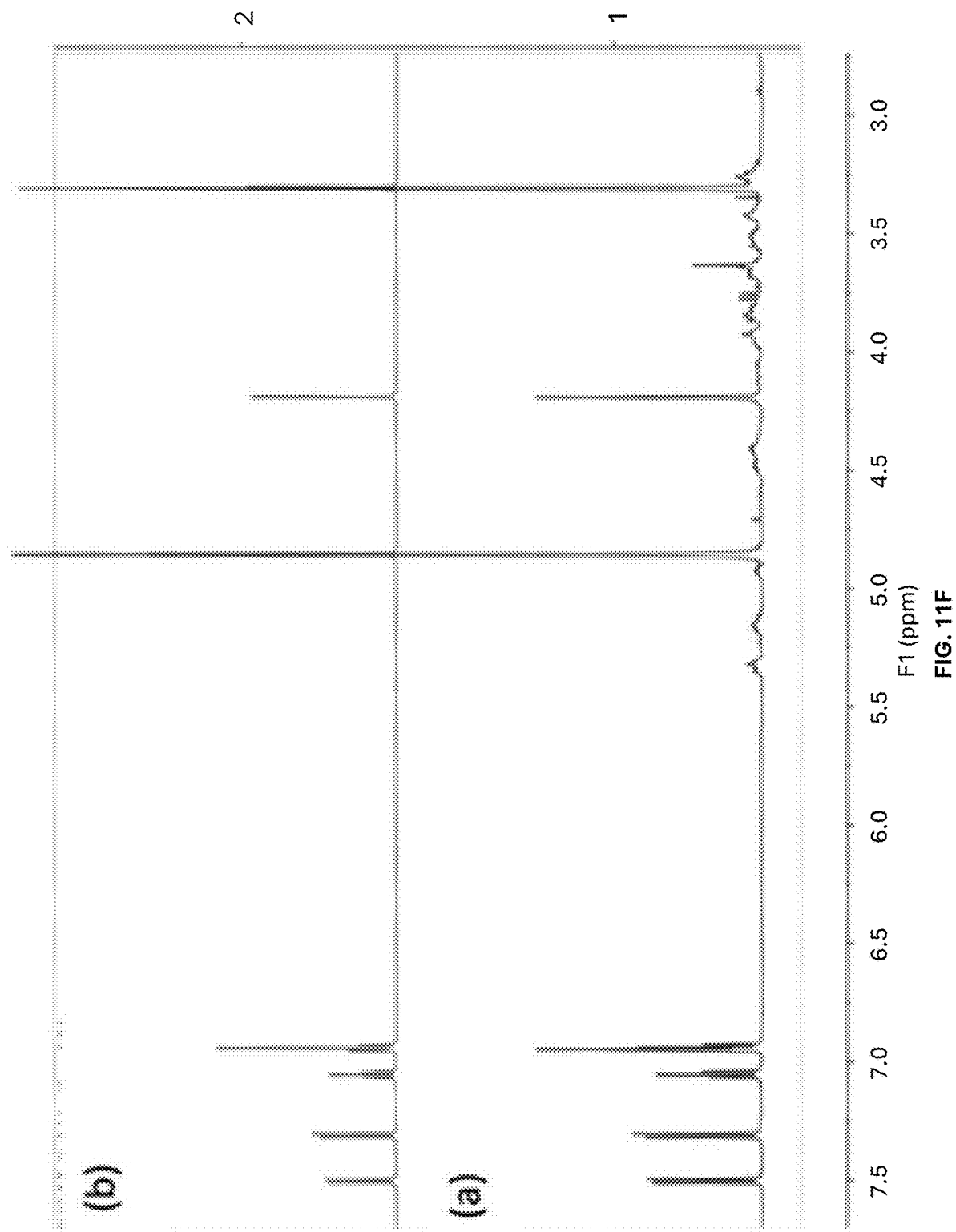

Upon extracting the common ancestors for the clades in which the killing (e.g., insecticidal (e.g., larvicidal)) activity was greater than 15%, all organisms identified as having killing activity (e.g., detected to cause insecticidal (e.g., larvicidal) mortality of at least 15%) have at least one coding region encoding a protein with at least 95% sequence identity across the entire length of SEQ ID NO: 1 (MKCIGJBJ_03627 DNA gyrase subunit A), at least 95% sequence identity across the entire length of SEQ ID NO: 2 (MKCIGJBJ_03079 DNA topoisomerase 1), at least 95% sequence identity across the entire length of SEQ ID NO: 3 (MKCIGJBJ_00500 DNA-directed RNA polymerase subunit beta), at least 95% sequence identity across the entire length of SEQ ID NO: 4 (MKCIGJBJ_00499 DNA-directed RNA polymerase subunit beta'), and/or at least 95% sequence identity across the entire length of SEQ ID NO: 5 (MKCIGJBJ_02095 DNA-directed RNA polymerase subunit alpha).

During the development of embodiments of the technology described herein, experiments were conducted to test the activity of organic extracts prepared from supernatants of PLU6 and M82 cultures against *Ae. aegypti* larvae (FIG. 11A and FIG. 11B). Data were collected indicating that small molecules (e.g., organic molecules) derived from cultures of two independent *Chryseobacterium* strain cultures (PLU6 and M82) displayed larvicidal activity. Activity of small molecule extracts were stable at 60° C. (FIG. 11A) and 95° C. (FIG. 11B), indicating that at least one active molecule in these extracts is heat stable. Further, data collected during these experiments indicated that the activity is dose-dependent. FIG. 11A and FIG. 11B show dose curves for PLU6 (FIG. 11A) and M82 (FIG. 11B) extracts applied to *Ae. aegypti* larvae. Mortality data were plotted against $\log_{10}$-transformed compound concentrations. Inhibitory dose-response curves were fitted using GraphPad Prism software. Error bars represent standard deviations calculated from two technical replicates (assay wells). The mean $LC_{50}$ s calculated for PLU6 extract and PLU6 extract treated at 60° C. for 10 minutes were 253±11 μg/mL and 249±17 μg/mL, respectively. The mean $LC_{50}$s calculated for M82 extract and M82 extract treated at 95° C. for 10 minutes were 340±113 μg/mL and 271±227 μg/mL, respectively. Standard deviations were calculated from two independent replicate dose curves for which the curve fit $R^2$ values were ≥0.75.

Furthermore, data indicated that extracts prepared from *Chryseobacterium* strains cause mortality in a variety of insects (e.g., across multiple taxonomic groups). In particular, treatment with extracts from *Chryseobacterium* strains causes mortality in cabbage looper (*Trichoplusia ni*) neonates (FIG. 12). Assay used N=16 larvae per concentration. The negative controls (no extract) displayed 0% mortality.

Further, during the development of embodiments of the technology described herein, experiments were conducted to isolate and characterize metabolites produced by PLU6. PLU6 was inoculated on NB agar and incubated for 2 days at 30° C. Seed cultures were prepared by inoculating 50 mL falcon tubes (31×), each containing NB broth medium (5 mL), with a single colony of the bacterial isolate and shaking at 200 rpm at 30° C. for one day. The seed culture (5 mL) was transferred into a 2.8 L unbaffled Fernbach flask containing 1 L (31×) of NB broth and incubatedat 200 rpm at 30° C. for two days. After incubation, an aliquot of methanol (100 mL) and 22 g of Amberlite XAD16N resin contained within a polypropylene mesh bag were added to each 1 L culture and incubated for 2 hours on a rotary shaker at 200 rpm. Resin bags were removed and washed with copious amounts of $H_2O$ to remove any water-soluble media components. The washed resin bags were then extracted with ethyl acetate (EtOAc), followed by methanol (MeOH). The organic fractions were combined and concentrated to dryness in vacuo to yield the crude extract. The crude extract was then subjected to liquid-liquid partitioning between EtOAc and $H_2O$. The EtOAc fraction was dried over anhydrous $Na_2SO_4$ and concentrated to dryness in vacuo to yield 1627 mg of product.

The EtOAc fraction was redissolved in MeOH and subjected to chromatographic fractionation (FIG. 11C) using preparative reversed-phase HPLC (Phenomenex Luna phenylhexyl, 21.2 mm×15 cm, 5 μm, 20 mL/min, isocratic elution with 80% $H_2O$/MeCN for 2 min followed by gradient elution from 80% $H_2O$/MeCN to 100% MeCN over 30 min then isocratic elution with 100% MeCN for 5 min) to yield 30 fractions. The preparative HPLC fractions (at concentrations of 200 μg/mL and 20 μg/mL) were tested against *Aedes aegypti*. Fractions 18-20 all showed 100% mortality at 72 hours at a concentration of 200 μg/mL. Fractions 18, 19, and 20 showed 80%, 100%, and 40% mortality, respectively, at 72 hours at a concentration of 20 μg/mL.

Fraction 19 was subjected to chromatographic purification using semipreparative reversed phase HPLC (Phenomenex Luna phenylhexyl, 10 mm×25 cm, 5 μm, 4 mL/min, isocratic elution with 50% $H_2O$/MeCN for 8 min followed by gradient elution from 50% $H_2O$/MeCN to 2% $H_2O$/MeCN over 40 min then isocratic elution with 2% $H_2O$/MeCN for 6 min). Chromatographic purification of Fraction 19 yielded several peaks (FIG. 11D). Fraction 17 (FIG. 11D) from the chromatographic purification of Fraction 19 identified above (FIG. 11C) was further characterized.

HPLC and $^1H$ NMR (MeOD-$d_4$) analysis of Fraction 17 (F17) showed the presence of a metabolite (1) as a principal component. Detailed analysis of NMR data suggested 1 to be arundine (3,3'-diindolylmethane), which was confirmed by comparing the HPLC profile and $^1$H NMR data of metabolite 1 with a commercial standard (FIGS. 11E and 11F).

Figure 11G:
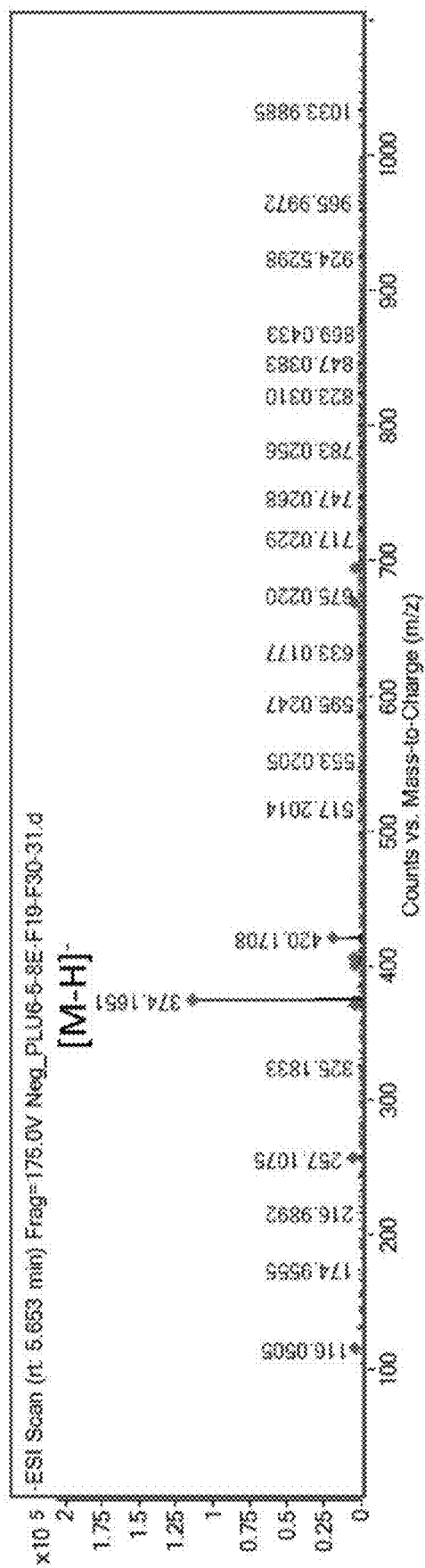
Figure 11H:
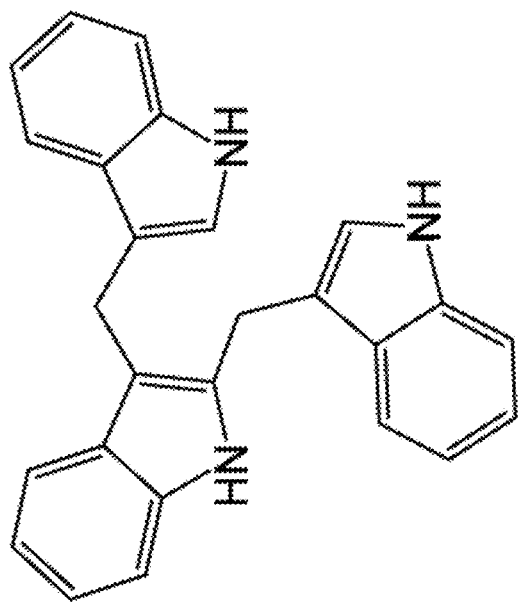

Fractions 30 and 31 from the chromatographic purification of Fraction 19 identified above (FIG. 11C) were pooled and further characterized, and a second metabolite (metabolite 2) was identified. HRESI(−)MS analysis of 2 revealed a quasi-molecular ion ([M-H]$^-$) corresponding to a molecular formula $C_{26}H_{21}N_3$ (Δppm −3.1) (FIG. 11G). The UV-vis spectrum indicated the presence of an indole chromophore and was quite similar to arundine. $^1$H and 2D HSQC NMR analysis suggested the structure of 2 to be an indole trimer as shown in FIG. 11H.

Figure 11I:
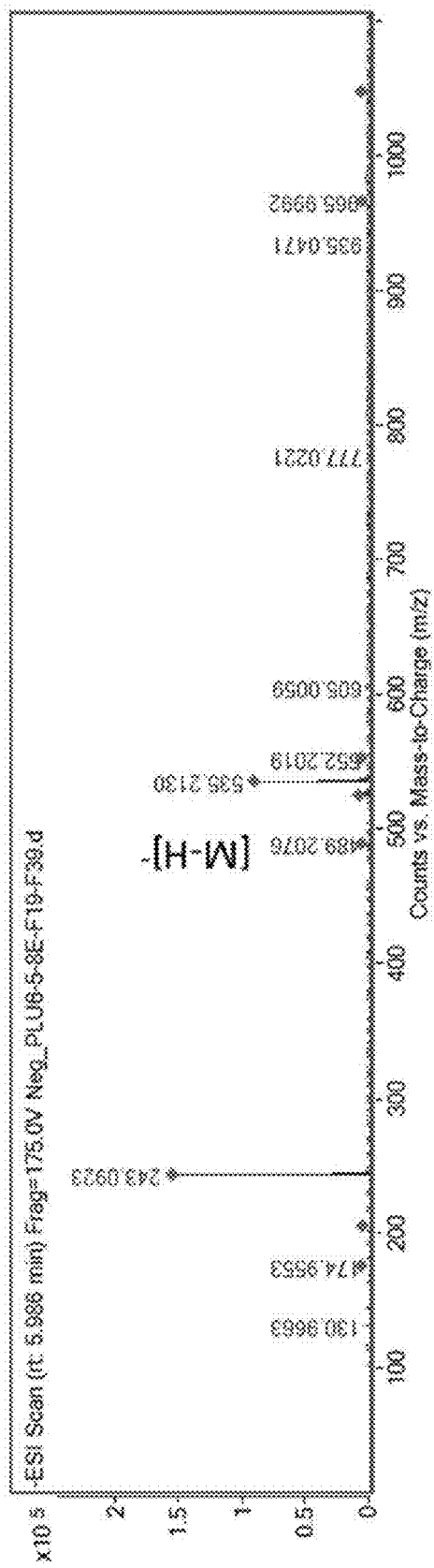
Figure 11J:
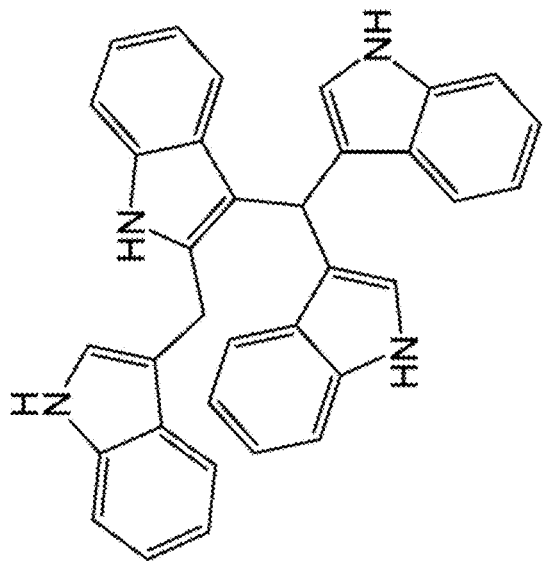

Fraction 39 from the chromatographic purification of Fraction 19 identified above (FIG. 11C) was characterized and a metabolite was identified in this fraction (metabolite 3). HRESI(−)MS analysis of 3 revealed a quasi-molecular ion ([M-H]−) corresponding to a molecular formula $C_{34}H_{26}N_4$ (Δppm −1.78) (FIG. 11I). The UV-vis spectrum indicated the presence of an indole chromophore and was quite similar to arundine. $^1$H and 2D HSQC NMR analysis suggested the structure to be an indole trimer as shown in FIG. 11J.

During the development of embodiments of the technology described herein, experiments were conducted to test the larvicidal activity of metabolites 1-3 against *Aedes aegypti*. Data collected during these experiments indicated that metabolites 2 and 3 (e.g., the tri-indole and tetra-indole compounds, respectively, as shown in FIGS. 11H and 11J, respectively) did not kill larvae at a concentration up to 80 μg/mL. However, diindole compounds (e.g., arundine (1)) exhibited larvicidal activity against *Ae. aegypti*.

In particular, data indicated that a diindole compound (e.g., 3,3'-diindolylmethane) produced by PLU6 is active against *Aedes aegypti* larvae in a dose-dependent manner (FIG. 13). To produce a dose curve, the compound 3,3'-diindolylmethane was applied to *Ae. aegypti* larvae, mortality data were collected, the mortality data were plotted against $\log_{10}$-transformed compound concentrations, and an inhibitory dose-response curve was fitted using GraphPad Prism software (FIG. 13). The representative curve fit shown corresponds to a 3,3'-diindolylmethane $LC_{50}$ of 10.2 μg/mL (95% CI [7.3, 14.2]). Error bars represent standard deviations calculated from four technical replicates (assay wells). The mean $LC_{50}$ calculated for 3,3'-diindolylmethane was 7.5±3.0 μg/mL (standard deviation calculated from five independent replicate dose curves for which the curve fit $R^2$ values were ≥0.75. Significant outlier $LC_{50}$ values were identified using Grubb's test with P<0.01 and were not included in calculating the mean $LC_{50}$). Mortality in the negative control was not subtracted but was <10% for all assays.

Further, data indicated that the diindole compound (e.g., 3,3'-diindolylmethane) produced by strain PLU6 is active against *Culex quinquefasciatus* larvae in a dose-dependent manner (FIG. 14). To produce a dose curve, the compound 3,3'-diindolylmethane was applied to *C. quinquefasciatus* larvae, mortality data were collected, the mortality data were plotted against $\log_{10}$-transformed compound concentrations, and an inhibitory dose-response curve was fitted using GraphPad Prism software (FIG. 14). The representative curve fit shown corresponds to a 3,3'-diindolylmethane $LC_{50}$ of 7.5 μg/mL (95% CI [4.5, 13.3]). Error bars represent standard deviations calculated from four technical replicates (assay wells). Mortality in the negative control was 0%.

Further, 3,3'-diindolylmethane is active against *Spodoptera frugiperda*, *Trichoplusia ni*, and *Heliothis virescens* in a dose-dependent manner. Experiments were conducted in which mortality of lepidopteran larvae was measured after 7 days of diet overlay treatment with 3,3'-diindolylmethane at the concentrations indicated in Table 3. Mean mortalities and standard deviations were calculated from three independent experiments (each N=16). For each experiment, mortalities were corrected using Abbott's formula (Abbott (1987) "Method of computing the effectiveness of an insecticide" J. American Mosquito Control Association 2: 302-03, incorporated herein by reference). For all species except *Plutella xylostella*, neonates were used. For *P. xylostella*, third instar larvae were used. The positive control used was 1000 ppm of *Bacillus thuringiensis* kurstaki.

TABLE 3

Activity of 3,3'-Diindolylmethane against lepidoptera

| Treatment | Spodoptera frugiperda (fall armyworm) | Trichoplusia ni (cabbage looper) | Ostrinia nubilalis (European corn borer) | Heliothis virescens (tobacco budworm) | Plutella xylostella (diamondback moth) |
|---|---|---|---|---|---|
| 2500 μg/mL | 95.70 ± 3.73% | 93.25 ± 6.90% | 4.17 ± 3.61% | 83.33 ± 14.43% | 43.35 ± 15.85% |
| 625 μg/mL | 85.08 ± 3.85% | 44.60 ± 26.25% | 6.25 ± 6.25% | 93.75 ± 6.25% | 15.72 ± 5.24% |
| 156.25 μg/mL | 79.03 ± 25.96% | 22.95 ± 23.12% | 4.17 ± 3.61% | 85.15 ± 13.34% | 7.39 ± 1.98% |
| 39.06 μg/mL | 2.15 ± 6.71% | 3.00 ± 13.24% | 2.08 ± 3.61% | 40.93 ± 35.89% | 1.07 ± 1.86% |
| 9.77 μg/mL | 4.10 ± 12.69% | −1.15 ± 3.79% | 2.08 ± 3.61% | 3.16 ± 3.13% | 1.01 ± 4.82% |
| 0 μg/mL | 2.15 ± 6.71% | 8.04 ± 14.31% | 4.17 ± 7.22% | 11.69 ± 11.31% | 1.01 ± 4.82% |
| positive control | 100.00 ± 0.00% | 100.00 ± 0.00% | 100.00 ± 0.00% | 100.00 ± 0.00% | 100.00 ± 0.00% |
| negative control | 0.00 ± 0.00% | 0.00 ± 0.00% | 0.00 ± 0.00% | 0.00 ± 0.00% | 0.00 ± 0.00% |

Further, 3,3'-Diindolylmethane displays activity against a variety of lepidopteran species in a dose-dependent manner (Table 4). In Table 4, species abbreviations are as follows: CM, *Cydia pomonella* (codling moth); ECB, *Ostrinia nubilalis* (European corn borer); SCB, *Diatraea saccharalis* (sugarcane borer); SWCB, *Diatraea grandiosella* (southwestern corn borer); CL, *Trichoplusia ni* (cabbage looper); BAW, *Spodoptera exigua* (beet armyworm); DBM, *Plutella xylostella* (diamondback moth); SBL, *Chrysodeixis includens* (soybean looper); VBC, *Anticarsia gemmatalis* (velvetbean caterpillar); CEW, *Helicoverpa zea* (corn earworm); BCW, *Agrotis ipsilon* (black cutworm); SAW, *Spodoptera eridania* (southern armyworm); TBW, *Chloridia virescens* (tobacco budworm); and FAW, *Spodoptera frugiperda* (fall armyworm). Activity is low or not observed in several species, including *O. nubilalis*, *P. xylostella*, and *A. ipsilon*, which indicates that 3,3'-diindolylmethane displays species specificity in its activity.

TABLE 4

Activity of 3,3'-Diindolylmethane

| | Mortalities (%) after 7 days of treatment (Abbott's Correction) | | | | | | |
|---|---|---|---|---|---|---|---|
| Treatment | CM | ECB | SCB | SWCB | CL | BAW | DBM |
| 2500 μg/mL | 39.3 | −7.7 | 100.0 | 83.3 | 93.1 | 71.9 | 19.4 |
| 625 μg/mL | 50.0 | −15.4 | 100.0 | 90.0 | 72.4 | 93.8 | 6.5 |
| 156.25 μg/mL | 21.4 | −23.1 | 100.0 | 46.7 | 41.4 | 71.9 | 19.4 |
| 0 μg/mL | −7.1 | −15.4 | 27.6 | 13.3 | 10.3 | 12.5 | 0.0 |

TABLE 4-continued

Activity of 3,3'-Diindolylmethane

| | | | | | | | |
|---|---|---|---|---|---|---|---|
| positive control | 100.0 | 100.0 | 100.0 | 100.0 | 100.0 | 100.0 | 100.0 |
| negative control | 0.0 | 0.0 | 0.0 | 0.0 | 0.0 | 0.0 | 0.0 |

| | Mortalities (%) after 7 days of treatment (Abbott's Correction) | | | | | | |
|---|---|---|---|---|---|---|---|
| Treatment | SBL | VBC | CEW | BCW | SAW | TBW | FAW |
| 2500 µg/mL | 80.0 | 96.7 | 90.6 | 20.0 | 100.0 | 87.1 | 96.7 |
| 625 µg/mL | 50.0 | 70.0 | 50.0 | 26.7 | 100.0 | 74.2 | 63.3 |
| 156.25 µg/mL | 26.7 | 100.0 | 40.6 | 0.0 | 22.6 | 74.2 | 40.0 |
| 0 ug/mL | −6.7 | 10.0 | 9.4 | −3.3 | 9.7 | 3.2 | 3.3 |
| positive control | 100.0 | 100.0 | 100.0 | 100.0 | 100.0 | 100.0 | 100.0 |
| negative control | 0.0 | 0.0 | 0.0 | 0.0 | 0.0 | 0.0 | 0.0 |

During the development of embodiments of the technology described herein, experiments were conducted to assess the dose-dependent activity of 3,3'-diindolylmethane against lepidopteran species. Data collected indicated that 3,3'-diindolylmethane is active against *Trichoplusia ni* (cabbage looper), *Spodoptera exigua* (beet armyworm), *Chloridia virescens* (tobacco budworm), *Spodoptera frugiperda* (fall armyworm), and *Anticarsia gemmatalis* (velvetbean caterpillar) in a dose-dependent manner (FIG. 15). Data were obtained from bioassay measurements performed with N=32 neonates in a diet overlay format. Data are corrected using Abbott's Correction. Positive control samples (1000 ppm *Bacillus thuringiensis kurstaki*) produced 100% mortality for all five species.

Figure 17:
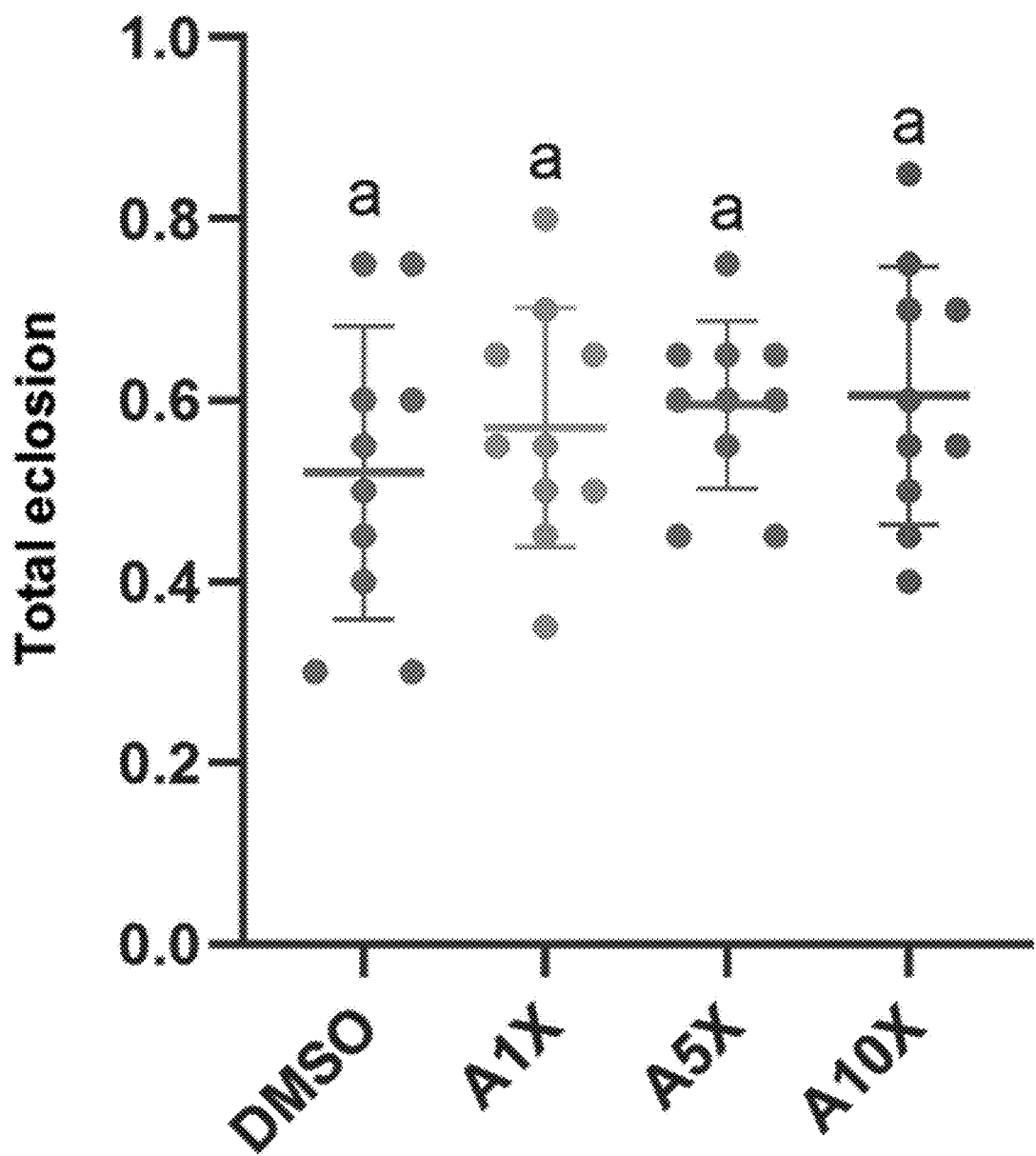
Figure 18:
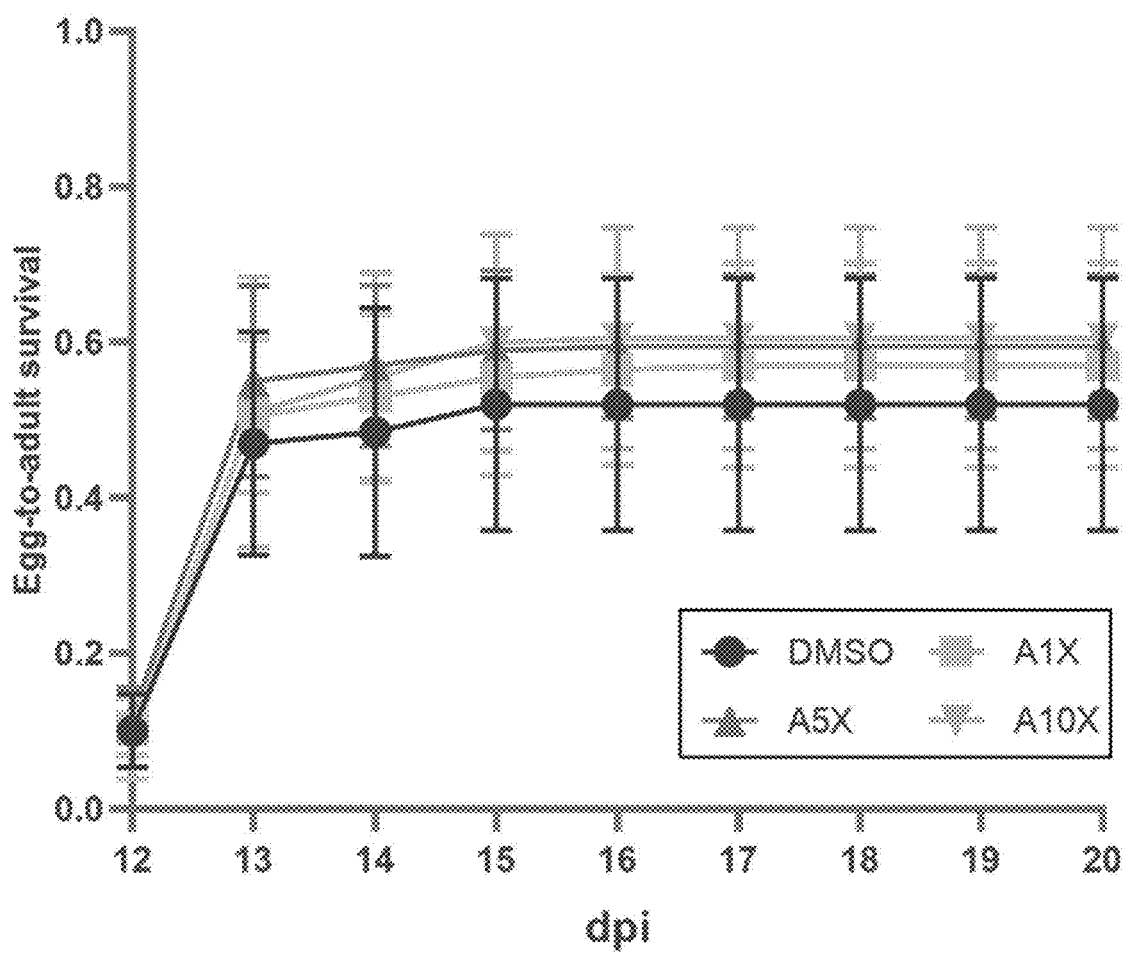

During the development of embodiments of the technology described herein, experiments were conducted to assess the activity of 3,3'-diindolylmethane against *Drosophila suzukii*. Data collected indicated that the pupation rate of *Drosophila suzukii* (spotted wing *Drosophila*) was not affected by 3,3'-diindolylmethane treatment when added to diet (FIG. 16). A1X=100 µg/mL; A5X=500 µg/mL; A10X=1000 µg/mL. Each concentration was tested with 10 vials containing 20 *D. suzukii* L2 larvae. Pupation rates were not significantly different, as measured by a one-way ANOVA (alpha=0.05). Further, data collected indicated that the eclosion rate of *Drosophila suzukii* (spotted wing *Drosophila*) was not affected by 3,3'-diindolylmethane treatment when added to diet (FIG. 17). A1X=100 µg/mL; A5X=500 µg/mL; A10X=1000 µg/mL. Each concentration was tested with 10 vials containing 20 *D. suzukii* L2 larvae. Treatments labeled with the same letter are not significantly different, as measured by a one-way ANOVA (alpha=0.05). And, data collected indicated that the egg-to-adult survival of *Drosophila suzukii* (spotted wing *Drosophila*) was not affected by 3,3'-diindolylmethane treatment when added to diet (FIG. 18). A1X=100 µg/mL; A5X=500 µg/mL; A10X=1000 µg/mL. Each concentration was tested with 10 vials containing 20 *D. suzukii* L2 larvae. "Dpi" indicates days post infestation (0 dpi is the day of egg-laying). Accordingly, as shown by FIGS. 16, 17, and 18, 3,3'-diindolylmethane did not display insecticidal activity against the agricultural pest spotted wing *Drosophila*, indicating that the compound is specific for certain insect targets.

Figure 19:
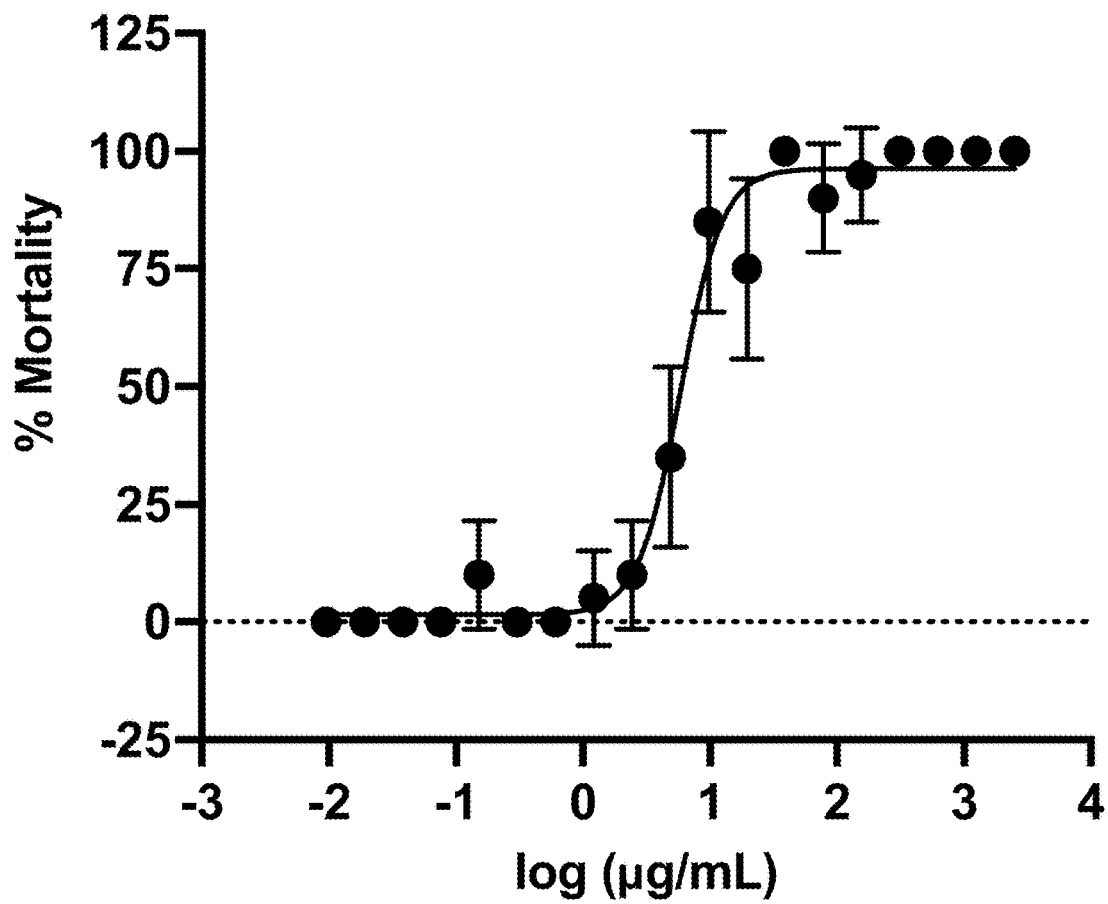

During the development of embodiments of the technology described herein, experiments were conducted to test the activity of a synthetic diindole compound (e.g., 3-((1H-indol-2-yl)methyl)-1H-indole) against *Aedes aegypti* larvae. Data collected indicated that 3-((1H-indol-2-yl)methyl)-1H-indole exhibits larvicidal activity against *Ae. aegypti* in a dose-dependent manner (FIG. 19). FIG. 19 shows a representative dose curve for 3-((1H-indol-2-yl)methyl)-1H-indole applied to *Ae. aegypti* larvae. Mortality data were plotted against $\log_{10}$-transformed compound concentrations. An inhibitory dose-response curve was fitted using GraphPad Prism software. The representative curve fit shown corresponds to a 3-((1H-indol-2-yl)methyl)-1H-indole $LC_{50}$ of 5.8 µg/mL (95% CI [5.1, 6.8]). Error bars represent standard deviations calculated from four technical replicates (assay wells). The mean $LC_{50}$ calculated for 3-((1H-indol-2-yl)methyl)-1H-indole was 6.3±2.1 µg/mL (standard deviation was calculated from four independent replicate dose curves for which the curve fit $R^2$ values were ≥0.75. Significant outlier $LC_{50}$ values were identified using Grubb's test with P<0.01 and were not included in calculating the mean $LC_{50}$). Mortality in the negative control was not subtracted but was <10% for all assays.

Figure 20:
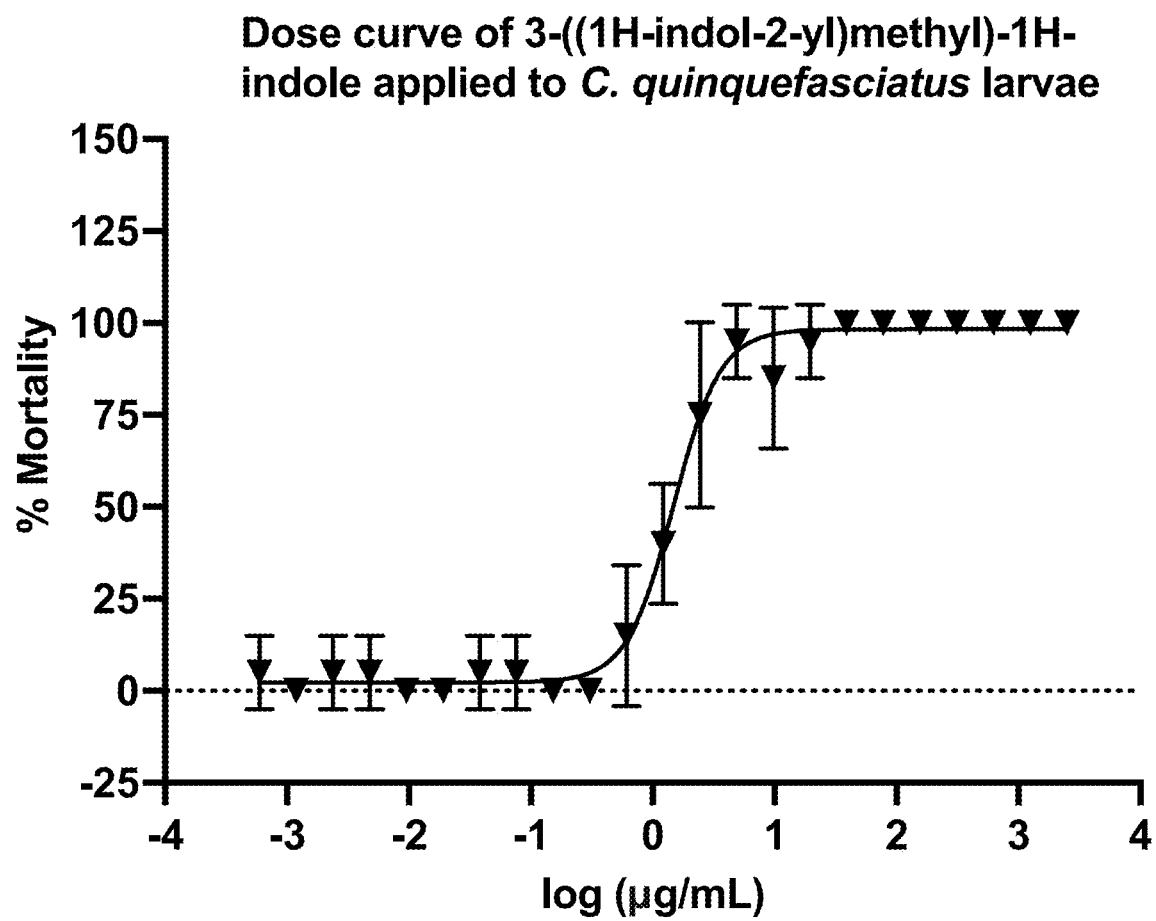

Further, experiments were conducted to test the activity of the synthetic diindole compound (e.g., 3-((1H-indol-2-yl)methyl)-1H-indole) against *Culex quinquefasciatus* larvae. The data collected indicated that 3-((1H-Indol-2-yl)methyl)-1H-indole exhibits larvicidal activity against *C. quinquefasciatus* in a dose-dependent manner (FIG. 20). FIG. 20 shows a representative dose curve for 3-((1H-indol-2-yl)methyl)-1H-indole applied to *C. quinquefasciatus* larvae. Mortality data were plotted against $\log_{10}$-transformed compound concentrations. An inhibitory dose-response curve was fitted using GraphPad Prism software. The representative curve fit shown corresponds to a 3-((1H-indol-2-yl)methyl)-1H-indole $LC_{50}$ of 1.5 µg/mL (95% CI [1.3, 1.7]). Error bars represent standard deviations calculated from four technical replicates (assay wells). The mean $LC_{50}$ calculated for 3-((1H-indol-2-yl)methyl)-1H-indole was 0.95±0.75 µg/mL (standard deviation calculated from two independent replicate dose curves for which the curve fit $R^2$ values were ≥0.75. Mortality in the negative control was not subtracted but was <10% for all assays.

Figure 21:
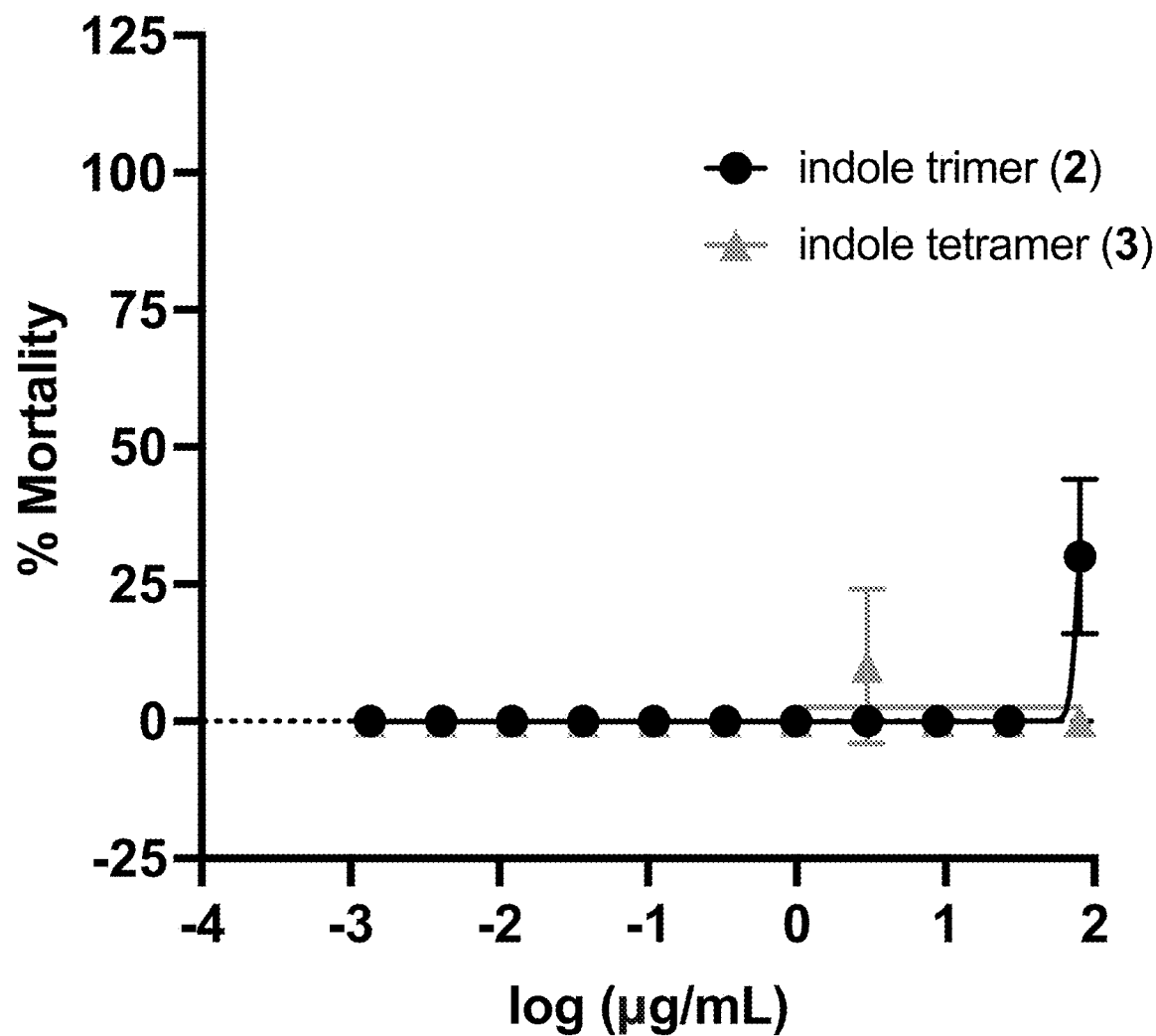

During the development of embodiments of the technology described herein, experiments were conducted to test the activity of indole trimer and indole tetramer compounds shown in FIG. 11H and FIG. 11J, respectively, against *Ae. aegypti*. Data collected indicated that the tri-indole and tetra-indole compounds have no activity against *Aedes aegypti* larvae compared to diindole compounds (FIG. 21). Error bars represent standard deviations calculated from two technical replicates (assay wells). Thus, indole compounds having more than two indole groups do not display activity in an *Ae. aegypti* bioassay, indicating that the diindole structure is important for killing activity.

The breadth and scope of the present disclosure should not be limited by any of the above-described exemplary embodiments, but should be defined only in accordance with the following claims and their equivalents. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

>MKCIGJBJ_03627 DNA gyrase subunit A
SEQ ID NO: 1
MTTEEYSHEGESLKKVSGLYKDWFLDYASYVILDR
AIPSIYDGLKPVQRRIMHSMRELEDGRYNKVANIV
GNTMKYHPHGDASITDAMVQIGQKELLIDTQGNWG
NIYTGDSAAAARYIEARLTPFALEVVFNPKTTEWT
KSYDGRNNEPIDLPVKFPLLLAQGVEGIGVGLSTK
ILPHNFNELINASVAYLKGKKFELYPDFLTAGYLD
VSEYNDGHRGGKVRARAKITQTDKHTLVISELPYS
KTTTDLIDSILKANEKGKIKIKKIEDNTSDKVEIL
IHIHNDVSPDKTIDALYAFTDCQVTISPNACVIVG
DKPMFMNVSEILKMNTDHTVSLLKKELEIELHELQ
ESWHFSSLERIFIENRIYHDIEEVKTWEDVLKTID
AGLKPHTKHLLRAVTEEDILKLTEIRIKRISRFDL
DKFKENIASLEGKIEQVKYNLENLIAYAIDYYLNI
QKKYGKDKQRRTELRIFDTIDATKVAVANEKFYAN
FEEGFIGTSLKKDQYLFDCSDIDDIITFRKDGSMK
VVKVEAKTFIGKDILHVAVWKKNDKRTVYNMIYRE
GREGPYYMKRFSVTGVTRNTDYPLASDKKGSETLY
FSANPNGEAETVTVLLKPNPRIRKNKMEINFSDLA
IKGRDSKGNLVTKYAVKKVDLKEEGVSTLAPRKIW
PDDTVRRLNADARGTLLGSFKGDDKILTINTNGEV
KLVSFDLGNRFDDEYLVLEKWKPEQPITCIYYDGE
KDIYFIKRFLLENTVNVQTFMPSEHPKSFIENVIV
ANDATAEIIFAKDKGKEREPEVVNIDEFIAVKGIK
AIGNQFTKFKVKAINITIPEPVEEEPEAYEDPEPT
GDLDEDGGMIGDLFQDDGNNENE >MKCIGJBJ_03079 DNA topoisomerase 1
SEQ ID NO: 2
MSKNLVIVESPAKAKTIQKYLGKDFEVKSSFGHIR
DLPKKGMGIDLATFNPDYEVSADKKKLVTELKAAV
KKADMVWLASDEDREGEAIAWHLADELKLKPENRK
RIVFHEITKNAILKAIDNPRDIDQNLVNAQQARRV
LDRIVGFEMSPVLWKKVKPGLSAGRVQSVAVRLIV
EREKEIREFIPKASFKLDGIFLNKTEQEIAAKLKK
DFEKEEDAEKFLEQAKTTEFKVLNVETKPGTRSAS
APFTTSTLQQEASSRLGYNVTNTMRLAQRLYEEGY
ITYMRTDSVNLSQEAIEGAKKQIISEYGTEYSSPR
NYTTKSASAQEAHEAIRPTDFGVKSIGDAQLNKLY
QLIYRRTLASQMANAKIEKTVIEIGNTSLPHHFEA
QGEVIIFDGFLKAYGIVKTEDDDEENNDKLLPKVS
VGEVLSYKTITATEKFTRPSARYTEAGLVRKLEEL
GIGRPSTYAPTIQTIQNREYVDKREIEPQTREVIK MSLVKDKIKKVVLEEKFGGDKNKFVPTDIGEVVND
FLTDNFREILDYGFTARVEESFDEIASGDQKWKEM
MTNFYSKFHPRIEDVEENADRATGDRLLGVDPKTG
KNVHARIGRFGAMIQIGETDDEEKPIFASLMAGQN
IATITFEEALELFKLPFDLNTVDGQPVSVGVGRFG
PYVKWGETYISIPKGEDPLSVDQKRAEEIISEKKI
ADAPIATYKGEPVTKGSGRFGPFIKYKDIFVNVPK
RYDFENLSQSDINELIDAKLEKEANRYIQQWEKEK
ISIENGRWGPFIKFGKAMFKIPKKADDTKYEAEEL
KELSLDEVKKWITDQDPKAFAEKKKPAAKKATTTK
KTTAAKKPAAKKK >MKCIGJBJ_00500 DNA-directed RNA
polymerase subunit beta
SEQ ID NO: 3
MSKTKSTTQGNPRINFSSAKGKIITPDFLDIQIES
FREFFQLDTLPEARKTEALYKTFQENFPITDSRNQ
FVLEFLDYLVDSPRYSIDECVERGLTYSVPLKARL
KLYCTDPEHEDFQTVVQDVYLGPVPYMTPSGSFII
NGAERVIVTQLHRSPGVFFGQTYHANGTKLYYSRI
IPFKGSWMEFTTDINSVMYAYIDRKKKLPTTLLR
AIGYESDKDILQIFDLAEEVKVSKAALKKVEGRTL
AARVLNTWFEDFVDEDTGEVVSIERNEIILDRETI
LEKEHLDLILDAGVKSILIHKENSNEFSIIQNTLQ
KDPTNSEKEAVEYIYRQLRNADPPDEETARGIIEK
LFFSEQRYSLGEVGRYRLNKKLGLNIPTTTEVLTK
EDIIAIVRHLIELVNSKAEVDDIDHLSNRRIKTVG
EQLAGQFGVGLSRIARTIKERMNVRDNEIFTPLDL
VNAKTLTSVINSFFGTNQLSQFMDQTNPLSEITHK
RRLSALGPGGLSRERAGFEVRDVHHTHYGRICPIE
TPEGPNIGLISSLGIYAKINNLGFIETPYRKVEGG
KVDLNADPIYLNAEDEEAKVIAQANVELSDNGDFE
TDRIIARLDGDYPVVEPNQVDLIDVAPNQISGISA
SLIPFLEHDDANRALMGSNMMRQAVPLLKPQAPIV
GTGLEQQVARDSRILINAEGTGTVQYVDADKIVIK
YERSEDEDLVQFESATKTYNLTKFRKTNQSTTITL
RPNVRVGDVVEKGQVLCDGYATEKGELALGRNLVV
AFMPWKGYNFEDAIVINEKVVREDWFTSIHVDEYS
LEVRDTKLGMEELTADIPNVSEEATKDLDENGMIR
IGAEVKPGDIMIGKITPKGESDPTPEEKLLRAIFG
DKAGDVKDASLKADSSLRGVVINKKLFSRNIKDKK
KRTEEKLKLEEIENTYKAKFDELRNTLIEKLNTLV
SGKTSQGVHNDLDEEIIGKGVKFTHKLLTSVEDYV -continued

NVSGSDWTVDADKNELIKQLIHNYKIKYNDIQGVK

NREKFAISIGDELPAGIMKLAKVYIAKKRKLNVGD

KMAGRHGNKGIVSRIVREEDMPFLEDGTPVDIVLN

PLGVPSRMNIGQIYETVLGWAGQKLGMKFATPIFD

GATLDQITEYTDKAGLPKFGHTYLYDGGTGERFTQ

AATVGVIYMLKLGHMVDDKMHARSIGPYSLITQQP

LGGKAQFGGQRFGEMEVWALEAFGASNILREILTV

KSDDVIGRAKTYEAIAKGESMPEPGIPESFNVLLH

ELQGLGLDVRLEE

>MKCIGJBJ_00499 DNA-directed RNA polymerase subunit beta'
SEQ ID NO: 4
MSNKNKSSRFNKITIGLASPESILQDSRGEVLKPE

TINYRTHKPERDGLFCEKIFGPVKDYECACGKYKR

IRYKGIVCDRCGVEVTEKKVRRERIGHINLVVPIA

HIWYFRSLPNKIGYLLGIPSKKLDMIIYYERYVVI

QQGIAKKLDGSDFENMEFLTEEEYLDIMETLPVEN

QYLDDSDPNKFIARMGAEAVEDLLKRIDLDALSFD

LRHKAHNEGSKQRRTEALKRLNVVEALRGANTRMI

NRPEWMIMRVLPVIPPELRPLVPLDGGRFATSDLN

DLYRRVIIRNNRLKRLLEIKAPEVILRNEKRMLQE

SVDSLFDNTRKSSAVKSESNRPLKSLSDSLKGKQG

RFRQNLLGKRVDYSARSVIVVGPNLQLHECGIPKD

MAAELYKPFIIRKLIERGIVKTVKSAKRIIDRKEP

VVYDILENVMKGHPVLLNRAPTLHRLGIQAFQPKM

IEGKAIQLHPLVTTAFNADFDGDQMAVHLPLGPEA

ILEAQLLMLGSQNILNPANGSPITVPSQDMVLGLY

FMTKELSSTETMKVKGEGLAFYSPEEAEIAYAEGK

VSLNAKVRCKLPVKENGEIVTRLIETTVGRILFNQ

IVPKQVGYINELLTKKSLRNVIGKILADTDFPTTV

KFLDAMKDLGYSNAFKGGLSFSLGDIVVPVEKKQM

IAQSIETVDEIRANYNMGLITDTERYNQVIDVWTN

TNAGLTEMIMSRMKTDQGGFNSVYMMLDSGARGSK

EQIRQLSGMRGLMAKPQKAGSTGAEIIENPILANF

KEGLSILEYFISTHGARKGLADTALKTADAGYLTR

RLVDVAQDVIVTEDDCGTLRGTEVTALKKNDEIVE

KISERILGRVSLHNVYDPETDELITEADQVITEQL

AKRIEEAGLEAVEVRSPLTCEAKKGICAKCYGRNL

ATGKMIHMGEAVGVIAAQSIGEPGTQLTLRTFHQG

GTAGNVSENPSIVARRDGIVEMDEVRTITSEDENG

NTAEVVVSRSTEFRLVADNESRTPLMVANVPYGSI

LSVKPGDKVKKGDTICRWDPYNAVIIAETSGKVEY

EDIIQGISFQLEIDEQTGFEEKVISESRNKKAVPT

LKVVDSKGVEQKAYNLPVGAHLMVNDGEKIKAGKV

LIKIPRKSAKAGDITGGLPRVTELFEARNPSNPAV

VTEIDGVVSYGKIKRGNRELIVEAKTGERKIYLVK

LSNQILVQENDFVRAGSPLSDGSITPEDILRIKGP

TAVQEYLVNEIQEVYRLQGVKIDDKHFEIIVRQMM

TKVSIVDGGDTQFLEGALEHKYDFLEENNRVFGLK

VVVDAGDSKEFKPGQMITARELRDENSKLKREDLA

LVEVREALPATATPVLQGITRAALQTKSFMSAASF

QETTKVLNEAAVAGKIDDLNGLKENVIVGHRIPAG

TGLKEYQNVIVGSKKEFEDLN

>MKCIGJBJ_02095 DNA-directed RNA polymerase subunit alpha
SEQ ID NO: 5
MAILQFIKPDKVILLNSDEFKGQFEFRPLEPGFGL

TIGNALRRVLLSSLEGYAISSIKIEGVEHEFSTIP

GVIEDVTEIILNLKQVRLKAAAEGQANEQVVAKVS

GQTVITAGDLGKSINGFEVLNPDLVICNLNTDVTF

EITFNIEKGRGYVPSEQNKSNNAPVGTIAIDSIFT

PIKKVQYSIENYRVEQKTDYEKLVLDIETDGSISP

QNALTEASKILIYHFMLFSDERITLETEAVKASIQ

YDEETLHTRQLLKSKLADMDLSVRALNCLKAAEVE

TLGELVSYSKSDLMKFRNFGKKSLTELEELVHSKG

LNFGFDVAKYKLDADK

In certain embodiments, the *Chryseobacterium* strain can comprise at least one gene and/or nucleic acid comprising a sequence with at least 80%, 90%, 95%, 98%, 99%, 99.5%, 99.8%, 99.9%, or 100% sequence identity across the entire length of a sequence of:
16S_rRNA::NODE_21_length_5280_cov_261.657869: 97-1610(+) (SEQ ID NO: 78);
23S_rRNA::NODE_21_length_5280_cov_261.657869: 2222-4962(+) (SEQ ID NO: 79;
5S_rRNA::NODE_21_length_5280_cov_261.657869: 5140-5238(+) (SEQ ID NO: 80);
5S_rRNA::NODE_15_length_76839_cov_37.026828:6-85(+) (SEQ ID NO: 81); and/or
5S_rRNA::NODE_1_length_739711_cov_38.316888: 739626-739705(−) (SEQ ID NO: 82).

>16S_rRNA::NODE_21_length_5280_cov_261.657869:97-1610(+)
SEQ ID NO: 78
ATGGAGAGTTTGATCCTGGCTCAGGATGAACGCTA

GCGGGAGGCCTAACACATGCAAGCCGAGCGGTAGA

GATCTTTCGGATCTTGAGAGCGGCGTACGGGTGC

GGAACACGTGTGCAACCTGCCTTTATCAGGGGGAT

AGCCTTTCGAAAGGAAGATTAATACCCCATAATAT

ATTGAGTGGCATCACTTAATATTGAAAACTCCGGT

-continued

GGATAGAGATGGGCACGCGCAAGATTAGATAGTTG

GTGAGGTAACGGCTCACCAAGTCTGCGATCTTTAG

GGGGCCTGAGAGGGTGATCCCCCACACTGGTACTG

AGACACGGACCAGACTCCTACGGGAGGCAGCAGTG

AGGAATATTGGACAATGGGTGCGAGCCTGATCCAG

CCATCCCGCGTGAAGGACGACGGCCCTATGGGTTG

TAAACTTCTTTTGTATAGGGATAAACCTACTCTCG

TGAGAGTAGCTGAAGGTACTATACGAATAAGCACC

GGCTAACTCCGTGCCAGCAGCCGCGGTAATACGGA

GGGTGCAAGCGTTATCCGGATTTATTGGGTTTAAA

GGGTCCGTAGGCGGATCTGTAAGTCAGTGGTGAAA

TCTCACAGCTTAACTGTGAAACTGCCATTGATACT

GCAGGTCTTGAGTGTTGTTGAAGTAGCTGGAATAA

GTAGTGTAGCGGTGAAATGCATAGATATTACTTAG

AACACCAATTGCGAAGGCAGGTTACTAAGCAACAA

CTGACGCTGATGGACGAAAGCGTGGGGAGCGAACA

GGATTAGATACCCTGGTAGTCCACGCCGTAAACGA

TGCTAACTCGTTTTTGGGCTTTCGGGTTCAGAGAC

TAAGCGAAAGTGATAAGTTAGCCACCTGGGGAGTA

CGAACGCAAGTTTGAAACTCAAAGGAATTGACGGG

GGCCCGCACAAGCGGTGGATTATGTGGTTTAATTC

GATGATACGCGAGGAACCTTACCAAGGCTTAAATG

GGAAATGACAGGCTTAGAAATAGGCTTTTCTTCGG

ACATTTTTCAAGGTGCTGCATGGTTGTCGTCAGCT

CGTGCCGTGAGGTGTTAGGTTAAGTCCTGCAACGA

GCGCAACCCCTGTCACTAGTTGCCATCATTAAGTT

GGGGACTCTAGTGAGACTGCCTACGCAAGTAGAGA

GGAAGGTGGGGATGACGTCAAATCATCACGGCCCT

TACGCCTTGGGCCACACACGTAATACAATGGCCGG

TACAGAGGGCAGCTACACTGCGAAGTGATGCAAAT

CTCGAAAGCCGGTCTCAGTTCGGATTGGAGTCTGC

AACTCGACTCTATGAAGCTGGAATCGCTAGTAATC

GCGCATCAGCCATGGCGCGGTGAATACGTTCCCGG

GCCTTGTACACACCGCCCGTCAAGCCATGGAAGTC

TGGGGTACCTGAAGTCGGTGACCGTAACAGGAGCT

GCCTAGGGTAAAACAGGTAACTAGGGCTAAGTCGT

AACAAGGTAGCCGTACCGGAAGGTGCGGCTGGAAC

ATCTCATT

>23S_rRNA::NODE_21_length_5280_cov_
261.657869:2222-4962 ( +)
SEQ ID NO: 79

TCGTTAAGGGCGTATGGCGGATGCCTAGGCTTTCA

GAGGCGACGAAGGACGTGGTAAGCTGCGAAAAGCT

GCGGGGATTGGCACACACGAATTGATCCGCAGATA

TCCGAATGGGGCAACCCGGCATATTGAAGATATGT

CACCTCGTAAGAGGAGCAAACCCGGAGAACTGAAA

CATCTAAGTACCCGGAGGAAAAGAAATCGAAGAGA

TTCCGTAAGTAGTGGCGAGCGAAAGCGGATTAGCC

CAAAAGCTTTTATATGTTTAATAGAATGTTCTGGA

AAGAACAGCCATAGAGGGTGATAGCCCCGTATATG

AAAGGCATATTTGAGTGATAAATGAGTAGGGCGGG

ACACGTGAAATCCTGTCTGAATATGGGGGGACCAT

CCTCCAAGGCTAAATACTCCTGAAAGACCGATAGT

GAACAAGTACTGTGAAGGAAAGGTGAAAAGCACTT

CGAATAGAAGGGTGAAATAGAACCTGAAACCGTAC

GCCTACAAGCGGTCGGAGCAGCGTAATGCTGTGAC

GGCGTGCCTTTTGCATAATGAGCCTACGAGTTAAT

TTTACTAGCGAGGTTAAGGTATTAAGTACCGGAGC

CGAAGCGAAAGCGAGTCTGAATAGGGCGGTTAGTT

AGTAGGATTAGACGCGAAACCTTGTGATCTACCCA

TGGGCAGGTTGAAGCTCTGGTAACACAGAGTGGAG

GACCGAACCGGTTGACGTTGAAAAGTCTTCGGATG

ACCTGTGGGTAGGGGTGAAAGGCCAATCAAACTGG

GAGATAGCTCGTACTCTCCGAAATGCATTTAGGTG

CAGCGTCGATGTTAAGTTTATTAGAGGTAGAGCTA

CTGATTGGATGCGGGGGTTTCACCGCCTACCAATT

CCTGACAAACTCCGAATGCTAATAAATGTTCGTCG

GCAGTGAGGGCATGGGTGCTAAGGTCCATGTCCGA

GAGGGAAAGAACCCAGACCAACAGCTAAGGTCCCC

AAATATATGTTAAGTTGAAACAACGCGGTTGGACT

GCATTGACAGCTAGGATGTTGGCTTGGAAGCAGCC

ATTCATTTAAAGAGTGCGTAACAGCTCACTAGTCG

AGCGGTCCGGCATGGATAATAATCGGGCATAAACA

TATTACCGAAGCTATGGATTTATAATTATTATATC

TGGTAGGAGAGCATTCTATTTGCGCCGAAGCAGTA

CTGTGAGGTATTGTGGAGCGGATAGAAAAGAAAAT

GTAGGCATAAGTAACGATAAAGCAGGCGAGAAACC

TGCTCACCGAAAGACCAAGGCTTCCTCAGCCATGC

TAATCAGCTGAGGGTTAGTCGGGACCTAACGCGAA

CCCGAGAGGGGTAGTGGATGGACACAGGGTTAATA

```
TTCCCTGACTTGCTCACAATAAAAGGGGACGGTTG
GATGTATCTGCTGGAGACTGACGGAATAGTCAAGG
CCTAGCCTTCGGGCGAAGCTGCTGTAGAGTAATCT
GATCCAAGAAAAGCCGAAGTGAAGCAACCCGTACC
AAAACCGACACAGGTGGTCGAGGAGAGAATCCTAA
GGTGCTCGAGTGAGTCGTGGCTAAGGAACTAGGCA
AAATAGTCTCGTAACTTCGGAAGAAGAGACGCCAT
CAGCAATGGTGGCCGCAGTGAAGAGGCCCAGGCGA
CTGTTTATCAAAAACACAGGACTCTGCTAAATCGA
AAGATGCTGTATAGGGTCTGACACCTGCCCGGTGC
TGGAAGGTTAAGGAAGGTGCTTAGCGTAAGCGAAG
GCATTGACTGAAGCCCCAGTAAACGGCGGCCGTAA
CTATAACGGTCCTAAGGTAGCGAAATTCCTTGTCG
GGTAAGTTCCGACCTGCACGAATGGTGTAACGATC
TGGGCACTGTCTCAGCCACGAGCTCGGTGAAATTG
TAGTATCGGTGAAGATGCCGATTACCCGCAATGGG
ACGAAAAGACCCTGTGAACCTTTACTATAACTTCG
TATTGACTTTGAGTAAGTAATGTGTAGGATAGGTG
GGAGGCTTTGAAGCAGGCACGCTAGTGTTTGTGGA
GCCGACGTTGAAATACCACCCTTTACTTACTTGGA
GCCTAACTTCTTTCAGAAGGACATTGCGTGGTGGG
TAGTTTGACTGGGGTGGTCGCCTCCAAAAGAGTAA
CGGAGGCTTTCAAAGGTACCCTCAGCACGCTTGGT
AACCGTGCGTAGAGTGTAATGGCATAAGGGTGCTT
GACTGTGAGACCCACAAGTCGATCAGGTGCGAAAG
CAGGACATAGTGATCCGGTGGTTCCGTATGGAAGG
GCCATCGCTCATAGGATAAAAGGTACTCCGGGGAT

AACAGGCTAGTCTCCCCCAAGAGCTCACATCGACG
GGGAGGTTCGGCACCTCGATGTCGGCTCGTCACAT
CCTGGGGCTGGAGAAGGTCCCAAGGGTTGGGCTGT
TCGCCCATTAAAGTGGCACGCGAGCTGGGTTCAGA
ACGTCGTGAGACAGTTCGGTCTCTATCTATTGCGG
GCGTTAGATGTTTGAGAGGGCTTGATTCTAGTACG
AGAGGACCGAATTGAACAAACCTCTGGTGTATCAG
TTGTACCGCCAGGTGCACCGCTGAGTAGCTACGTT
TGGAAGAGATAAGCACTGAAAGCATATAAGTGCGA
AACTCGCCTCAAGATGAGACATCTTTTAAGGGTCG
TTGTAGATGACGACGTTGATAGGCTACAGGTGTAA
AGACAGTAATGTCATAGCCGAGTAGTACTAATTAC
CCGTAGATTT

>5S_rRNA::NODE_21_length_5280_cov_
261.657869:5140-5238 (+)
                                SEQ ID NO: 80
GTGGTTTTAGCGGTGGGGCTCACCTGTTCCCATTC
CGAACACAGAAGTTAAGCCCACCAGCGCCGATGGT
ACTGCTAACGCGGGAGAGTAGGCCGCCG >5S_rRNA::NODE_15_length_76839_cov_
37.026828:6-85(+)
                                SEQ ID NO: 81
TCACCTGTTCCCATTCCGAACACAGAAGTTAAGCC
CACCAGCGCCGATGGTACTGCTAACGCGGGAGAGT
AGGCCGCCG >5S_rRNA::NODE_1_length_739711_cov_
38.316888:739626-739705 (-)
                                SEQ ID NO: 82
TCACCTGTTCCCATTCCGAACACAGAAGTTAAGCC
CACCAGCGCCGATGGTACTGCTAACGCGGGAGAGT
AGGCCGCCG
```

SEQUENCE LISTING

The patent contains a lengthy sequence listing. A copy of the sequence listing is available in electronic form from the USPTO web site (https://seqdata.uspto.gov/?pageRequest=docDetail&DocID=US12376589B2). An electronic copy of the sequence listing will also be available from the USPTO upon request and payment of the fee set forth in 37 CFR 1.19(b)(3).

What is claimed is:

1. A method of killing an insect, said method comprising contacting an insect with a composition comprising an insecticidal indole compound, wherein said insecticidal indole compound is a diindolylalkyl compound.

2. The method of claim 1, wherein said insecticidal indole compound is 3,3-diindolylmethane.

3. The method of claim 1, wherein said insecticidal indole compound is 3-((1H-indol-2-yl)methyl)-1H-indole.

4. The method of claim 1, wherein said insect is a lepidopteran or dipteran.

5. The method of claim 1, wherein said insect is from the family Culicidae, Noctuidae, Tortricidae, Crambidae, or Erebidae.

6. The method of claim 1, wherein said insect is from the genus *Aedes*.

7. The method of claim 1, wherein said insect is from the genus *Culex, Anopheles, Trichoplusia, Spodoptera*, or *Chloridea*.

8. The method of claim 1, wherein said insect is *Ae. aegpyti, Anopheles quadrimaculatus, C. quinquefasciatus, H. viriscens, T. ni, S. exigua, C. includens, H. zea, S. eridania, S. frugiperda, D. saccharalis, D. grandiosella*, or *A. gemmetalis*.

9. The method of claim 1, wherein the insect is an insect larva, an insect pupa, and/or an insect adult.

10. The method of claim 1, further comprising surveying for a presence of an insect that is inhibited by the composition comprising the insecticidal indole compound.

11. The method of claim 1, further comprising spraying a composition comprising the insecticidal indole compound.

12. The method of claim 1, further comprising surveying a plant for insect damage.

13. The method of claim 1, wherein the insecticidal compound contacts the insect at a concentration of 0.001-1000 µg/mL.

14. A method of killing an insect, said method comprising:
    producing a culture comprising a microbial organism that is PLU6;
    isolating an insecticidal indole compound from said culture; and
    contacting an insect with a composition comprising the insecticidal indole compound, wherein said insecticidal indole compound is a diindolylalkyl compound.

15. A method of killing an insect egg, said method comprising contacting an insect egg with a composition comprising an insecticidal indole compound, wherein said insecticidal indole compound is a diindolylalkyl compound.

* * * * *